(12) United States Patent
Zhang et al.

(10) Patent No.: US 12,331,093 B2
(45) Date of Patent: Jun. 17, 2025

(54) FUSION POLYPEPTIDES FOR METABOLIC DISORDERS

(71) Applicant: BEIJING QL BIOPHARMACEUTICAL CO., LTD., Beijing (CN)

(72) Inventors: Yuanyuan Zhang, Beijing (CN); Bo Wu, Beijing (CN); Wei Guo, Beijing (CN); Xiaona Dong, Beijing (CN); Yuying Zhang, Beijing (CN)

(73) Assignee: BEIJING QL BIOPHARMACEUTICAL CO., LT, Beijing (CN)

( * ) Notice: Subject to any disclaimer, the term of this patent is extended or adjusted under 35 U.S.C. 154(b) by 0 days.

(21) Appl. No.: 18/328,796

(22) Filed: Jun. 5, 2023

(65) Prior Publication Data
US 2024/0034763 A1 Feb. 1, 2024

Related U.S. Application Data

(63) Continuation of application No. PCT/CN2022/105686, filed on Jul. 14, 2022.

(30) Foreign Application Priority Data

Jul. 14, 2021 (WO) ................ PCT/CN2021/106316

(51) Int. Cl.
| | |
|---|---|
| *C07K 14/50* | (2006.01) |
| *A61K 38/00* | (2006.01) |
| *A61P 3/00* | (2006.01) |
| *C07K 16/18* | (2006.01) |
| *C12N 15/62* | (2006.01) |
| *C12N 15/63* | (2006.01) |

(52) U.S. Cl.
CPC .............. *C07K 14/50* (2013.01); *A61K 38/00* (2013.01); *A61P 3/00* (2018.01); *C07K 14/503* (2013.01); *C07K 16/18* (2013.01); *C12N 15/62* (2013.01); *C12N 15/63* (2013.01); *C07K 2317/565* (2013.01); *C07K 2317/569* (2013.01); *C07K 2319/30* (2013.01)

(58) Field of Classification Search
CPC .................. C07K 14/50; C07K 14/605; C07K 2317/569; C07K 14/503; C07K 2319/00; A61K 38/1825; A61K 38/26; A61K 38/00; C12N 15/62; C12N 15/63
See application file for complete search history.

(56) References Cited

U.S. PATENT DOCUMENTS

| | | | |
|---|---|---|---|
| 10,124,039 B2 * | 11/2018 | Wieczorek | A61K 38/1825 |
| 2003/0220243 A1 | 11/2003 | Glaesner et al. | |
| 2004/0018975 A1 | 1/2004 | DiMarchi et al. | |
| 2005/0153890 A1 | 7/2005 | Pan et al. | |
| 2007/0036806 A1 | 2/2007 | Glaesner et al. | |
| 2007/0237768 A1 | 10/2007 | Glaesner et al. | |
| 2007/0269422 A1* | 11/2007 | Beirnaert | C07K 16/241 435/325 |
| 2007/0299007 A1 | 12/2007 | Frye et al. | |
| 2008/0045461 A1 | 2/2008 | Ewing et al. | |
| 2008/0103096 A1 | 5/2008 | Frye et al. | |
| 2008/0255045 A1 | 10/2008 | Cujec et al. | |
| 2009/0028880 A1 | 1/2009 | Beirnaert et al. | |
| 2009/0156478 A1 | 6/2009 | Lau et al. | |
| 2010/0216715 A1 | 8/2010 | Tagmose et al. | |
| 2011/0305663 A1 | 12/2011 | Gosselin et al. | |
| 2012/0129766 A1 | 5/2012 | Boettcher et al. | |
| 2012/0282279 A1 | 11/2012 | Das et al. | |
| 2013/0085098 A1 | 4/2013 | Dickinson et al. | |
| 2013/0190232 A1 | 7/2013 | Tagmose et al. | |
| 2014/0213512 A1 | 7/2014 | Ellison et al. | |
| 2014/0228546 A1 | 8/2014 | Dombrecht | |
| 2015/0011462 A1 | 1/2015 | Reedtz-Runge et al. | |
| 2015/0141335 A1 | 5/2015 | Ma et al. | |
| 2016/0115213 A1 | 4/2016 | Morin et al. | |
| 2017/0182124 A1 | 6/2017 | Wieczorek et al. | |
| 2017/0320927 A1 | 11/2017 | Sauerberg et al. | |
| 2018/0280474 A1 | 10/2018 | Xu et al. | |
| 2018/0371041 A1 | 12/2018 | Sommerfeld et al. | |
| 2019/0142963 A1 | 5/2019 | Dimarchi et al. | |
| 2019/0185533 A1 | 6/2019 | Kopec et al. | |

(Continued)

FOREIGN PATENT DOCUMENTS

| | | |
|---|---|---|
| AU | 2013202856 A1 | 5/2013 |
| AU | 2016203044 A1 | 6/2016 |

(Continued)

OTHER PUBLICATIONS

Pan et al. "A Novel GLP-1 and FGF21 dual agonist has therapeutic potential for diabetes and non-alcoholic steatohepatitis", EBioMedicine, 2021, 21 pages including supplementary (Year: 2021).*

Omar, B.A. et al. "Fibroblast Growth Factor 21 (FGF21) and Glucagon-Like Peptide 1 Contribute to Diabetes Resistance in Glucagon Receptor-Deficient Mice." Diabetes, vol. 63, No. 1, Sep. 23, 2013 (Sep. 23, 2013), pp. 101-110.

International Search Report for PCT/CN2022/105686, mailed on Oct. 10, 2022.

(Continued)

*Primary Examiner* — Melissa L Fisher
*Assistant Examiner* — John Cronin
(74) *Attorney, Agent, or Firm* — Junhe Law Office P.C.; James J . Zhu

(57) ABSTRACT

The present disclosure provides conjugates of polypeptides comprising nanobody and FGF21 linked by a polypeptide linker. The present disclosure further provides conjugates of polypeptides comprising GLP-1, nanobody, and FGF21 linked by two polypeptide linkers respectively. Pharmaceutical compositions comprising the same and methods of treating diseases are also provided.

23 Claims, 28 Drawing Sheets

Specification includes a Sequence Listing.

(56) References Cited

U.S. PATENT DOCUMENTS

2019/0201491 A1 7/2019 Canning et al.
2019/0314452 A1 10/2019 Hong et al.

FOREIGN PATENT DOCUMENTS

| CN | 103003301 A | 3/2013 | |
|---|---|---|---|
| CN | 107108710 A | 8/2017 | |
| CN | 110028587 A | 7/2019 | |
| WO | 9808871 A1 | 3/1998 | |
| WO | 0055203 A1 | 9/2000 | |
| WO | 2010065439 A1 | 6/2010 | |
| WO | WO-2017021893 A1 * | 2/2017 | ........... A61K 39/395 |
| WO | 2017074123 A1 | 5/2017 | |
| WO | 2017116207 A1 | 7/2017 | |
| WO | 2017220706 A1 | 12/2017 | |

OTHER PUBLICATIONS

First Office Action for the counterpart Chinese application No. 202280008026.3, mailed on Sep. 23, 2023.

\* cited by examiner

FGF21

| SEQ ID NO: | FGF21 Sequence | FGF21 Features |
|---|---|---|
| 1 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS | WT |
| 2 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSMVGPSQGRSPSYAS | 121Q |
| 3 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSLVGPSQGRSPSYAS | 168L |
| 4 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYES | 180E |
| 5 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGPSQGRSPSYES | N121Q, M168L, A180E |
| 6 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLCGPSQGRSPSYES | N121Q, M168L, 169C, A180E |
| 7 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLV CPSQGRSPSYES | N121Q, M168L, 170C, A180E |
| 8 | HPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGCSQGR | N121Q, M168L, 171C, A180E |

Figure 7A

| | | |
|---|---|---|
| | SPSYES | |
| 9 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGPCQGR SPSYES | N121Q, M168L, 172C, A180E |
| 10 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGPSCGRS PSYES | N121Q, M168L, 173C, A180E |
| 11 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGPSQCRS PSYES | N121Q, M168L, 174C, A180E |
| 12 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGPSQGRS PSYCS | N121Q, M168L, 180C, (NOTE: A180E gone) |
| 13 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGPSQGRS PSYEC | N121Q, M168L, A180E, 181C |
| 14 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGGSQGR SPSYES | N121Q, M168L, 171G, A180E |
| 15 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFPPLPGLPPALPEPPGILAPQPPDVGSSDPLSLVGCSQGR SPSYES | N121Q, L137P, M168L, 171C, A180E |

Figure 7B

| | | |
|---|---|---|
| 16 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGPTQGR SPSYES | N121Q, M168L, 172T, A180E |
| 17 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGPSTGRS PSYES | N121Q, M168L, 173T, A180E |
| 18 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVNPSQGRS PSYES | N121Q, M168L, 170N, A180E |
| 19 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGPSQNRS PSYES | N121Q, M168L, 174N, A180E |
| 89 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGPSQGRS PSYAS | 121Q and 168L |
| 90 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSMVGPSQGR SPSYES | 121Q and 180E |
| 91 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGNKSPHRDPAPR GPARFLPLPGLPPALPEPPGILAPQPPDVGSSDPLSLVGPSQGRS PSYES | 168L and 180E |
| 92 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGGSQC SPSYES | 121Q, 168L, P171G, 174C, and 180E |

Figure 7C

| | | |
|---|---|---|
| 102 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGNKSPHRDPAPR GPARFLPLPGLPPALPEPPGILAPQPPDVGSSDPLSLVGGSQGR SPSYES | 168L, P171G, and 180E |
| 103 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGGSQGR SPSYAS | 121Q, P171G, and 168L |
| 104 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSMVGGSQGR SPSYES | 121Q, P171G and 181E |
| 105 | HPIPDSSPLLQFGGQVRQRYLYTDDAQQTEAHLEIREDGTVGG AADQSPESLLQLKALKPGVIQILGVKTSRFLCQRPDGALYGSLHF DPEACSFRELLLEDGYNVYQSEAHGLPLHLPGQKSPHRDPAPR GPARFLPLPGLPPALPEPPGILAPQPPDVGSSDPLSLVGGSQGR SPSYES | N121Q, M168L, P171G, A180E |

Nanobody sequences

| SEQ ID | Sequence |
|---|---|
| 20 | SFGMS |
| 21 | SISGSGSDTLYADSVKG |
| 22 | GGSLSR |
| 23 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 24 | AEVQLVESGGGLVQPGNSLRLSCAASGFTFSSFGMSWVRQAPGKGLEWVSSISGSGSDTLYADSVKGRFTISR |

Figure 7D

|    | |
|----|------------------------------------------------------------|
|    | DNAKTTLYLQMNSLRPEDTAVYYCTIGGSLSRSSQGTLVTVSS |
| 25 | SEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 26 | AGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 27 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |

GLP-1 sequences

| SEQ ID NO: | GLP-1 Sequence | GLP-1 Features |
|---|---|---|
| 28 | HAEGTFTSDVSSYLEGQAAKEFIAWLVKGRG | GLP1-WT |
| 29 | HGEGTFTSDVSSYLEEQAAKEFIAWLVKGGG | 8G, 22E, 36G |
| 30 | EGTFTSDVSSYLEEQAAKEFIAWLVKGGG | del7-8 (inactive), 22E, 36G |
| 31 | HGEGTFTSDVSSYLEEQAAKEFIAWLVRGGG | 8G, 22E, 34R, 36G |
| 32 | HGEGTFTSDVSSYLEEQAAREFIAWLVRGGG | 8G, 22E, 26R, 34R, 36G |
| 33 | HGEGTFTSDVSSYLEEQAAREFIAWLVRGKG | 8G, 22E, 26R, 34R, 36K |
| 34 | HGEGTFTSDVSSYLEEQAAREFIAWLVRGGG | 8G, 22E, 26R, 36G |

Figure 7E

First and second linker

| SEQ ID NO: | 1st/2nd Linker Sequence | Features |
|---|---|---|
| 35 | GAQP | (GAQP)1 |
| 36 | GQAP | |
| 37 | GPAQ | |
| 38 | GPQA | |
| 39 | GSQP | |
| 40 | GASP | |
| 41 | GPAS | |
| 42 | GPSA | |
| 43 | GGGS | |
| 44 | GSGS | |
| 45 | GGGGS | |
| 46 | GSAPGSPAGSPTGSAPGSPA | |
| 47 | GGGGSGGGGSGGGGSGGGGS | (G4S)4 |
| 48 | GGGGSGGGS | G4SG3S |
| 49 | GAQPGAQP | (GAQP)2 |
| 50 | GAQPGAQPGAQPGAQPGAQP | (GAQP)5 |
| 51 | GAQPGAQPGAQPGAQPGAQPGAQPGAQPGAQPGAQPGAQP | (GAQP)10 |
| 52 | GAQPGAQPGAQPGAQPGAQPGAQPGAQPGAQPGAQPGAQPGAQPGAQPGAQPGAQP | (GAQP)14 |
| 53 | GQEPGAQPGQEPGAQPGQEPGAQPGQEPGAQPGQEPGAQPGQEPGAQP | (GQEPGAQP)6 |
| 54 | GGGGGSGGGSGGGGS | G5SG3SG4S |
| 55 | GQEP | |
| 56 | GEQP | |
| 57 | GPQE | |
| 58 | GPEQ | |
| 59 | GSEP | |
| 60 | GESP | |
| 61 | GPSE | |
| 62 | GPES | |
| 106 | GAQPGAQPGAQPGAQPGAQPGAQPGAQPGAQPGAQPGAQPGAQPGAQPGAQPGGGGS | (GAQP)13(G4S) |

Figure 7F

Nanobody-FGF21 sequences

| SEQ ID NO: | Sequence |
|---|---|
| 63 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGAQPGAQPGAQPGAQPGAQPGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGCSQGRSPSYES |
| 64 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGAQPGAQPGAQPGAQPGAQPGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGGSQGRSPSYES |
| 65 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPGAQPGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGGSQGRSPSYES |
| 66 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGGSQGRSPSYES |
| 67 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGGSQGRSPSYES |
| 68 | SGEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGCSQGRSPSYES |
| 69 | MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTIS |

Figure 7G

| | |
|---|---|
| | KAKGQPREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGKGGGGGS GGGSGGGGSHPIPDSSPLLQFGGQVRQRYLYTDDAQQTEAHLEIREDGTVGGAADQS PESLLQLKALKPGVIQILGVKTSRFLCQRPDGALYGSLHFDPEACSFRERLLEDGYNVYQS EAHGLPLHLPGNKSPHRDPAPRGPARFLPLGLPPAPPEPPGILAPQPPDVGSSDPLSM VGGSQGRSPSYES |
| 93 | SGEVQLVESGGGLVQPGNSLRLSCAASGFTFSSFGMSWVRQAPGKGLEWVSSISGSGS DTLYADSVKGRFTISRDNAKTTLYLQMNSLRPEDTAVYYCTIGGSLSRSSQGTLVTVSSG AQPHPIPDSSPLLQFGGQVRQRYLYTDDAQQTEAHLEIREDGTVGGAADQSPESLLQL KALKPGVIQILGVKTSRFLCQRPDGALYGSLHFDPEACSFRELLLEDGYNVYQSEAHGLPL HLPGQKSPHRDPAPRGPARFLPLPGLPPALPEPPGILAPQPPDVGSSDPLSLVGGSQCRS PSYES |
| 99 | SGEVQLVESGGGLVQPGNSLRLSCAASGFTFSSFGMSWVRQAPGKGLEWVSSISGSGS DTLYADSVKGRFTISRDNAKTTLYLQMNSLRPEDTAVYYCTIGGSLSRSSQGTLVTVSSG AQPHPIPDSSPLLQFGGQVRQRYLYTDDAQQTEAHLEIREDGTVGGAADQSPESLLQL KALKPGVIQILGVKTSRFLCQRPDGALYGSLHFDPEACSFRELLLEDGYNVYQSEAHGLPL HLPGQKSPHRDPAPRGPARFLPLPGLPPALPEPPGILAPQPPDVGSSDPLSLVGPSQGRS PSYES |
| 100 | SGEVQLVESGGGLVQPGNSLRLSCAASGFTFSSFGMSWVRQAPGKGLEWVSSISGSGS DTLYADSVKGRFTISRDNAKTTLYLQMNSLRPEDTAVYYCTIGGSLSRSSQGTLVTVSSG GGGSHPIPDSSPLLQFGGQVRQRYLYTDDAQQTEAHLEIREDGTVGGAADQSPESLLQ LKALKPGVIQILGVKTSRFLCQRPDGALYGSLHFDPEACSFRELLLEDGYNVYQSEAHGLP LHLPGQKSPHRDPAPRGPARFLPLPGLPPALPEPPGILAPQPPDVGSSDPLSLVGCSQGR SPSYES |
| 101 | SGEVQLVESGGGLVQPGNSLRLSCAASGFTFSSFGMSWVRQAPGKGLEWVSSISGSGS DTLYADSVKGRFTISRDNAKTTLYLQMNSLRPEDTAVYYCTIGGSLSRSSQGTLVTVSSG GGGSHPIPDSSPLLQFGGQVRQRYLYTDDAQQTEAHLEIREDGTVGGAADQSPESLLQ LKALKPGVIQILGVKTSRFLCQRPDGALYGSLHFDPEACSFRELLLEDGYNVYQSEAHGLP LHLPGQKSPHRDPAPRGPARFLPLPGLPPALPEPPGILAPQPPDVGSSDPLSLVGPSQGR SPSYES |
| 107 | SGEVQLVESGGGLVQPGNSLRLSCAASGFTFSSFGMSWVRQAPGKGLEWVSSISGSGS DTLYADSVKGRFTISRDNAKTTLYLQMNSLRPEDTAVYYCTIGGSLSRSSQGTLVTVSSG GGGSHPIPDSSPLLQFGGQVRQRYLYTDDAQQTEAHLEIREDGTVGGAADQSPESLLQ LKALKPGVIQILGVKTSRFLCQRPDGALYGSLHFDPEACSFRELLLEDGYNVYQSEAHGLP LHLPGQKSPHRDPAPRGPARFLPLPGLPPALPEPPGILAPQPPDVGSSDPLSLVGGSQGR SPSYES |

Figure 7H

GLP-1-Nanobody-FGF21 sequences

| SEQ ID NO: | Sequence |
|---|---|
| 70 | HGEGTFTSDVSSYLEEQAAKEFIAWLVKGGGGGGGSGGGGSGGGGS GGGGSEVQLVESGGGLVQPGNSLRLSCAASGFTFSSFGMSWVRQAP GKGLEWVSSISGSGSDTLYADSVKGRFTISRDNAKTTLYLQMNSLRPE DTAVYYCTIGGSLSRSSQGTLVTVSSGGGGSGGGSHPIPDSSPLLQFG GQVRQRYLYTDDAQQTEAHLEIREDGTVGGAADQSPESLLQLKALKPG VIQILGVKTSRFLCQRPDGALYGSLHFDPEACSFRELLLEDGYNVYQSE AHGLPLHLPGQKSPHRDPAPRGPARFLPLGLPPALPEPPGILAPQPP DVGSSDPLSLVGGSQGRSPSYES |
| 71 | EGTFTSDVSSYLEEQAAKEFIAWLVKGGGGGGGSGGGGSGGGGSGG GGSEVQLVESGGGLVQPGNSLRLSCAASGFTFSSFGMSWVRQAPGK GLEWVSSISGSGSDTLYADSVKGRFTISRDNAKTTLYLQMNSLRPEDTA VYYCTIGGSLSRSSQGTLVTVSSGGGGSGGGSHPIPDSSPLLQFGGQV RQRYLYTDDAQQTEAHLEIREDGTVGGAADQSPESLLQLKALKPGVIQI LGVKTSRFLCQRPDGALYGSLHFDPEACSFRELLLEDGYNVYQSEAHG LPLHLPGQKSPHRDPAPRGPARFLPLGLPPALPEPPGILAPQPPDVGS SDPLSLVGGSQGRSPSYES |
| 72 | EGTFTSDVSSYLEEQAAKEFIAWLVKGGGGAQPGAQPGAQPGAQPGAQPEVQL VESGGGLVQPGNSLRLSCAASGFTFSSFGMSWVRQAPGKGLEWVSSISGSGSDTL YADSVKGRFTISRDNAKTTLYLQMNSLRPEDTAVYYCTIGGSLSRSSQGTLVTVSSG AQPGAQPGAQPGAQPGAQPGAQPGAQPGAQPGAQPGAQPHPIPDSSPLLQF GGQVRQRYLYTDDAQQTEAHLEIREDGTVGGAADQSPESLLQLKALKPGVIQILG VKTSRFLCQRPDGALYGSLHFDPEACSFRELLLEDGYNVYQSEAHGLPLHLPGQKS PHRDPAPRGPARFLPLGLPPALPEPPGILAPQPPDVGSSDPLSLVGGSQGRSPSYE S |
| 73 | EGTFTSDVSSYLEEQAAKEFIAWLVKGGGGAQPGAQPGAQPGAQPGAQPEVQL VESGGGLVQPGNSLRLSCAASGFTFSSFGMSWVRQAPGKGLEWVSSISGSGSDTL YADSVKGRFTISRDNAKTTLYLQMNSLRPEDTAVYYCTIGGSLSRSSQGTLVTVSSG QEPGAQPGQEPGAQPGQEPGAQPGQEPGAQPGQEPGAQPHPIP DSSPLLQFGGQVRQRYLYTDDAQQTEAHLEIREDGTVGGAADQSPESLLQLKALK PGVIQILGVKTSRFLCQRPDGALYGSLHFDPEACSFRELLLEDGYNVYQSEAHGLPL HLPGQKSPHRDPAPRGPARFLPLGLPPALPEPPGILAPQPPDVGSSDPLSLVGGS QGRSPSYES |
| 74 | HGEGTFTSDVSSYLEEQAAKEFIAWLVKGGGGAQPGAQPGAQPGAQPGAQPEV QLVESGGGLVQPGNSLRLSCAASGFTFSSFGMSWVRQAPGKGLEWVSSISGSGS DTLYADSVKGRFTISRDNAKTTLYLQMNSLRPEDTAVYYCTIGGSLSRSSQGTLVTV SSGAQPGAQPGAQPGAQPGAQPGAQPGAQPGAQPGAQPGAQPHPIPDSSPLL QFGGQVRQRYLYTDDAQQTEAHLEIREDGTVGGAADQSPESLLQLKALKPGVIQI LGVKTSRFLCQRPDGALYGSLHFDPEACSFRELLLEDGYNVYQSEAHGLPLHLPGQ KSPHRDPAPRGPARFLPLGLPPALPEPPGILAPQPPDVGSSDPLSLVGCSQGRSPS YES |
| 75 | HGEGTFTSDVSSYLEEQAAKEFIAWLVKGGGGAQPGAQPGAQPGAQPGAQPEV QLVESGGGLVQPGNSLRLSCAASGFTFSSFGMSWVRQAPGKGLEWVSSISGSGS |

Figure 7I

| | |
|---|---|
| | DTLYADSVKGRFTISRDNAKTTLYLMNSLRPEDTAVYYCTIGGSLSRSSQGTLVTV SSGAQPGAQPGAQPGAQPGAQPGAQPGAQPGAQPGAQPGAQPHPIPDSSPLL QFGGQVRQRYLYTDDAQQTEAHLEIREDGTVGGAADQSPESLLQLKALKPGVIQI LGVKTSRFLCQRPDGALYGSLHFDPEACSFRELLLEDGYNVYQSEAHGLPLHLPGQ KSPHRDPAPRGPARFLPLPGLPPALPEPPGILAPQPPDVGSSDPLSLVGGSQGRSP SYES |
| 76 | EGTFTSDVSSYLEEQAAKEFIAWLVKGGGGAQPGAQPGAQPGAQPGAQPEVQL VESGGGLVQPGNSLRLSCAASGFTFSSFGMSWVRQAPGKGLEWVSSISGSGSDTL YADSVKGRFTISRDNAKTTLYLMNSLRPEDTAVYYCTIGGSLSRSSQGTLVTVSSG AQPGAQPGAQPGAQPGAQPHPIPDSSPLLQFGGQVRQRYLYTDDAQQTEAHLE IREDGTVGGAADQSPESLLQLKALKPGVIQILGVKTSRFLCQRPDGALYGSLHFDPE ACSFRELLLEDGYNVYQSEAHGLPLHLPGQKSPHRDPAPRGPARFLPLPGLPPALP EPPGILAPQPPDVGSSDPLSLVGGSQGRSPSYES |
| 77 | EGTFTSDVSSYLEEQAAKEFIAWLVKGGGGAQPGAQPGAQPGAQPGAQPEVQL VESGGGLVQPGNSLRLSCAASGFTFSSFGMSWVRQAPGKGLEWVSSISGSGSDTL YADSVKGRFTISRDNAKTTLYLMNSLRPEDTAVYYCTIGGSLSRSSQGTLVTVSSG AQPGAQPHPIPDSSPLLQFGGQVRQRYLYTDDAQQTEAHLEIREDGTVGGAADQ SPESLLQLKALKPGVIQILGVKTSRFLCQRPDGALYGSLHFDPEACSFRELLLEDGYN VYQSEAHGLPLHLPGQKSPHRDPAPRGPARFLPLPGLPPALPEPPGILAPQPPDVG SSDPLSLVGGSQGRSPSYES |
| 78 | EGTFTSDVSSYLEEQAAKEFIAWLVKGGGGAQPGAQPGAQPGAQPGAQPEVQL VESGGGLVQPGNSLRLSCAASGFTFSSFGMSWVRQAPGKGLEWVSSISGSGSDTL YADSVKGRFTISRDNAKTTLYLMNSLRPEDTAVYYCTIGGSLSRSSQGTLVTVSSG AQPHPIPDSSPLLQFGGQVRQRYLYTDDAQQTEAHLEIREDGTVGGAADQSPESL LQLKALKPGVIQILGVKTSRFLCQRPDGALYGSLHFDPEACSFRELLLEDGYNVYQS EAHGLPLHLPGQKSPHRDPAPRGPARFLPLPGLPPALPEPPGILAPQPPDVGSSDP LSLVGGSQGRSPSYES |
| 79 | HGEGTFTSDVSSYLEEQAAKEFIAWLVKGGGGAQPGAQPGAQPGAQPGAQPGA QPGAQPGAQPGAQPEVQLVESGGGLVQPGNSLRLSCAASGFTFSSFGMS WVRQAPGKGLEWVSSISGSGSDTLYADSVKGRFTISRDNAKTTLYLMNSLRPED TAVYYCTIGGSLSRSSQGTLVTVSSGAQPGAQPGAQPGAQPGAQPGAQPGAQP GAQPGAQPHPIPDSSPLLQFGGQVRQRYLYTDDAQQTEAHLEIREDGTVG GAADQSPESLLQLKALKPGVIQILGVKTSRFLCQRPDGALYGSLHFDPEACSFRELL LEDGYNVYQSEAHGLPLHLPGQKSPHRDPAPRGPARFLPLPGLPPALPEPPGILAP QPPDVGSSDPLSLVGGSQGRSPSYES |
| 80 | HGEGTFTSDVSSYLEEQAAKEFIAWLVKGGGGAQPGAQPGAQPGAQPGAQPEV QLVESGGGLVQPGNSLRLSCAASGFTFSSFGMSWVRQAPGKGLEWVSSISGSGS DTLYADSVKGRFTISRDNAKTTLYLMNSLRPEDTAVYYCTIGGSLSRSSQGTLVTV SSGAQPHPIPDSSPLLQFGGQVRQRYLYTDDAQQTEAHLEIREDGTVGGAADQS PESLLQLKALKPGVIQILGVKTSRFLCQRPDGALYGSLHFDPEACSFRELLLEDGYNV YQSEAHGLPLHLPGQKSPHRDPAPRGPARFLPLPGLPPALPEPPGILAPQPPDVGS SDPLSLVGGSQGRSPSYES |

Figure 7J

| 81 | HGEGTFTSDVSSYLEEQAAKEFIAWLVKGGGGAQPGAQPGAQPGAQPGAQPEV QLVESGGGLVQPGNSLRLSCAASGFTFSSFGMSWVRQAPGKGLEWVSSISGSGS DTLYADSVKGRFTISRDNAKTTLYLQMNSLRPEDTAVYYCTIGGSLSRSSQGTLVTV SSGAQPHPIPDSSPLLQFGGQVRQRYLYTDDAQQTEAHLEIREDGTVGGAADQS PESLLQLKALKPGVIQILGVKTSRFLCQRPDGALYGSLHFDPEACSFRELLLEDGYNV YQSEAHGLPLHLPGQKSPHRDPAPRGPARFLPLPGLPPALPEPPGILAPQPPDVGS SDPLSLVGCSQGRSPSYES |
| 82 | HGEGTFTSDVSSYLEEQAAKEFIAWLVKGGGGAQPGAQPGAQPGAQPGAQPGA QPGAQPGAQPGAQPEVQLVESGGGLVQPGNSLRLSCAASGFTFSSFGMS WVRQAPGKGLEWVSSISGSGSDTLYADSVKGRFTISRDNAKTTLYLQMNSLRPED TAVYYCTIGGSLSRSSQGTLVTVSSGAQPHPIPDSSPLLQFGGQVRQRYLYTDDAQ QTEAHLEIREDGTVGGAADQSPESLLQLKALKPGVIQILGVKTSRFLCQRPDGALY GSLHFDPEACSFRELLLEDGYNVYQSEAHGLPLHLPGQKSPHRDPAPRGPARFLPL PGLPPALPEPPGILAPQPPDVGSSDPLSLVGCSQGRSPSYES |
| 83 | HGEGTFTSDVSSYLEEQAAKEFIAWLVKGGGGAQPGAQPEVQLVESGGGLVQPG NSLRLSCAASGFTFSSFGMSWVRQAPGKGLEWVSSISGSGSDTLYADSVKGRFTIS RDNAKTTLYLQMNSLRPEDTAVYYCTIGGSLSRSSQGTLVTVSSGAQPHPIPDSSP LLQFGGQVRQRYLYTDDAQQTEAHLEIREDGTVGGAADQSPESLLQLKALKPGVI QILGVKTSRFLCQRPDGALYGSLHFDPEACSFRELLLEDGYNVYQSEAHGLPLHLP GQKSPHRDPAPRGPARFLPLPGLPPALPEPPGILAPQPPDVGSSDPLSLVGCSQGR SPSYES |
| 84 | EGTFTSDVSSYLEEQAAKEFIAWLVKGGGGAQPGAQPGAQPGAQPGAQPEVQL VESGGGLVQPGNSLRLSCAASGFTFSSFGMSWVRQAPGKGLEWVSSISGSGSDTL YADSVKGRFTISRDNAKTTLYLQMNSLRPEDTAVYYCTIGGSLSRSSQGTLVTVSSH PIPDSSPLLQFGGQVRQRYLYTDDAQQTEAHLEIREDGTVGGAADQSPESLLQLK ALKPGVIQILGVKTSRFLCQRPDGALYGSLHFDPEACSFRELLLEDGYNVYQSEAHG LPLHLPGQKSPHRDPAPRGPARFLPLPGLPPALPEPPGILAPQPPDVGSSDPLSLVG GSQGRSPSYES |
| 85 | HGEGTFTSDVSSYLEEQAAKEFIAWLVKGGGGAQPGAQPGAQPGAQPGAQPGA QPGAQPGAQPGAQPGAQPGAQPGAQPGAQPEVQLVESGGGLVQPGN SLRLSCAASGFTFSSFGMSWVRQAPGKGLEWVSSISGSGSDTLYADSVKGRFTISR DNAKTTLYLQMNSLRPEDTAVYYCTIGGSLSRSSQGTLVTVSSGAQPHPIPDSSPLL QFGGQVRQRYLYTDDAQQTEAHLEIREDGTVGGAADQSPESLLQLKALKPGVIQI LGVKTSRFLCQRPDGALYGSLHFDPEACSFRELLLEDGYNVYQSEAHGLPLHLPGQ KSPHRDPAPRGPARFLPLPGLPPALPEPPGILAPQPPDVGSSDPLSLVGCSQGRSPS YES |
| 86 | EGTFTSDVSSYLEEQAAKEFIAWLVKGGGGAQPGAQPGAQPGAQPGAQPGAQP GAQPGAQPGAQPGAQPGAQPGAQPGAQPEVQLVESGGGLVQPGNSLR LSCAASGFTFSSFGMSWVRQAPGKGLEWVSSISGSGSDTLYADSVKGRFTISRDN AKTTLYLQMNSLRPEDTAVYYCTIGGSLSRSSQGTLVTVSSGAQPHPIPDSSPLLQF GGQVRQRYLYTDDAQQTEAHLEIREDGTVGGAADQSPESLLQLKALKPGVIQILG VKTSRFLCQRPDGALYGSLHFDPEACSFRELLLEDGYNVYQSEAHGLPLHLPGQKS |

Figure 7K

| | |
|---|---|
| | PHRDPAPRGPARFLPLPGLPPALPEPPGILAPQPPDVGSSDPLSLVGCSQGRSPSYES |
| 87 | HGEGTFTSDVSSYLEEQAAKEFIAWLVKGGGGAQPGAQPGAQPGAQPGAQPGAQPGAQPGAQPGAQPGAQPGAQPGAQPGAQPEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFPPLPGLPPALPEPPGILAPQPPDVGSSDPLSLVGCSQGRSPSYES |
| 88 | EGTFTSDVSSYLEEQAAKEFIAWLVKGGGGAQPGAQPGAQPGAQPGAQPGAQPGAQPGAQPGAQPGAQPGAQPGAQPGAQPGAQPEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFPPLPGLPPALPEPPGILAPQPPDVGSSDPLSLVGCSQGRSPSYES |
| 94 | HGEGTFTSDVSSYLEEQAAKEFIAWLVKGGGGAQPGAQPGAQPGAQPGAQPGAQPGAQPGAQPGAQPGAQPGAQPGAQPEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGGSQCRSPSYES |
| 95 | HGEGTFTSDVSSYLEEQAAKEFIAWLVKGGGGAQPGAQPGAQPGAQPGAQPGAQPGAQPGAQPGAQPGAQPGAQPGAQPEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAQPHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGPSQGRSPSYES |
| 96 | HGEGTFTSDVSSYLEEQAAKEFIAWLVKGGGGAQPGAQPGAQPGAQPGAQPGAQPGAQPGAQPGAQPGAQPGAQPGAQPEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGQKSPHRDPAPRGPARFLPLPGLPPALPEPPGILAPQPPDVGSSDPLSLVGCSQGRSPSYES |

Figure 7L

| 97 | HGEGTFTSDVSSYLEEQAAKEFIAWLVKGGGGAQPGAQPGAQPGAQPGAQPGA QPGAQPGAQPGAQPGAQPGAQPGAQPGGGGSEVQLVESGGGLVQPG NSLRLSCAASGFTFSSFGMSWVRQAPGKGLEWVSSISGSGSDTLYADSVKGRFTIS RDNAKTTLYLQMNSLRPEDTAVYYCTIGGSLSRSSQGTLVTVSSGGGGSHPIPDSS PLLQFGGQVRQRYLYTDDAQQTEAHLEIREDGTVGGAADQSPESLLQLKALKPGV IQILGVKTSRFLCQRPDGALYGSLHFDPEACSFRELLLEDGYNVYQSEAHGLPLHLP GQKSPHRDPAPRGPARFLPLPGLPPALPEPPGILAPQPPDVGSSDPLSLVGCSQGR SPSYES |
|---|---|
| 98 | HGEGTFTSDVSSYLEEQAAKEFIAWLVKGGGGAQPGAQPGAQPGAQPGAQPGA QPGAQPGAQPGAQPGAQPGAQPGAQPGAQPEVQLVESGGGLVQPGN SLRLSCAASGFTFSSFGMSWVRQAPGKGLEWVSSISGSGSDTLYADSVKGRFTISR DNAKTTLYLQMNSLRPEDTAVYYCTIGGSLSRSSQGTLVTVSSGGGGSHPIPDSSP LLQFGGQVRQRYLYTDDAQQTEAHLEIREDGTVGGAADQSPESLLQLKALKPGVI QILGVKTSRFLCQRPDGALYGSLHFDPEACSFRELLLEDGYNVYQSEAHGLPLHLP GQKSPHRDPAPRGPARFLPLPGLPPALPEPPGILAPQPPDVGSSDPLSLVGPSQGR SPSYES |
| 108 | HGEGTFTSDVSSYLEEQAAKEFIAWLVKGGGGAQPGAQPGAQPGAQPGAQPGA QPGAQPGAQPGAQPGAQPGAQPGAQPGAQPEVQLVESGGGLVQPGN SLRLSCAASGFTFSSFGMSWVRQAPGKGLEWVSSISGSGSDTLYADSVKGRFTISR DNAKTTLYLQMNSLRPEDTAVYYCTIGGSLSRSSQGTLVTVSSGAQPHPIPDSSPLL QFGGQVRQRYLYTDDAQQTEAHLEIREDGTVGGAADQSPESLLQLKALKPGVIQI LGVKTSRFLCQRPDGALYGSLHFDPEACSFRELLLEDGYNVYQSEAHGLPLHLGQ KSPHRDPAPRGPARFLPLPGLPPALPEPPGILAPQPPDVGSSDPLSLVGGSQGRSP SYES |
| 109 | HGEGTFTSDVSSYLEEQAAKEFIAWLVKGGGGAQPGAQPGAQPGAQPGAQPGA QPGAQPGAQPGAQPGAQPGAQPGAQPGAQPEVQLVESGGGLVQPGN SLRLSCAASGFTFSSFGMSWVRQAPGKGLEWVSSISGSGSDTLYADSVKGRFTISR DNAKTTLYLQMNSLRPEDTAVYYCTIGGSLSRSSQGTLVTVSSGGGGSHPIPDSSP LLQFGGQVRQRYLYTDDAQQTEAHLEIREDGTVGGAADQSPESLLQLKALKPGVI QILGVKTSRFLCQRPDGALYGSLHFDPEACSFRELLLEDGYNVYQSEAHGLPLHLP GQKSPHRDPAPRGPARFLPLPGLPPALPEPPGILAPQPPDVGSSDPLSLVGGSQGR SPSYES |

Figure 7M

SEQUENCE LISTING

```
Sequence total quantity: 110
SEQ ID NO: 1            moltype = AA  length = 181
FEATURE                 Location/Qualifiers
source                  1..181
                        mol_type = protein
                        organism = Homo sapiens
SEQUENCE: 1
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG 120
NKSPHRDPAP RGPARFLPLP GLPPALPEPP GILAPQPPDV GSSDPLSMVG PSQGRSPSYA 180
S                                                                181

SEQ ID NO: 2            moltype = AA  length = 181
FEATURE                 Location/Qualifiers
REGION                  1..181
                        note = Synthetic
```

```
                    source              1..181
                                        mol_type = protein
                                        organism = synthetic construct
SEQUENCE: 2
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSMVG PSQGRSPSYA   180
S                                                                  181

SEQ ID NO: 3            moltype = AA   length = 181
FEATURE                 Location/Qualifiers
REGION                  1..181
                        note = Synthetic
source                  1..181
                        mol_type = protein
                        organism = synthetic construct
SEQUENCE: 3
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
NKSPHRDPAP RGPARFLPLP GLPPALPEPP GILAPQPPDV GSSDPLSLVG PSQGRSPSYA   180
S                                                                  181

SEQ ID NO: 4            moltype = AA   length = 181
FEATURE                 Location/Qualifiers
REGION                  1..181
                        note = Synthetic
source                  1..181
                        mol_type = protein
                        organism = synthetic construct
SEQUENCE: 4
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
NKSPHRDPAP RGPARFLPLP GLPPALPEPP GILAPQPPDV GSSDPLSMVG PSQGRSPSYE   180
S                                                                  181

SEQ ID NO: 5            moltype = AA   length = 181
FEATURE                 Location/Qualifiers
REGION                  1..181
                        note = Synthetic
source                  1..181
                        mol_type = protein
                        organism = synthetic construct
SEQUENCE: 5
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVG PSQGRSPSYE   180
S                                                                  181

SEQ ID NO: 6            moltype = AA   length = 181
FEATURE                 Location/Qualifiers
REGION                  1..181
                        note = Synthetic
source                  1..181
                        mol_type = protein
                        organism = synthetic construct
SEQUENCE: 6
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLCG PSQGRSPSYE   180
S                                                                  181

SEQ ID NO: 7            moltype = AA   length = 181
FEATURE                 Location/Qualifiers
REGION                  1..181
                        note = Synthetic
source                  1..181
                        mol_type = protein
                        organism = synthetic construct
SEQUENCE: 7
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVC PSQGRSPSYE   180
S                                                                  181

SEQ ID NO: 8            moltype = AA   length = 181
FEATURE                 Location/Qualifiers
REGION                  1..181
                        note = Synthetic
source                  1..181
```

```
                        mol_type = protein
                        organism = synthetic construct
SEQUENCE: 8
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
QKSPHRDPAP RGPARFLPLP GLPPALPEPP GILAPQPPDV GSSDPLSLVG CSQGRSPSYE  180
S                                                                 181

SEQ ID NO: 9            moltype = AA  length = 181
FEATURE                 Location/Qualifiers
REGION                  1..181
                        note = Synthetic
source                  1..181
                        mol_type = protein
                        organism = synthetic construct
SEQUENCE: 9
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
QKSPHRDPAP RGPARFLPLP GLPPALPEPP GILAPQPPDV GSSDPLSLVG PCQGRSPSYE  180
S                                                                 181

SEQ ID NO: 10           moltype = AA  length = 181
FEATURE                 Location/Qualifiers
REGION                  1..181
                        note = Synthetic
source                  1..181
                        mol_type = protein
                        organism = synthetic construct
SEQUENCE: 10
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
QKSPHRDPAP RGPARFLPLP GLPPALPEPP GILAPQPPDV GSSDPLSLVG PSCGRSPSYE  180
S                                                                 181

SEQ ID NO: 11           moltype = AA  length = 181
FEATURE                 Location/Qualifiers
REGION                  1..181
                        note = Synthetic
source                  1..181
                        mol_type = protein
                        organism = synthetic construct
SEQUENCE: 11
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
QKSPHRDPAP RGPARFLPLP GLPPALPEPP GILAPQPPDV GSSDPLSLVG PSQCRSPSYE  180
S                                                                 181

SEQ ID NO: 12           moltype = AA  length = 181
FEATURE                 Location/Qualifiers
REGION                  1..181
                        note = Synthetic
source                  1..181
                        mol_type = protein
                        organism = synthetic construct
SEQUENCE: 12
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
QKSPHRDPAP RGPARFLPLP GLPPALPEPP GILAPQPPDV GSSDPLSLVG PSQGRSPSYC  180
S                                                                 181

SEQ ID NO: 13           moltype = AA  length = 181
FEATURE                 Location/Qualifiers
REGION                  1..181
                        note = Synthetic
source                  1..181
                        mol_type = protein
                        organism = synthetic construct
SEQUENCE: 13
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
QKSPHRDPAP RGPARFLPLP GLPPALPEPP GILAPQPPDV GSSDPLSLVG PSQGRSPSYE  180
C                                                                 181

SEQ ID NO: 14           moltype = AA  length = 181
FEATURE                 Location/Qualifiers
REGION                  1..181
                        note = Synthetic
source                  1..181
                        mol_type = protein
```

```
                                   organism = synthetic construct
SEQUENCE: 14
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVG GSQGRSPSYE   180
S                                                                  181

SEQ ID NO: 15              moltype = AA   length = 181
FEATURE                    Location/Qualifiers
REGION                     1..181
                           note = Synthetic
source                     1..181
                           mol_type = protein
                           organism = synthetic construct
SEQUENCE: 15
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFPPLP GLPPALPEPP GILAPQPPDV GSSDPLSLVG CSQGRSPSYE   180
S                                                                  181

SEQ ID NO: 16              moltype = AA   length = 181
FEATURE                    Location/Qualifiers
REGION                     1..181
                           note = Synthetic
source                     1..181
                           mol_type = protein
                           organism = synthetic construct
SEQUENCE: 16
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVG PTQGRSPSYE   180
S                                                                  181

SEQ ID NO: 17              moltype = AA   length = 181
FEATURE                    Location/Qualifiers
REGION                     1..181
                           note = Synthetic
source                     1..181
                           mol_type = protein
                           organism = synthetic construct
SEQUENCE: 17
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVG PSTGRSPSYE   180
S                                                                  181

SEQ ID NO: 18              moltype = AA   length = 181
FEATURE                    Location/Qualifiers
REGION                     1..181
                           note = Synthetic
source                     1..181
                           mol_type = protein
                           organism = synthetic construct
SEQUENCE: 18
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVN PSQGRSPSYE   180
S                                                                  181

SEQ ID NO: 19              moltype = AA   length = 181
FEATURE                    Location/Qualifiers
REGION                     1..181
                           note = Synthetic
source                     1..181
                           mol_type = protein
                           organism = synthetic construct
SEQUENCE: 19
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVG PSQNRSPSYE   180
S                                                                  181

SEQ ID NO: 20              moltype = AA   length = 5
FEATURE                    Location/Qualifiers
REGION                     1..5
                           note = Synthetic
source                     1..5
                           mol_type = protein
                           organism = synthetic construct
```

```
SEQUENCE: 20
SFGMS                                                                     5

SEQ ID NO: 21           moltype = AA  length = 17
FEATURE                 Location/Qualifiers
REGION                  1..17
                        note = Synthetic
source                  1..17
                        mol_type = protein
                        organism = synthetic construct
SEQUENCE: 21
SISGSGSDTL YADSVKG                                                       17

SEQ ID NO: 22           moltype = AA  length = 6
FEATURE                 Location/Qualifiers
REGION                  1..6
                        note = Synthetic
source                  1..6
                        mol_type = protein
                        organism = synthetic construct
SEQUENCE: 22
GGSLSR                                                                    6

SEQ ID NO: 23           moltype = AA  length = 115
FEATURE                 Location/Qualifiers
REGION                  1..115
                        note = Synthetic
source                  1..115
                        mol_type = protein
                        organism = synthetic construct
SEQUENCE: 23
EVQLVESGGG LVQPGNSLRL SCAASGFTFS SFGMSWVRQA PGKGLEWVSS ISGSGSDTLY         60
ADSVKGRFTI SRDNAKTTLY LQMNSLRPED TAVYYCTIGG SLSRSSQGTL VTVSS             115

SEQ ID NO: 24           moltype = AA  length = 116
FEATURE                 Location/Qualifiers
REGION                  1..116
                        note = Synthetic
source                  1..116
                        mol_type = protein
                        organism = synthetic construct
SEQUENCE: 24
AEVQLVESGG GLVQPGNSLR LSCAASGFTF SSFGMSWVRQ APGKGLEWVS SISGSGSDTL         60
YADSVKGRFT ISRDNAKTTL YLQMNSLRPE DTAVYYCTIG GSLSRSSQGT LVTVSS            116

SEQ ID NO: 25           moltype = AA  length = 116
FEATURE                 Location/Qualifiers
REGION                  1..116
                        note = Synthetic
source                  1..116
                        mol_type = protein
                        organism = synthetic construct
SEQUENCE: 25
SEVQLVESGG GLVQPGNSLR LSCAASGFTF SSFGMSWVRQ APGKGLEWVS SISGSGSDTL         60
YADSVKGRFT ISRDNAKTTL YLQMNSLRPE DTAVYYCTIG GSLSRSSQGT LVTVSS            116

SEQ ID NO: 26           moltype = AA  length = 117
FEATURE                 Location/Qualifiers
REGION                  1..117
                        note = Synthetic
source                  1..117
                        mol_type = protein
                        organism = synthetic construct
SEQUENCE: 26
AGEVQLVESG GGLVQPGNSL RLSCAASGFT FSSFGMSWVR QAPGKGLEWV SSISGSGSDT         60
LYADSVKGRF TISRDNAKTT LYLQMNSLRP EDTAVYYCTI GGSLSRSSQG TLVTVSS           117

SEQ ID NO: 27           moltype = AA  length = 117
FEATURE                 Location/Qualifiers
REGION                  1..117
                        note = Synthetic
source                  1..117
                        mol_type = protein
                        organism = synthetic construct
SEQUENCE: 27
SGEVQLVESG GGLVQPGNSL RLSCAASGFT FSSFGMSWVR QAPGKGLEWV SSISGSGSDT         60
LYADSVKGRF TISRDNAKTT LYLQMNSLRP EDTAVYYCTI GGSLSRSSQG TLVTVSS           117

SEQ ID NO: 28           moltype = AA  length = 31
```

```
FEATURE              Location/Qualifiers
source               1..31
                     mol_type = protein
                     organism = Homo sapiens
SEQUENCE: 28
HAEGTFTSDV SSYLEGQAAK EFIAWLVKGR G                              31

SEQ ID NO: 29        moltype = AA  length = 31
FEATURE              Location/Qualifiers
REGION               1..31
                     note = Synthetic
source               1..31
                     mol_type = protein
                     organism = synthetic construct
SEQUENCE: 29
HGEGTFTSDV SSYLEEQAAK EFIAWLVKGG G                              31

SEQ ID NO: 30        moltype = AA  length = 29
FEATURE              Location/Qualifiers
REGION               1..29
                     note = Synthetic
source               1..29
                     mol_type = protein
                     organism = synthetic construct
SEQUENCE: 30
EGTFTSDVSS YLEEQAAKEF IAWLVKGGG                                 29

SEQ ID NO: 31        moltype = AA  length = 31
FEATURE              Location/Qualifiers
REGION               1..31
                     note = Synthetic
source               1..31
                     mol_type = protein
                     organism = synthetic construct
SEQUENCE: 31
HGEGTFTSDV SSYLEEQAAK EFIAWLVRGG G                              31

SEQ ID NO: 32        moltype = AA  length = 31
FEATURE              Location/Qualifiers
REGION               1..31
                     note = Synthetic
source               1..31
                     mol_type = protein
                     organism = synthetic construct
SEQUENCE: 32
HGEGTFTSDV SSYLEEQAAR EFIAWLVRGG G                              31

SEQ ID NO: 33        moltype = AA  length = 31
FEATURE              Location/Qualifiers
REGION               1..31
                     note = Synthetic
source               1..31
                     mol_type = protein
                     organism = synthetic construct
SEQUENCE: 33
HGEGTFTSDV SSYLEEQAAR EFIAWLVRGK G                              31

SEQ ID NO: 34        moltype = AA  length = 31
FEATURE              Location/Qualifiers
REGION               1..31
                     note = Synthetic
source               1..31
                     mol_type = protein
                     organism = synthetic construct
SEQUENCE: 34
HGEGTFTSDV SSYLEEQAAR EFIAWLVRGG G                              31

SEQ ID NO: 35        moltype = AA  length = 4
FEATURE              Location/Qualifiers
REGION               1..4
                     note = Synthetic
source               1..4
                     mol_type = protein
                     organism = synthetic construct
SEQUENCE: 35
GAQP                                                            4

SEQ ID NO: 36        moltype = AA  length = 4
FEATURE              Location/Qualifiers
```

```
REGION                    1..4
                          note = Synthetic
source                    1..4
                          mol_type = protein
                          organism = synthetic construct
SEQUENCE: 36
GQAP                                                                       4

SEQ ID NO: 37             moltype = AA  length = 4
FEATURE                   Location/Qualifiers
REGION                    1..4
                          note = Synthetic
source                    1..4
                          mol_type = protein
                          organism = synthetic construct
SEQUENCE: 37
GPAQ                                                                       4

SEQ ID NO: 38             moltype = AA  length = 4
FEATURE                   Location/Qualifiers
REGION                    1..4
                          note = Synthetic
source                    1..4
                          mol_type = protein
                          organism = synthetic construct
SEQUENCE: 38
GPQA                                                                       4

SEQ ID NO: 39             moltype = AA  length = 4
FEATURE                   Location/Qualifiers
REGION                    1..4
                          note = Synthetic
source                    1..4
                          mol_type = protein
                          organism = synthetic construct
SEQUENCE: 39
GSQP                                                                       4

SEQ ID NO: 40             moltype = AA  length = 4
FEATURE                   Location/Qualifiers
REGION                    1..4
                          note = Synthetic
source                    1..4
                          mol_type = protein
                          organism = synthetic construct
SEQUENCE: 40
GASP                                                                       4

SEQ ID NO: 41             moltype = AA  length = 4
FEATURE                   Location/Qualifiers
REGION                    1..4
                          note = Synthetic
source                    1..4
                          mol_type = protein
                          organism = synthetic construct
SEQUENCE: 41
GPAS                                                                       4

SEQ ID NO: 42             moltype = AA  length = 4
FEATURE                   Location/Qualifiers
REGION                    1..4
                          note = Synthetic
source                    1..4
                          mol_type = protein
                          organism = synthetic construct
SEQUENCE: 42
GPSA                                                                       4

SEQ ID NO: 43             moltype = AA  length = 4
FEATURE                   Location/Qualifiers
REGION                    1..4
                          note = Synthetic
source                    1..4
                          mol_type = protein
                          organism = synthetic construct
SEQUENCE: 43
GGGS                                                                       4

SEQ ID NO: 44             moltype = AA  length = 4
```

```
FEATURE                 Location/Qualifiers
REGION                  1..4
                        note = Synthetic
source                  1..4
                        mol_type = protein
                        organism = synthetic construct
SEQUENCE: 44
GSGS                                                                    4

SEQ ID NO: 45           moltype = AA  length = 5
FEATURE                 Location/Qualifiers
REGION                  1..5
                        note = Synthetic
source                  1..5
                        mol_type = protein
                        organism = synthetic construct
SEQUENCE: 45
GGGGS                                                                   5

SEQ ID NO: 46           moltype = AA  length = 20
FEATURE                 Location/Qualifiers
REGION                  1..20
                        note = Synthetic
source                  1..20
                        mol_type = protein
                        organism = synthetic construct
SEQUENCE: 46
GSAPGSPAGS PTGSAPGSPA                                                  20

SEQ ID NO: 47           moltype = AA  length = 20
FEATURE                 Location/Qualifiers
REGION                  1..20
                        note = Synthetic
source                  1..20
                        mol_type = protein
                        organism = synthetic construct
SEQUENCE: 47
GGGGSGGGGS GGGGSGGGGS                                                  20

SEQ ID NO: 48           moltype = AA  length = 9
FEATURE                 Location/Qualifiers
REGION                  1..9
                        note = Synthetic
source                  1..9
                        mol_type = protein
                        organism = synthetic construct
SEQUENCE: 48
GGGGSGGGS                                                               9

SEQ ID NO: 49           moltype = AA  length = 8
FEATURE                 Location/Qualifiers
REGION                  1..8
                        note = Synthetic
source                  1..8
                        mol_type = protein
                        organism = synthetic construct
SEQUENCE: 49
GAQPGAQP                                                                8

SEQ ID NO: 50           moltype = AA  length = 20
FEATURE                 Location/Qualifiers
REGION                  1..20
                        note = Synthetic
source                  1..20
                        mol_type = protein
                        organism = synthetic construct
SEQUENCE: 50
GAQPGAQPGA QPGAQPGAQP                                                  20

SEQ ID NO: 51           moltype = AA  length = 40
FEATURE                 Location/Qualifiers
REGION                  1..40
                        note = Synthetic
source                  1..40
                        mol_type = protein
                        organism = synthetic construct
SEQUENCE: 51
GAQPGAQPGA QPGAQPGAQP GAQPGAQPGA QPGAQPGAQP                            40
```

```
SEQ ID NO: 52              moltype = AA   length = 56
FEATURE                    Location/Qualifiers
REGION                     1..56
                           note = Synthetic
source                     1..56
                           mol_type = protein
                           organism = synthetic construct
SEQUENCE: 52
GAQPGAQPGA QPGAQPGAQP GAQPGAQPGA QPGAQPGAQP GAQPGAQPGA QPGAQP         56

SEQ ID NO: 53              moltype = AA   length = 48
FEATURE                    Location/Qualifiers
REGION                     1..48
                           note = Synthetic
source                     1..48
                           mol_type = protein
                           organism = synthetic construct
SEQUENCE: 53
GQEPGAQPGQ EPGAQPGQEP GAQPGQEPGA QPGQEPGAQP GQEPGAQP                  48

SEQ ID NO: 54              moltype = AA   length = 15
FEATURE                    Location/Qualifiers
REGION                     1..15
                           note = Synthetic
source                     1..15
                           mol_type = protein
                           organism = synthetic construct
SEQUENCE: 54
GGGGGSGGGS GGGGS                                                      15

SEQ ID NO: 55              moltype = AA   length = 4
FEATURE                    Location/Qualifiers
REGION                     1..4
                           note = Synthetic
source                     1..4
                           mol_type = protein
                           organism = synthetic construct
SEQUENCE: 55
GQEP                                                                   4

SEQ ID NO: 56              moltype = AA   length = 4
FEATURE                    Location/Qualifiers
REGION                     1..4
                           note = Synthetic
source                     1..4
                           mol_type = protein
                           organism = synthetic construct
SEQUENCE: 56
GEQP                                                                   4

SEQ ID NO: 57              moltype = AA   length = 4
FEATURE                    Location/Qualifiers
REGION                     1..4
                           note = Synthetic
source                     1..4
                           mol_type = protein
                           organism = synthetic construct
SEQUENCE: 57
GPQE                                                                   4

SEQ ID NO: 58              moltype = AA   length = 4
FEATURE                    Location/Qualifiers
REGION                     1..4
                           note = Synthetic
source                     1..4
                           mol_type = protein
                           organism = synthetic construct
SEQUENCE: 58
GPEQ                                                                   4

SEQ ID NO: 59              moltype = AA   length = 4
FEATURE                    Location/Qualifiers
REGION                     1..4
                           note = Synthetic
source                     1..4
                           mol_type = protein
                           organism = synthetic construct
SEQUENCE: 59
GSEP                                                                   4
```

```
SEQ ID NO: 60            moltype = AA   length = 4
FEATURE                  Location/Qualifiers
REGION                   1..4
                         note = Synthetic
source                   1..4
                         mol_type = protein
                         organism = synthetic construct
SEQUENCE: 60
GESP                                                                       4

SEQ ID NO: 61            moltype = AA   length = 4
FEATURE                  Location/Qualifiers
REGION                   1..4
                         note = Synthetic
source                   1..4
                         mol_type = protein
                         organism = synthetic construct
SEQUENCE: 61
GPSE                                                                       4

SEQ ID NO: 62            moltype = AA   length = 4
FEATURE                  Location/Qualifiers
REGION                   1..4
                         note = Synthetic
source                   1..4
                         mol_type = protein
                         organism = synthetic construct
SEQUENCE: 62
GPES                                                                       4

SEQ ID NO: 63            moltype = AA   length = 338
FEATURE                  Location/Qualifiers
REGION                   1..338
                         note = Synthetic
source                   1..338
                         mol_type = protein
                         organism = synthetic construct
SEQUENCE: 63
SGEVQLVESG GGLVQPGNSL RLSCAASGFT FSSFGMSWVR QAPGKGLEWV SSISGSGSDT           60
LYADSVKGRF TISRDNAKTT LYLQMNSLRP EDTAVYYCTI GGSLSRSSQG TLVTVSSGAQ          120
PGAQPGAQPG AQPGAQPGAQ PGAQPGAQPG AQPGAQPHPI PDSSPLLQFG GQVRQRYLYT          180
DDAQQTEAHL EIREDGTVGG AADQSPESLL QLKALKPGVI QILGVKTSRF LCQRPDGALY          240
GSLHFDPEAC SFRELLLEDG YNVYQSEAHG LPLHLPGQKS PHRDPAPRGP ARFLPLPGLP          300
PALPEPPGIL APQPPDVGSS DPLSLVGCSQ GRSPSYES                                  338

SEQ ID NO: 64            moltype = AA   length = 338
FEATURE                  Location/Qualifiers
REGION                   1..338
                         note = Synthetic
source                   1..338
                         mol_type = protein
                         organism = synthetic construct
SEQUENCE: 64
SGEVQLVESG GGLVQPGNSL RLSCAASGFT FSSFGMSWVR QAPGKGLEWV SSISGSGSDT           60
LYADSVKGRF TISRDNAKTT LYLQMNSLRP EDTAVYYCTI GGSLSRSSQG TLVTVSSGAQ          120
PGAQPGAQPG AQPGAQPGAQ PGAQPGAQPG AQPGAQPHPI PDSSPLLQFG GQVRQRYLYT          180
DDAQQTEAHL EIREDGTVGG AADQSPESLL QLKALKPGVI QILGVKTSRF LCQRPDGALY          240
GSLHFDPEAC SFRELLLEDG YNVYQSEAHG LPLHLPGQKS PHRDPAPRGP ARFLPLPGLP          300
PALPEPPGIL APQPPDVGSS DPLSLVGGSQ GRSPSYES                                  338

SEQ ID NO: 65            moltype = AA   length = 318
FEATURE                  Location/Qualifiers
REGION                   1..318
                         note = Synthetic
source                   1..318
                         mol_type = protein
                         organism = synthetic construct
SEQUENCE: 65
SGEVQLVESG GGLVQPGNSL RLSCAASGFT FSSFGMSWVR QAPGKGLEWV SSISGSGSDT           60
LYADSVKGRF TISRDNAKTT LYLQMNSLRP EDTAVYYCTI GGSLSRSSQG TLVTVSSGAQ          120
PGAQPGAQPG AQPGAQPHPI PDSSPLLQFG GQVRQRYLYT DDAQQTEAHL EIREDGTVGG          180
AADQSPESLL QLKALKPGVI QILGVKTSRF LCQRPDGALY GSLHFDPEAC SFRELLLEDG          240
YNVYQSEAHG LPLHLPGQKS PHRDPAPRGP ARFLPLPGLP PALPEPPGIL APQPPDVGSS          300
DPLSLVGGSQ GRSPSYES                                                        318

SEQ ID NO: 66            moltype = AA   length = 306
FEATURE                  Location/Qualifiers
REGION                   1..306
```

```
                             note = Synthetic
source                       1..306
                             mol_type = protein
                             organism = synthetic construct
SEQUENCE: 66
SGEVQLVESG GGLVQPGNSL RLSCAASGFT FSSFGMSWVR QAPGKGLEWV SSISGSGSDT   60
LYADSVKGRF TISRDNAKTT LYLQMNSLRP EDTAVYYCTI GGSLSRSSQG TLVTVSSGAQ  120
PGAQPHPIPD SSPLLQFGGQ VRQRYLYTDD AQQTEAHLEI REDGTVGGAA DQSPESLLQL  180
KALKPGVIQI LGVKTSRFLC QRPDGALYGS LHFDPEACSF RELLLEDGYN VYQSEAHGLP  240
LHLPGQKSPH RDPAPRGPAR FLPLPGLPPA LPEPPGILAP QPPDVGSSDP LSLVGGSQGR  300
SPSYES                                                            306

SEQ ID NO: 67                moltype = AA  length = 302
FEATURE                      Location/Qualifiers
REGION                       1..302
                             note = Synthetic
source                       1..302
                             mol_type = protein
                             organism = synthetic construct
SEQUENCE: 67
SGEVQLVESG GGLVQPGNSL RLSCAASGFT FSSFGMSWVR QAPGKGLEWV SSISGSGSDT   60
LYADSVKGRF TISRDNAKTT LYLQMNSLRP EDTAVYYCTI GGSLSRSSQG TLVTVSSGAQ  120
PHPIPDSSPL LQFGGQVRQR YLYTDDAQQT EAHLEIREDG TVGGAADQSP ESLLQLKALK  180
PGVIQILGVK TSRFLCQRPD GALYGSLHFD PEACSFRELL LEDGYNVYQS EAHGLPLHLP  240
GQKSPHRDPA PRGPARFLPL PGLPPALPEP PGILAPQPPD VGSSDPLSLV GGSQGRSPSY  300
ES                                                                302

SEQ ID NO: 68                moltype = AA  length = 302
FEATURE                      Location/Qualifiers
REGION                       1..302
                             note = Synthetic
source                       1..302
                             mol_type = protein
                             organism = synthetic construct
SEQUENCE: 68
SGEVQLVESG GGLVQPGNSL RLSCAASGFT FSSFGMSWVR QAPGKGLEWV SSISGSGSDT   60
LYADSVKGRF TISRDNAKTT LYLQMNSLRP EDTAVYYCTI GGSLSRSSQG TLVTVSSGAQ  120
PHPIPDSSPL LQFGGQVRQR YLYTDDAQQT EAHLEIREDG TVGGAADQSP ESLLQLKALK  180
PGVIQILGVK TSRFLCQRPD GALYGSLHFD PEACSFRELL LEDGYNVYQS EAHGLPLHLP  240
GQKSPHRDPA PRGPARFLPL PGLPPALPEP PGILAPQPPD VGSSDPLSLV GCSQGRSPSY  300
ES                                                                302

SEQ ID NO: 69                moltype = AA  length = 424
FEATURE                      Location/Qualifiers
REGION                       1..424
                             note = Synthetic
source                       1..424
                             mol_type = protein
                             organism = synthetic construct
SEQUENCE: 69
MDKTHTCPPC PAPELLGGPS VFLFPPKPKD TLMISRTPEV TCVVVDVSHE DPEVKFNWYV   60
DGVEVHNAKT KPREEQYNST YRVVSVLTVL HQDWLNGKEY KCKVSNKALP APIEKTISKA  120
KGQPREPQVY TLPPSRDELT KNQVSLTCLV KGFYPSDIAV EWESNGQPEN NYKTTPPVLD  180
SDGSFFLYSK LTVDKSRWQQ GNVFSCSVMH EALHNHYTQK SLSLSPGKGG GGGSGGGGSG  240
GGSHPIPDSS PLLQFGGQVR QRYLYTDDAQ QTEAHLEIRE DGTVGGAADQ SPESLLQLKA  300
LKPGVIQILG VKTSRFLCQR PDGALYGSLH FDPEACSFRE LLEDGYNVY QSEAHGLPLH  360
LPGNKSPHRD PAPRGPARFL PLPGLPPAPP EPPGILAPQP PDVGSSDPLS MVGGSQGRSP  420
SYES                                                              424

SEQ ID NO: 70                moltype = AA  length = 356
FEATURE                      Location/Qualifiers
REGION                       1..356
                             note = Synthetic
source                       1..356
                             mol_type = protein
                             organism = synthetic construct
SEQUENCE: 70
HGEGTFTSDV SSYLEEQAAK EFIAWLVKGG GGGGSGGGG SGGGGSGGGG SEVQLVESGG   60
GLVQPGNSLR LSCAASGFTF SSFGMSWVRQ APGKGLEWVS SISGSGSDTL YADSVKGRFT  120
ISRDNAKTTL YLQMNSLRPE DTAVYYCTIG GSLSRSSQGT LVTVSSGGGG SGGGSHPIPD  180
SSPLLQFGGQ VRQRYLYTDD AQQTEAHLEI REDGTVGGAA DQSPESLLQL KALKPGVIQI  240
LGVKTSRFLC QRPDGALYGS LHFDPEACSF RELLLEDGYN VYQSEAHGLP LHLPGQKSPH  300
RDPAPRGPAR FLPLPGLPPA LPEPPGILAP QPPDVGSSDP LSLVGGSQGR SPSYES      356

SEQ ID NO: 71                moltype = AA  length = 354
FEATURE                      Location/Qualifiers
REGION                       1..354
                             note = Synthetic
source                       1..354
```

```
                            mol_type = protein
                            organism = synthetic construct
SEQUENCE: 71
EGTFTSDVSS YLEEQAAKEF IAWLVKGGGG GGGSGGGGSG GGGSGGGGSE VQLVESGGGL   60
VQPGNSLRLS CAASGFTFSS FGMSWVRQAP GKGLEWVSSI SGSGSDTLYA DSVKGRFTIS  120
RDNAKTTLYL QMNSLRPEDT AVYYCTIGGS LSRSSQGTLV TVSSGGGSG GGSHPIPDSS   180
PLLQFGGQVR QRYLYTDDAQ QTEAHLEIRE DGTVGGAADQ SPESLLQLKA LKPGVIQILG  240
VKTSRFLCQR PDGALYGSLH FDPEACSFRE LLLEDGYNVY QSEAHGLPLH LPGQKSPHRD  300
PAPRGPARFL PLPGLPPALP EPPGILAPQP PDVGSSDPLS LVGGSQGRSP SYES        354

SEQ ID NO: 72              moltype = AA  length = 385
FEATURE                    Location/Qualifiers
REGION                     1..385
                           note = Synthetic
source                     1..385
                           mol_type = protein
                           organism = synthetic construct
SEQUENCE: 72
EGTFTSDVSS YLEEQAAKEF IAWLVKGGGG AQPGAQPGAQ PGAQPGAQPE VQLVESGGGL   60
VQPGNSLRLS CAASGFTFSS FGMSWVRQAP GKGLEWVSSI SGSGSDTLYA DSVKGRFTIS  120
RDNAKTTLYL QMNSLRPEDT AVYYCTIGGS LSRSSQGTLV TVSSGAQPGA QPGAQPGAQP  180
GAQPGAQPGA QPGAQPGAQP GAQPHPIPDS PLLQFGGQVR QRYLYTDDA QQTEAHLEIR   240
EDGTVGGAAD QSPESLLQLK ALKPGVIQIL GVKTSRFLCQ RPDGALYGSL HFDPEACSFR  300
ELLLEDGYNV YQSEAHGLPL HLPGQKSPHR DPAPRGPARF LPLPGLPPAL PEPPGILAPQ  360
PPDVGSSDPL SLVGGSQGRS PSYES                                       385

SEQ ID NO: 73              moltype = AA  length = 393
FEATURE                    Location/Qualifiers
REGION                     1..393
                           note = Synthetic
source                     1..393
                           mol_type = protein
                           organism = synthetic construct
SEQUENCE: 73
EGTFTSDVSS YLEEQAAKEF IAWLVKGGGG AQPGAQPGAQ PGAQPGAQPE VQLVESGGGL   60
VQPGNSLRLS CAASGFTFSS FGMSWVRQAP GKGLEWVSSI SGSGSDTLYA DSVKGRFTIS  120
RDNAKTTLYL QMNSLRPEDT AVYYCTIGGS LSRSSQGTLV TVSSGQEPGA QPGQEPGAQP  180
GQEPGAQPGQ EPGAQPGAQP GQEPGAQPGE PGAQPGQEPGA QPHPIPDSSP LLQFGGQVRQ  240
RYLYTDDAQQ TEAHLEIRED GTVGGAADQS PESLLQLKAL KPGVIQILGV KTSRFLCQRP  300
DGALYGSLHF DPEACSFREL LLEDGYNVYQ SEAHGLPLHL PGQKSPHRDP APRGPARFLP  360
LPGLPPALPE PPGILAPQPP DVGSSDPLSL VGGSQGRSPS YES                    393

SEQ ID NO: 74              moltype = AA  length = 387
FEATURE                    Location/Qualifiers
REGION                     1..387
                           note = Synthetic
source                     1..387
                           mol_type = protein
                           organism = synthetic construct
SEQUENCE: 74
HGEGTFTSDV SSYLEEQAAK EFIAWLVKGG GGAQPGAQPG AQPGAQPGAQ PEVQLVESGG   60
GLVQPGNSLR LSCAASGFTF SSFGMSWVRQ APGKGLEWVS SISGSGSDTL YADSVKGRFT  120
ISRDNAKTTL YLQMNSLRPE DTAVYYCTIG GSLSRSSQGT LVTVSSGAQP GAQPGAQPGA  180
QPGAQPGAQP GAQPGAQPGA QPGAQPHPIP DSSPLLQFGG QVRQRYLYTD DAQQTEAHLE  240
IREDGTVGGA ADQSPESLLQ LKALKPGVIQ ILGVKTSRFL CQRPDGALYG SLHFDPEACS  300
FRELLLEDGY NVYQSEAHGL PLHLPGQKSP HRDPAPRGPA RFLPLPGLPP ALPEPPGILA  360
PQPPDVGSSD PLSLVGCSQG RSPSYES                                     387

SEQ ID NO: 75              moltype = AA  length = 387
FEATURE                    Location/Qualifiers
REGION                     1..387
                           note = Synthetic
source                     1..387
                           mol_type = protein
                           organism = synthetic construct
SEQUENCE: 75
HGEGTFTSDV SSYLEEQAAK EFIAWLVKGG GGAQPGAQPG AQPGAQPGAQ PEVQLVESGG   60
GLVQPGNSLR LSCAASGFTF SSFGMSWVRQ APGKGLEWVS SISGSGSDTL YADSVKGRFT  120
ISRDNAKTTL YLQMNSLRPE DTAVYYCTIG GSLSRSSQGT LVTVSSGAQP GAQPGAQPGA  180
QPGAQPGAQP GAQPGAQPGA QPGAQPHPIP DSSPLLQFGG QVRQRYLYTD DAQQTEAHLE  240
IREDGTVGGA ADQSPESLLQ LKALKPGVIQ ILGVKTSRFL CQRPDGALYG SLHFDPEACS  300
FRELLLEDGY NVYQSEAHGL PLHLPGQKSP HRDPAPRGPA RFLPLPGLPP ALPEPPGILA  360
PQPPDVGSSD PLSLVGGSQG RSPSYES                                     387

SEQ ID NO: 76              moltype = AA  length = 365
FEATURE                    Location/Qualifiers
REGION                     1..365
                           note = Synthetic
source                     1..365
```

```
                        mol_type = protein
                        organism = synthetic construct
SEQUENCE: 76
EGTFTSDVSS YLEEQAAKEF IAWLVKGGGG AQPGAQPGAQ PGAQPGAQPE VQLVESGGGL      60
VQPGNSLRLS CAASGFTFSS FGMSWVRQAP GKGLEWVSSI SGSGSDTLYA DSVKGRFTIS     120
RDNAKTTLYL QMNSLRPEDT AVYYCTIGGS LSRSSQGTLV TVSSGAQPGA QPGAQPGAQP     180
GAQPHPIPDS SPLLQFGGQV RQRYLYTDDA QQTEAHLEIR EDGTVGGAAD QSPESLLQLK     240
ALKPGVIQIL GVKTSRFLCQ RPDGALYGSL HFDPEACSFR ELLLEDGYNV YQSEAHGLPL     300
HLPGQKSPHR DPAPRGPARF LPLPGLPPAL PEPPGILAPQ PPDVGSSDPL SLVGGSQGRS     360
PSYES                                                                 365

SEQ ID NO: 77           moltype = AA  length = 353
FEATURE                 Location/Qualifiers
REGION                  1..353
                        note = Synthetic
source                  1..353
                        mol_type = protein
                        organism = synthetic construct
SEQUENCE: 77
EGTFTSDVSS YLEEQAAKEF IAWLVKGGGG AQPGAQPGAQ PGAQPGAQPE VQLVESGGGL      60
VQPGNSLRLS CAASGFTFSS FGMSWVRQAP GKGLEWVSSI SGSGSDTLYA DSVKGRFTIS     120
RDNAKTTLYL QMNSLRPEDT AVYYCTIGGS LSRSSQGTLV TVSSGAQPGA QPGAQPGAQP     180
LLQFGGQVRQ RYLYTDDAQQ TEAHLEIRED GTVGGAADQS PESLLQLKAL KPGVIQILGV     240
KTSRFLCQRP DGALYGSLHF DPEACSFREL LLEDGYNVYQ SEAHGLPLHL PGQKSPHRDP     300
APRGPARFLP LPGLPPALPE PPGILAPQPP DVGSSDPLSL VGGSQGRSPS YES            353

SEQ ID NO: 78           moltype = AA  length = 349
FEATURE                 Location/Qualifiers
REGION                  1..349
                        note = Synthetic
source                  1..349
                        mol_type = protein
                        organism = synthetic construct
SEQUENCE: 78
EGTFTSDVSS YLEEQAAKEF IAWLVKGGGG AQPGAQPGAQ PGAQPGAQPE VQLVESGGGL      60
VQPGNSLRLS CAASGFTFSS FGMSWVRQAP GKGLEWVSSI SGSGSDTLYA DSVKGRFTIS     120
RDNAKTTLYL QMNSLRPEDT AVYYCTIGGS LSRSSQGTLV TVSSGAQPHP IPDSSPLLQF     180
GGQVRQRYLY TDDAQQTEAH LEIREDGTVG GAADQSPESL LQLKALKPGV IQILGVKTSR     240
FLCQRPDGAL YGSLHFDPEA CSFRELLLED GYNVYQSEAH GLPLHLPGQK SPHRDPAPRG     300
PARFLPLPGL PPALPEPPGI LAPQPPDVGS SDPLSLVGGS QGRSPSYES                 349

SEQ ID NO: 79           moltype = AA  length = 407
FEATURE                 Location/Qualifiers
REGION                  1..407
                        note = Synthetic
source                  1..407
                        mol_type = protein
                        organism = synthetic construct
SEQUENCE: 79
HGEGTFTSDV SSYLEEQAAK EFIAWLVKGG GGAQPGAQPG AQPGAQPGAQ PGAQPGAQPG      60
AQPGAQPGAQ PEVQLVESGG GLVQPGNSLR LSCAASGFTF SSFGMSWVRQ APGKGLEWVS     120
SISGSGSDTL YADSVKGRFT ISRDNAKTTL YLQMNSLRPE DTAVYYCTIG GSLSRSSQGT     180
LVTVSSGAQP GAQPGAQPGA QPGAQPGAQP GAQPGAQPGA QPGAQPHPIP DSSPLLQFGG     240
QVRQRYLYTD DAQQTEAHLE IREDGTVGGA ADQSPESLLQ LKALKPGVIQ ILGVKTSRFL     300
CQRPDGALYG SLHFDPEACS FRELLLEDGY NVYQSEAHGL PLHLPGQKSP HRDPAPRGPA     360
RFLPLPGLPP ALPEPPGILA PQPPDVGSSD PLSLVGGSQG RSPSYES                   407

SEQ ID NO: 80           moltype = AA  length = 351
FEATURE                 Location/Qualifiers
REGION                  1..351
                        note = Synthetic
source                  1..351
                        mol_type = protein
                        organism = synthetic construct
SEQUENCE: 80
HGEGTFTSDV SSYLEEQAAK EFIAWLVKGG GGAQPGAQPG AQPGAQPGAQ PEVQLVESGG      60
GLVQPGNSLR LSCAASGFTF SSFGMSWVRQ APGKGLEWVS SISGSGSDTL YADSVKGRFT     120
ISRDNAKTTL YLQMNSLRPE DTAVYYCTIG GSLSRSSQGT LVTVSSGAQP HPIPDSSPLL     180
QFGGQVRQRY LYTDDAQQTE AHLEIREDGT VGGAADQSPE SLLQLKALKP GVIQILGVKT     240
SRFLCQRPDG ALYGSLHFDP EACSFRELLL EDGYNVYQSE AHGLPLHLPG QKSPHRDPAP     300
RGPARFLPLP GLPPALPEPP GILAPQPPDV GSSDPLSLVG GSQGRSPSYE S               351

SEQ ID NO: 81           moltype = AA  length = 351
FEATURE                 Location/Qualifiers
REGION                  1..351
                        note = Synthetic
source                  1..351
                        mol_type = protein
                        organism = synthetic construct
```

```
SEQUENCE: 81
HGEGTFTSDV SSYLEEQAAK EFIAWLVKGG GGAQPGAQPG AQPGAQPGAQ PEVQLVESGG    60
GLVQPGNSLR LSCAASGFTF SSFGMSWVRQ APGKGLEWVS SISGSGSDTL YADSVKGRFT   120
ISRDNAKTTL YLQMNSLRPE DTAVYYCTIG GSLSRSSQGT LVTVSSGAQP HPIPDSSPLL   180
QFGGQVRQRY LYTDDAQQTE AHLEIREDGT VGGAADQSPE SLLQLKALKP GVIQILGVKT   240
SRFLCQRPDG ALYGSLHFDP EACSFRELLL EDGYNVYQSE AHGLPLHLPG QKSPHRDPAP   300
RGPARFLPLP GLPPALPEPP GILAPQPPDV GSSDPLSLVG CSQGRSPSYE S            351

SEQ ID NO: 82           moltype = AA  length = 371
FEATURE                 Location/Qualifiers
REGION                  1..371
                        note = Synthetic
source                  1..371
                        mol_type = protein
                        organism = synthetic construct
SEQUENCE: 82
HGEGTFTSDV SSYLEEQAAK EFIAWLVKGG GGAQPGAQPG AQPGAQPGAQ PGAQPGAQPG    60
AQPGAQPGAQ PEVQLVESGG GLVQPGNSLR LSCAASGFTF SSFGMSWVRQ APGKGLEWVS   120
SISGSGSDTL YADSVKGRFT ISRDNAKTTL YLQMNSLRPE DTAVYYCTIG GSLSRSSQGT   180
LVTVSSGAQP HPIPDSSPLL QFGGQVRQRY LYTDDAQQTE AHLEIREDGT VGGAADQSPE   240
SLLQLKALKP GVIQILGVKT SRFLCQRPDG ALYGSLHFDP EACSFRELLL EDGYNVYQSE   300
AHGLPLHLPG QKSPHRDPAP RGPARFLPLP GLPPALPEPP GILAPQPPDV GSSDPLSLVG   360
CSQGRSPSYE S                                                        371

SEQ ID NO: 83           moltype = AA  length = 339
FEATURE                 Location/Qualifiers
REGION                  1..339
                        note = Synthetic
source                  1..339
                        mol_type = protein
                        organism = synthetic construct
SEQUENCE: 83
HGEGTFTSDV SSYLEEQAAK EFIAWLVKGG GGAQPGAQPE VQLVESGGGL VQPGNSLRLS    60
CAASGFTFSS FGMSWVRQAP GKGLEWVSSI SGSGSDTLYA DSVKGRFTIS RDNAKTTLYL   120
QMNSLRPEDT AVYYCTIGGS LSRSSQGTLV TVSSGAQPHP IPDSSPLLQF GGQVRQRYLY   180
TDDAQQTEAH LEIREDGTVG GAADQSPESL LQLKALKPGV IQILGVKTSR FLCQRPDGAL   240
YGSLHFDPEA CSFRELLLED GYNVYQSEAH GLPLHLPGQK SPHRDPAPRG PARFLPLPGL   300
PPALPEPPGI LAPQPPDVGS SDPLSLVGCS QGRSPSYES                          339

SEQ ID NO: 84           moltype = AA  length = 345
FEATURE                 Location/Qualifiers
REGION                  1..345
                        note = Synthetic
source                  1..345
                        mol_type = protein
                        organism = synthetic construct
SEQUENCE: 84
EGTFTSDVSS YLEEQAAKEF IAWLVKGGGG AQPGAQPGAQ PGAQPGAQPE VQLVESGGGL    60
VQPGNSLRLS CAASGFTFSS FGMSWVRQAP GKGLEWVSSI SGSGSDTLYA DSVKGRFTIS   120
RDNAKTTLYL QMNSLRPEDT AVYYCTIGGS LSRSSQGTLV TVSSHPIPDS SPLLQFGGQV   180
RQRYLYTDDA QQTEAHLEIR EDGTVGGAAD QSPESLLQLK ALKPGVIQIL GVKTSRFLCQ   240
RPDGALYGSL HFDPEACSFR ELLLEDGYNV YQSEAHGLPL HLPGQKSPHR DPAPRGPARF   300
LPLPGLPPAL PEPPGILAPQ PPDVGSSDPL SLVGGSQGRS PSYES                   345

SEQ ID NO: 85           moltype = AA  length = 387
FEATURE                 Location/Qualifiers
REGION                  1..387
                        note = Synthetic
source                  1..387
                        mol_type = protein
                        organism = synthetic construct
SEQUENCE: 85
HGEGTFTSDV SSYLEEQAAK EFIAWLVKGG GGAQPGAQPG AQPGAQPGAQ PGAQPGAQPG    60
AQPGAQPGAQ PGAQPGAQPG AQPGAQPEVQ LVESGGGLVQ PGNSLRLSCA ASGFTFSSFG   120
MSWVRQAPGK GLEWVSSISG SGSDTLYADS VKGRFTISRD NAKTTLYLQM NSLRPEDTAV   180
YYCTIGGSLS RSSQGTLVTV SSGAQPHPIP DSSPLLQFGG QVRQRYLYTD DAQQTEAHLE   240
IREDGTVGGA ADQSPESLLQ LKALKPGVIQ ILGVKTSRFL CQRPDGALYG SLHFDPEACS   300
FRELLLEDGY NVYQSEAHGL PLHLPGQKSP HRDPAPRGPA RFLPLPGLPP ALPEPPGILA   360
PQPPDVGSSD PLSLVGCSQG RSPSYES                                       387

SEQ ID NO: 86           moltype = AA  length = 385
FEATURE                 Location/Qualifiers
REGION                  1..385
                        note = Synthetic
source                  1..385
                        mol_type = protein
                        organism = synthetic construct
SEQUENCE: 86
EGTFTSDVSS YLEEQAAKEF IAWLVKGGGG AQPGAQPGAQ PGAQPGAQPG AQPGAQPGAQ    60
```

```
PGAQPGAQPG AQPGAQPGAQ PGAQPEVQLV ESGGGLVQPG NSLRLSCAAS GFTFSSFGMS    120
WVRQAPGKGL EWVSSISGSG SDTLYADSVK GRFTISRDNA KTTLYLQMNS LRPEDTAVYY    180
CTIGGSLSRS SQGTLVTVSS GAQPHPIPDS SPLLQFGGQV RQRYLYTDDA QQTEAHLEIR    240
EDGTVGGAAD QSPESLLQLK ALKPGVIQIL GVKTSRFLCQ RPDGALYGSL HFDPEACSFR    300
ELLLEDGYNV YQSEAHGLPL HLPGQKSPHR DPAPRGPARF LPLPGLPPAL PEPPGILAPQ    360
PPDVGSSDPL SLVGCSQGRS PSYES                                         385

SEQ ID NO: 87           moltype = AA   length = 387
FEATURE                 Location/Qualifiers
REGION                  1..387
                        note = Synthetic
source                  1..387
                        mol_type = protein
                        organism = synthetic construct
SEQUENCE: 87
HGEGTFTSDV SSYLEEQAAK EFIAWLVKGG GGAQPGAQPG AQPGAQPGAQ PGAQPGAQPG     60
AQPGAQPGAQ PGAQPGAQPG AQPGAQPEVQ LVESGGGLVQ PGNSLRLSCA ASGFTFSSFG    120
MSWVRQAPGK GLEWVSSISG SGSDTLYADS VKGRFTISRD NAKTTLYLQM NSLRPEDTAV    180
YYCTIGGSLS RSSQGTLVTV SSGAQPHPIP DSSPLLQFGG QVRQRYLYTD DAQQTEAHLE    240
IREDGTVGGA ADQSPESLLQ LKALKPGVIQ ILGVKTSRFL CQRPDGALYG SLHFDPEACS    300
FRELLLEDGY NVYQSEAHGL PLHLPGQKSP HRDPAPRGPA RFPPLPGLPP ALPEPPGILA    360
PQPPDVGSSD PLSLVGCSQG RSPSYES                                       387

SEQ ID NO: 88           moltype = AA   length = 385
FEATURE                 Location/Qualifiers
REGION                  1..385
                        note = Synthetic
source                  1..385
                        mol_type = protein
                        organism = synthetic construct
SEQUENCE: 88
EGTFTSDVSS YLEEQAAKEF IAWLVKGGGG AQPGAQPGAQ PGAQPGAQPG AQPGAQPGAQ     60
PGAQPGAQPG AQPGAQPGAQ PGAQPEVQLV ESGGGLVQPG NSLRLSCAAS GFTFSSFGMS    120
WVRQAPGKGL EWVSSISGSG SDTLYADSVK GRFTISRDNA KTTLYLQMNS LRPEDTAVYY    180
CTIGGSLSRS SQGTLVTVSS GAQPHPIPDS SPLLQFGGQV RQRYLYTDDA QQTEAHLEIR    240
EDGTVGGAAD QSPESLLQLK ALKPGVIQIL GVKTSRFLCQ RPDGALYGSL HFDPEACSFR    300
ELLLEDGYNV YQSEAHGLPL HLPGQKSPHR DPAPRGPARF PPLPGLPPAL PEPPGILAPQ    360
PPDVGSSDPL SLVGCSQGRS PSYES                                         385

SEQ ID NO: 89           moltype = AA   length = 181
FEATURE                 Location/Qualifiers
REGION                  1..181
                        note = Synthetic
source                  1..181
                        mol_type = protein
                        organism = synthetic construct
SEQUENCE: 89
HPIPDSSPLL QFGGQVRQRY LYTDDAQQTE AHLEIREDGT VGGAADQSPE SLLQLKALKP     60
GVIQILGVKT SRFLCQRPDG ALYGSLHFDP EACSFRELLL EDGYNVYQSE AHGLPLHLPG    120
QKSPHRDPAP RGPARFLPLP GLPPALPEPP GILAPQPPDV GSSDPLSLVG PSQGRSPSYA    180
S                                                                   181

SEQ ID NO: 90           moltype = AA   length = 181
FEATURE                 Location/Qualifiers
REGION                  1..181
                        note = Synthetic
source                  1..181
                        mol_type = protein
                        organism = synthetic construct
SEQUENCE: 90
HPIPDSSPLL QFGGQVRQRY LYTDDAQQTE AHLEIREDGT VGGAADQSPE SLLQLKALKP     60
GVIQILGVKT SRFLCQRPDG ALYGSLHFDP EACSFRELLL EDGYNVYQSE AHGLPLHLPG    120
QKSPHRDPAP RGPARFLPLP GLPPALPEPP GILAPQPPDV GSSDPLSMVG PSQGRSPSYE    180
S                                                                   181

SEQ ID NO: 91           moltype = AA   length = 181
FEATURE                 Location/Qualifiers
REGION                  1..181
                        note = Synthetic
source                  1..181
                        mol_type = protein
                        organism = synthetic construct
SEQUENCE: 91
HPIPDSSPLL QFGGQVRQRY LYTDDAQQTE AHLEIREDGT VGGAADQSPE SLLQLKALKP     60
GVIQILGVKT SRFLCQRPDG ALYGSLHFDP EACSFRELLL EDGYNVYQSE AHGLPLHLPG    120
NKSPHRDPAP RGPARFLPLP GLPPALPEPP GILAPQPPDV GSSDPLSLVG PSQGRSPSYE    180
S                                                                   181

SEQ ID NO: 92           moltype = AA   length = 181
```

```
FEATURE                 Location/Qualifiers
REGION                  1..181
                        note = Synthetic
source                  1..181
                        mol_type = protein
                        organism = synthetic construct
SEQUENCE: 92
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVG GSQCRSPSYE   180
S                                                                   181

SEQ ID NO: 93           moltype = AA  length = 302
FEATURE                 Location/Qualifiers
REGION                  1..302
                        note = Synthetic
source                  1..302
                        mol_type = protein
                        organism = synthetic construct
SEQUENCE: 93
SGEVQLVESG GGLVQPGNSL RLSCAASGFT FSSFGMSWVR QAPGKGLEWV SSISGSGSDT    60
LYADSVKGRF TISRDNAKTT LYLQMNSLRP EDTAVYYCTI GGSLSRSSQG TLVTVSSGAQ   120
PHPIPDSSPL LQFGGQVRQR YLYTDDAQQT EAHLEIREDG TVGGAADQSP ESLLQLKALK   180
PGVIQILGVK TSRFLCQRPD GALYGSLHFD PEACSFRELL LEDGYNVYQS EAHGLPLHLP   240
GQKSPHRDPA PRGPARFLPL PGLPPALPEP PGILAPQPPD VGSSDPLSLV GGSQCRSPSY   300
ES                                                                  302

SEQ ID NO: 94           moltype = AA  length = 387
FEATURE                 Location/Qualifiers
REGION                  1..387
                        note = Synthetic
source                  1..387
                        mol_type = protein
                        organism = synthetic construct
SEQUENCE: 94
HGEGTFTSDV SSYLEEQAAK EFIAWLVKGG GGAQPGAQPG AQPGAQPGAQ PGAQPGAQPG    60
AQPGAQPGAQ PGAQPGAQPG AQPGAQPEVQ LVESGGGLVQ PGNSLRLSCA ASGFTFSSFG   120
MSWVRQAPGK GLEWVSSISG SGSDTLYADS VKGRFTISRD NAKTTLYLQM NSLRPEDTAV   180
YYCTIGGSLS RSSQGTLVTV SSGAQPHPIP DSSPLLQFGG QVRQRYLYTD DAQQTEAHLE   240
IREDGTVGGA ADQSPESLLQ LKALKPGVIQ ILGVKTSRFL CQRPDGALYG SLHFDPEACS   300
FRELLLEDGY NVYQSEAHGL PLHLPGQKSP HRDPAPRGPA RFLPLPGLPP ALPEPPGILA   360
PQPPDVGSSD PLSLVGGSQC RSPSYES                                       387

SEQ ID NO: 95           moltype = AA  length = 387
FEATURE                 Location/Qualifiers
REGION                  1..387
                        note = Synthetic
source                  1..387
                        mol_type = protein
                        organism = synthetic construct
SEQUENCE: 95
HGEGTFTSDV SSYLEEQAAK EFIAWLVKGG GGAQPGAQPG AQPGAQPGAQ PGAQPGAQPG    60
AQPGAQPGAQ PGAQPGAQPG AQPGAQPEVQ LVESGGGLVQ PGNSLRLSCA ASGFTFSSFG   120
MSWVRQAPGK GLEWVSSISG SGSDTLYADS VKGRFTISRD NAKTTLYLQM NSLRPEDTAV   180
YYCTIGGSLS RSSQGTLVTV SSGAQPHPIP DSSPLLQFGG QVRQRYLYTD DAQQTEAHLE   240
IREDGTVGGA ADQSPESLLQ LKALKPGVIQ ILGVKTSRFL CQRPDGALYG SLHFDPEACS   300
FRELLLEDGY NVYQSEAHGL PLHLPGQKSP HRDPAPRGPA RFLPLPGLPP ALPEPPGILA   360
PQPPDVGSSD PLSLVGPSQG RSPSYES                                       387

SEQ ID NO: 96           moltype = AA  length = 388
FEATURE                 Location/Qualifiers
REGION                  1..388
                        note = Synthetic
source                  1..388
                        mol_type = protein
                        organism = synthetic construct
SEQUENCE: 96
HGEGTFTSDV SSYLEEQAAK EFIAWLVKGG GGAQPGAQPG AQPGAQPGAQ PGAQPGAQPG    60
AQPGAQPGAQ PGAQPGAQPG AQPGAQPEVQ LVESGGGLVQ PGNSLRLSCA ASGFTFSSFG   120
MSWVRQAPGK GLEWVSSISG SGSDTLYADS VKGRFTISRD NAKTTLYLQM NSLRPEDTAV   180
YYCTIGGSLS RSSQGTLVTV SSGGGGSHPI PDSSPLLQFG GQVRQRYLYT DDAQQTEAHL   240
EIREDGTVGG AADQSPESLL QLKALKPGVI QILGVKTSRF LCQRPDGALY GSLHFDPEAC   300
SFRELLLEDG YNVYQSEAHG LPLHLPGQKS PHRDPAPRGP ARFLPLPGLP PALPEPPGIL   360
APQPPDVGSS DPLSLVGCSQ GRSPSYES                                      388

SEQ ID NO: 97           moltype = AA  length = 389
FEATURE                 Location/Qualifiers
REGION                  1..389
                        note = Synthetic
```

```
source                          1..389
                                mol_type = protein
                                organism = synthetic construct
SEQUENCE: 97
HGEGTFTSDV SSYLEEQAAK EFIAWLVKGG GGAQPGAQPG AQPGAQPGAQ PGAQPGAQPG    60
AQPGAQPGAQ PGAQPGAQPG AQPGGGGSEV QLVESGGGLV QPGNSLRLSC AASGFTFSSF   120
GMSWVRQAPG KGLEWVSSIS GSGSDTLYAD SVKGRFTISR DNAKTTLYLQ MNSLRPEDTA   180
VYYCTIGGSL SRSSQGTLVT VSSGGGGSHP IPDSSPLLQF GGQVRQRYLY TDDAQQTEAH   240
LEIREDGTVG GAADQSPESL LQLKALKPGV IQILGVKTSR FLCQRPDGAL YGSLHFDPEA   300
CSFRELLLED GYNVYQSEAH GLPLHLPGQK SPHRDPAPRG PARFLPLPGL PPALPEPPGI   360
LAPQPPDVGS SDPLSLVGCS QGRSPSYES                                    389

SEQ ID NO: 98                   moltype = AA  length = 388
FEATURE                         Location/Qualifiers
REGION                          1..388
                                note = Synthetic
source                          1..388
                                mol_type = protein
                                organism = synthetic construct
SEQUENCE: 98
HGEGTFTSDV SSYLEEQAAK EFIAWLVKGG GGAQPGAQPG AQPGAQPGAQ PGAQPGAQPG    60
AQPGAQPGAQ PGAQPGAQPG AQPGAQPEVQ LVESGGGLVQ PGNSLRLSCA ASGFTFSSFG   120
MSWVRQAPGK GLEWVSSISG SGSDTLYADS VKGRFTISRD NAKTTLYLQM NSLRPEDTAV   180
YYCTIGGSLS RSSQGTLVTV SSGGGGSHPI PDSSPLLQFG GQVRQRYLYT DDAQQTEAHL   240
EIREDGTVGG AADQSPESLL QLKALKPGVI QILGVKTSRF LCQRPDGALY GSLHFDPEAC   300
SFRELLLEDG YNVYQSEAHG LPLHLPGQKS PHRDPAPRGP ARFLPLPGLP PALPEPPGIL   360
APQPPDVGSS DPLSLVGPSQ GRSPSYES                                     388

SEQ ID NO: 99                   moltype = AA  length = 302
FEATURE                         Location/Qualifiers
REGION                          1..302
                                note = Synthetic
source                          1..302
                                mol_type = protein
                                organism = synthetic construct
SEQUENCE: 99
SGEVQLVESG GGLVQPGNSL RLSCAASGFT FSSFGMSWVR QAPGKGLEWV SSISGSGSDT    60
LYADSVKGRF TISRDNAKTT LYLQMNSLRP EDTAVYYCTI GGSLSRSSQG TLVTVSSGAQ   120
PHPIPDSSPL LQFGGQVRQR YLYTDDAQQT EAHLEIREDG TVGGAADQSP ESLLQLKALK   180
PGVIQILGVK TSRFLCQRPD GALYGSLHFD PEACSFRELL LEDGYNVYQS EAHGLPLHLP   240
GQKSPHRDPA PRGPARFLPL PGLPPALPEP PGILAPQPPD VGSSDPLSLV GPSQGRSPSY   300
ES                                                                 302

SEQ ID NO: 100                  moltype = AA  length = 303
FEATURE                         Location/Qualifiers
REGION                          1..303
                                note = Synthetic
source                          1..303
                                mol_type = protein
                                organism = synthetic construct
SEQUENCE: 100
SGEVQLVESG GGLVQPGNSL RLSCAASGFT FSSFGMSWVR QAPGKGLEWV SSISGSGSDT    60
LYADSVKGRF TISRDNAKTT LYLQMNSLRP EDTAVYYCTI GGSLSRSSQG TLVTVSSGGG   120
GSHPIPDSSP LLQFGGQVRQ RYLYTDDAQQ TEAHLEIRED GTVGGAADQS PESLLQLKAL   180
KPGVIQILGV KTSRFLCQRP DGALYGSLHF DPEACSFREL LLEDGYNVYQ SEAHGLPLHL   240
PGQKSPHRDP APRGPARFLP LPGLPPALPE PPGILAPQPP DVGSSDPLSL VGCSQGRSPS   300
YES                                                                303

SEQ ID NO: 101                  moltype = AA  length = 303
FEATURE                         Location/Qualifiers
REGION                          1..303
                                note = Synthetic
source                          1..303
                                mol_type = protein
                                organism = synthetic construct
SEQUENCE: 101
SGEVQLVESG GGLVQPGNSL RLSCAASGFT FSSFGMSWVR QAPGKGLEWV SSISGSGSDT    60
LYADSVKGRF TISRDNAKTT LYLQMNSLRP EDTAVYYCTI GGSLSRSSQG TLVTVSSGGG   120
GSHPIPDSSP LLQFGGQVRQ RYLYTDDAQQ TEAHLEIRED GTVGGAADQS PESLLQLKAL   180
KPGVIQILGV KTSRFLCQRP DGALYGSLHF DPEACSFREL LLEDGYNVYQ SEAHGLPLHL   240
PGQKSPHRDP APRGPARFLP LPGLPPALPE PPGILAPQPP DVGSSDPLSL VGPSQGRSPS   300
YES                                                                303

SEQ ID NO: 102                  moltype = AA  length = 181
FEATURE                         Location/Qualifiers
REGION                          1..181
                                note = Synthetic
source                          1..181
                                mol_type = protein
```

```
                         organism = synthetic construct
SEQUENCE: 102
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
NKSPHRDPAP RGPARFLPLP GLPPALPEPP GILAPQPPDV GSSDPLSLVG GSQGRSPSYE   180
S                                                                  181

SEQ ID NO: 103           moltype = AA  length = 181
FEATURE                  Location/Qualifiers
REGION                   1..181
                         note = Synthetic
source                   1..181
                         mol_type = protein
                         organism = synthetic construct
SEQUENCE: 103
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVG GSQGRSPSYA   180
S                                                                  181

SEQ ID NO: 104           moltype = AA  length = 181
FEATURE                  Location/Qualifiers
REGION                   1..181
                         note = Synthetic
source                   1..181
                         mol_type = protein
                         organism = synthetic construct
SEQUENCE: 104
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSMVG GSQGRSPSYE   180
S                                                                  181

SEQ ID NO: 105           moltype = AA  length = 181
FEATURE                  Location/Qualifiers
REGION                   1..181
                         note = Synthetic
source                   1..181
                         mol_type = protein
                         organism = synthetic construct
SEQUENCE: 105
HPIPDSSPLL QFGGQVRQRY LYTDDAQQTE AHLEIREDGT VGGAADQSPE SLLQLKALKP    60
GVIQILGVKT SRFLCQRPDG ALYGSLHFDP EACSFRELLL EDGYNVYQSE AHGLPLHLPG   120
QKSPHRDPAP RGPARFLPLP GLPPALPEPP GILAPQPPDV GSSDPLSLVG GSQGRSPSYE   180
S                                                                  181

SEQ ID NO: 106           moltype = AA  length = 57
FEATURE                  Location/Qualifiers
REGION                   1..57
                         note = Synthetic
source                   1..57
                         mol_type = protein
                         organism = synthetic construct
SEQUENCE: 106
GAQPGAQPGA QPGAQPGAQP GAQPGAQPGA QPGAQPGAQP GAQPGAQPGA QPGGGGS       57

SEQ ID NO: 107           moltype = AA  length = 303
FEATURE                  Location/Qualifiers
REGION                   1..303
                         note = Synthetic
source                   1..303
                         mol_type = protein
                         organism = synthetic construct
SEQUENCE: 107
SGEVQLVESG GGLVQPGNSL RLSCAASGFT FSSFGMSWVR QAPGKGLEWV SSISGSGSDT    60
LYADSVKGRF TISRDNAKTT LYLQMNSLRP EDTAVYYCTI GGSLSRSSQG TLVTVSSGGG   120
GSHPIPDSSP LLQFGGQVRQ RYLYTDDAQQ TEAHLEIRED GTVGGAADQS PESLLQLKAL   180
KPGVIQILGV KTSRFLCQRP DGALYGSLHF DPEACSFREL LLEDGYNVYQ SEAHGLPLHL   240
PGQKSPHRDP APRGPARFLP LPGLPPALPE PPGILAPQPP DVGSSDPLSL VGGSQGRSPS   300
YES                                                                303

SEQ ID NO: 108           moltype = AA  length = 387
FEATURE                  Location/Qualifiers
REGION                   1..387
                         note = Synthetic
source                   1..387
                         mol_type = protein
                         organism = synthetic construct
SEQUENCE: 108
```

```
HGEGTFTSDV SSYLEEQAAK EFIAWLVKGG GGAQPGAQPG AQPGAQPGAQ PGAQPGAQPG    60
AQPGAQPGAQ PGAQPGAQPG AQPGAQPEVQ LVESGGGLVQ PGNSLRLSCA ASGFTFSSFG   120
MSWVRQAPGK GLEWVSSISG SGSDTLYADS VKGRFTISRD NAKTTLYLQM NSLRPEDTAV   180
YYCTIGGSLS RSSQGTLVTV SSGAQPHPIP DSSPLLQFGG QVRQRYLYTD DAQQTEAHLE   240
IREDGTVGGA ADQSPESLLQ LKALKPGVIQ ILGVKTSRFL CQRPDGALYG SLHFDPEACS   300
FRELLLEDGY NVYQSEAHGL PLHLPGQKSP HRDPAPRGPA RFLPLPGLPP ALPEPPGILA   360
PQPPDVGSSD PLSLVGGSQG RSPSYES                                      387

SEQ ID NO: 109         moltype = AA  length = 388
FEATURE                Location/Qualifiers
REGION                 1..388
                       note = Synthetic
source                 1..388
                       mol_type = protein
                       organism = synthetic construct
SEQUENCE: 109
HGEGTFTSDV SSYLEEQAAK EFIAWLVKGG GGAQPGAQPG AQPGAQPGAQ PGAQPGAQPG    60
AQPGAQPGAQ PGAQPGAQPG AQPGAQPEVQ LVESGGGLVQ PGNSLRLSCA ASGFTFSSFG   120
MSWVRQAPGK GLEWVSSISG SGSDTLYADS VKGRFTISRD NAKTTLYLQM NSLRPEDTAV   180
YYCTIGGSLS RSSQGTLVTV SSGGGGSHPI PDSSPLLQFG GQVRQRYLYT DDAQQTEAHL   240
EIREDGTVGG AADQSPESLL QLKALKPGVI QILGVKTSRF LCQRPDGALY GSLHFDPEAC   300
SFRELLLEDG YNVYQSEAHG LPLHLPGQKS PHRDPAPRGP ARFLPLPGLP PALPEPPGIL   360
APQPPDVGSS DPLSLVGGSQ GRSPSYES                                     388

SEQ ID NO: 110         moltype =     length =
SEQUENCE: 110
000
```

FUSION POLYPEPTIDES FOR METABOLIC DISORDERS

SEQUENCE LISTING

The instant application contains a Sequence Listing which has been submitted electronically in XML format and is hereby incorporated by reference in its entirety. Said XML copy, created on Jan. 23, 2024, is named 3_074585-8008US01-SEQ.xml and is 153,854 bytes in size.

FIELD OF THE INVENTION

The present invention relates to polypeptides and producing method thereof, pharmaceutical compositions, and methods of using such to prevent and/or treat diseases, especially metabolic diseases.

BACKGROUND

Fibroblast growth factor 21 (FGF 21), a member of the fibroblast growth factor (FGF) family, is a hormone synthesized in several metabolically active organs and regulates glucose and lipid homeostasis. The biology of FGF21 is intrinsically complicated owing to its diverse metabolic functions in multiple target organs. FGF21 has been reported to function in organs such as liver, adipocytes, pancreas, hypothalamus and muscles tissues (Fisher F M, Annu Rev Physiol, 2016, 78:223).

Major biologically active fragment of Glucagon-Like Peptide-1 (GLP-1) is a 30 or 31 amino acid peptide fragment (amino acid 7-36 or 7-37 of GLP-1) deriving from the posttranslational processing of the proglucagon peptide. The initial GLP-1 product GLP-1 stimulates insulin synthesis and secretion and has been shown to prevent hyperglycemia in diabetics, especially type 2 diabetes. However, endogenous GLP-1 only has a half-life of approximately 2 minutes, which results in fasting plasma levels of GLP-1 of only 0-15 pmol/L.

Metabolic disorders are commonly associated with insulin resistance, visceral adiposity, atherogenic dyslipidemia, etc., which pose major and escalating public health and clinical challenge worldwide. However, existing treatment for metabolic diseases faces problems such as short half-life and/or low efficacy.

Therefore, there is a need for an improved therapeutic solution for treating metabolic diseases.

SUMMARY OF THE INVENTION

On a first aspect, the present disclosure provides a polypeptide, which is substantially a fusion polypeptide or fusion protein comprising two or three functional domains that are connected via one or two linkers.

Specifically, in an N-terminus to C-terminus direction, the polypeptide comprises a first fragment and a second fragment, which are connected via a first linker. The first fragment comprises a nanobody domain capable of binding to serum albumin (e.g. human serum albumin), and the second fragment comprises a biologically active FGF21 domain.

Herein, the FGF21 domain comprises an amino acid sequence having at least 90% sequence identity to, while substantially retaining biological activity of, SEQ ID NO: 1. As such, the FGF21 domain may comprise no more than 12, 11, 10, 9, 8, 7, 6, 5, 4, 3, or 2 amino acid residue mutations relative to SEQ ID NO: 1, as long as such mutation-containing FGF21 variant still retains the biological activity of FGF21. Herein, an amino acid residue mutation can a substitution, an insertion, or a deletion.

According to some embodiments of the polypeptide, the FGF21 domain may comprise one or more amino acid residue mutations, each at a position selected from positions 121, 168, 171, and 180 relative to SEQ ID NO: 1. Optionally, the one or more amino acid residue mutations in the FGF21 domain may include one, two, three or four of the following three substitutions: N121Q, M168L, P171G and A180E.

According to some embodiments of the polypeptide, the FGF21 domain may comprise all three substitutions of N121Q, M168L, and A180E, and the amino acid sequence of the FGF21 domain is set forth in SEQ ID NO: 5. Other amino acid residues in the FGF21 domain may be additionally mutated on top of the three mutations. In certain embodiments, the FGF21 domain further comprises a substitution P171G. According to some embodiments of the polypeptide, the FGF21 domain comprises the amino acid sequence of SEQ ID NO: 14.

According to some embodiments of the polypeptide, the FGF21 domain further comprises a conjugatable residue. Herein, the conjugatable residue can optionally be at a position within a C-terminal fragment spanning from position 169 to position 181 relative to SEQ ID NO: 1. According to certain embodiments, the conjugatable residue is at a position selected from the group consisting of positions 169, 170, 171, 172, 173, 174, 180 and 181 relative to SEQ ID NO: 1. According to some embodiments of the polypeptide, the FGF21 domain comprises the amino acid sequence of SEQ ID NOs: 2-5, 89-91, 14, and 102-105, except for a mutation to a conjugatable residue at a position within a C-terminal fragment spanning from position 169 to position 181 relative to SEQ ID NO: 1.

According to some embodiments of the polypeptide, the FGF21 domain comprises the amino acid sequence of SEQ ID NOs: 6-13, 16-19, and 92.

According to some embodiments, the polypeptide is conjugated with a functional moiety at the conjugatable residue in the FGF21 domain-containing second fragment.

Herein, the functional moiety that is conjugated to the FGF2 domain may optionally comprise a glycosyl moiety or a synthetic chemical moiety.

According to some embodiments of the polypeptide, the functional moiety comprises a glycosyl moiety, and the conjugatable residue can be an introduced residue that is glycosylatable, such as Threonine (T) or Asparagine (N) residues. More specifically, the conjugatable residue may optionally be an introduced T at position 172 or position 173, or may be an introduced N residue at position 170 or position 174, relative to SEQ ID NO: 1. According to some embodiments of the polypeptide, the FGF21 domain comprises the amino acid sequence selected from the group consisting of SEQ ID NOs: 16-19.

According to some other embodiments of the polypeptide, the functional moiety comprises a synthetic chemical moiety. As such, the conjugatable residue may optionally comprise an introduced cysteine (C), and the synthetic chemical moiety may comprise a structure of *—X—Y—Z. Herein X, Y, and Z are interconnected via bonds, and the * end of X is connected to the conjugatable residue on the polypeptide. X can be

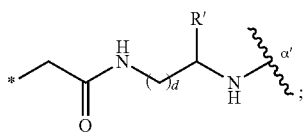

Y can be

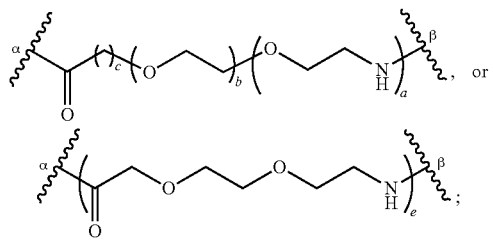

and Z can be

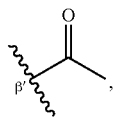

wherein position α is linked to position α', position β is linked to position β'. Herein, R1 can be hydrogen or —COOH; d can be 1, 2, or 3; a can be 1, 2 or 3; b can be 1, 2 or 3; c can be 1 or 2; d can be 1, 2, or 3; and e can be 1, 2, or 3.

According to some more specific embodiments of the polypeptide, the synthetic chemical moiety has the below structure:

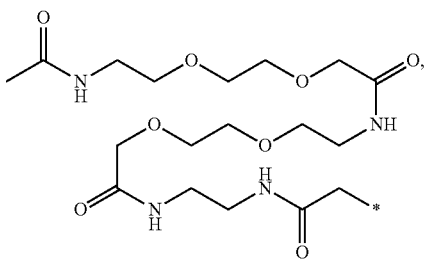 [SMILES: *CC(=O)NCCNC(=O)COCCOCCNC(=O)COCCOCCNC(C)=O]

also referred herein as Ac-2XADO-EDA-CO—CH2-*.

Optionally, the introduced cysteine can be at a position selected from a group consisting of 169, 170, 171, 172, 173, 174, 180 and 181 relative to SEQ ID NO: 1. According to certain embodiments, the conjugatable residue is at the position 171 or 174 relative to SEQ ID NO: 1. According to some of these embodiments of the polypeptide, the FGF21 domain comprises the amino acid sequence of SEQ ID NOs: 6-13 and 92.

In some embodiments of the polypeptide, the FGF21 domain comprises the amino acid sequence of SEQ ID NO: 8, with the introduced cysteine at position 171, conjugated at the introduced cysteine residue with the synthetic chemical moiety having the below structure:

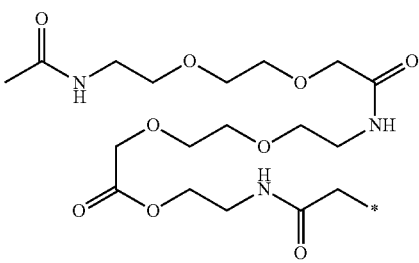 [SMILES: *CC(=O)NCCOC(=O)COCCOCCNC(=O)COCCOCCNC(C)=O]

(also referred herein as Ac-2XADO-EDA-CO—CH2*).

In some embodiments of the polypeptide, the FGF21 domain can comprise the amino acid sequence of SEQ ID NO: 92, with the introduced cysteine at position 174, conjugated at the introduced cysteine residue with the synthetic chemical moiety having the below structure:

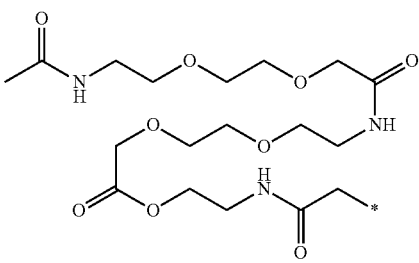 [SMILES: *CC(=O)NCCOC(=O)COCCOCCNC(=O)COCCOCCNC(C)=O]

(also referred herein as Ac-2XADO-EDA-CO—CH2*).

Other embodiments of the polypeptide may alternatively include:

i) the FGF21 domain comprises the amino acid sequence of SEQ ID NO: 6, and the introduced cysteine is at position 169;

ii) the FGF21 domain comprises the amino acid sequence of SEQ ID NO: 7, and the introduced cysteine is at position 170;

iii) the FGF21 domain comprises the amino acid sequence of SEQ ID NO: 8, and the introduced cysteine is at position 171;

iv) the FGF21 domain comprises the amino acid sequence of SEQ ID NO: 9, and the introduced cysteine is at position 172;

v) the FGF21 domain comprises the amino acid sequence of SEQ ID NO: 10, and the introduced cysteine is at position 173;

vi) the FGF21 domain comprises the amino acid sequence of SEQ ID NO: 11, and the introduced cysteine is at position 174;

vii) the FGF21 domain comprises the amino acid sequence of SEQ ID NO: 12, and the introduced cysteine is at position 180; or viii) the FGF21 domain comprises the amino acid sequence of SEQ ID NO: 13, and the introduced cysteine is at position 181, ix) the FGF21 domain comprises the amino acid sequence of SEQ ID NO: 92, and the introduced cysteine is at position 174, and optionally is conjugated at the introduced cysteine residue with the synthetic chemical moiety having the below structure:

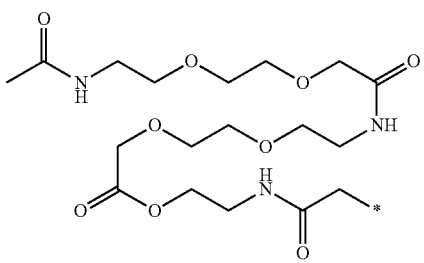 [SMILES: *CC(=O)NCCOC(=O)COCCOCCNC(=O)COCCOCCNC(C)=O]

(also referred herein as Ac-2XADO-EDA-CO—CH2*).

Additionally and alternatively, in some other embodiments of the polypeptide, the FGF21 domain further comprises a substitution of P171G relative to SEQ ID NO: 1. In such embodiments, the FGF21 domain comprises an amino acid sequence selected from the group consisting of SEQ ID NOs: 14 and 92.

In any of the above embodiments of the polypeptide, the nanobody domain may optionally comprise a VHH domain, optionally a VHH domain capable of binding to human serum albumin (HSA).

Further optionally, the VHH domain can be humanized.

According to some embodiments, the VHH domain may comprise a complementarity determining region 1 (CDR1), a complementarity determining region 2 (CDR2), and a complementarity determining region 3 (CDR3). Herein, the CDR1 may comprise the sequence of SEQ ID NO: 20 or a variant thereof having up to 3, 2, or 1 amino acid mutation; the CDR2 may comprise the sequence of SEQ ID NO: 21 or a variant thereof having up to 3, 2, or 1 amino acid mutation; and/or the CDR3 may comprise the sequence of SEQ ID NO: 22 or a variant thereof having up to 3, 2, or 1 amino acid mutation, and the VHH domain substantially retains the binding specificity to serum albumin, optionally to human serum albumin.

In certain specific embodiments of the polypeptide, the VHH domain comprises a complementarity determining region 1 (CDR1) comprising the sequence of SEQ ID NO: 20, a CDR2 comprising the sequence of SEQ ID NO: 21, and a CDR3 comprising the sequence of SEQ ID NO: 22.

In certain specific embodiments of the polypeptide, the VHH domain comprises an amino acid sequence of SEQ ID NO: 23, or a variant thereof having at least 70% (e.g. at least 75%, 80%, 85%, 90%, 95%, 99% identity to SEQ ID NO: 23, and the variant substantially retains binding specificity and/or affinity to serum albumin.

Herein, optionally, the variant of SEQ ID NO: 23 may have up to 10, 9, 8, 7, 6, 5, 4, 3, 2, or 1 amino acid mutation relative to SEQ ID NO: 23.

In any of the above embodiments, the nanobody domain may optionally further comprise an N-terminal extension attached to a N-terminus of the VHH domain, the N-terminal extension may optionally comprise amino acid residues of SG, AG, S or A.

According to some specific embodiment of the polypeptide, the nanobody domain comprises an amino acid sequence selected from SEQ ID NOs: 24-27.

In any embodiments of the polypeptide described above, the first linker can have a length of at least four amino acid residues.

According to some embodiments, the first linker may comprise no acidic amino acid residue, and more specifically, the first linker may not comprise any of D residue or E residue.

Optionally, the first linker may comprise one or more units of a first repeating sequence, and according to some embodiments, the first repeating sequence may consist of no more than 4 or 6 types of amino acid residues selected from the group consisting of: G, Q, A, P, T and S.

According to some specific embodiments of the polypeptide, the first repeating sequence may comprise or consist of an amino acid sequences selected from a group consisting of $G_fS_g$ (herein each of f and g is independently an integer selected from 1 to 5), SEQ ID NO: 35 (GAQP), SEQ ID NO: 36 (GQAP), SEQ ID NO: 37 (GPAQ), SEQ ID NO: 38 (GPQA), SEQ ID NO: 39 (GSQP), SEQ ID NO: 40 (GASP), SEQ ID NO: 41 (GPAS), SEQ ID NO: 42 (GPSA), SEQ ID NO: 43 (GGGS), SEQ ID NO: 44 (GSGS), SEQ ID NO: 45 (GGGGS), SEQ ID NO: 46 (GSAPGSPAGSPTGSAPGSPA), and SEQ ID NO: 110 (GS).

In certain embodiments, the first repeating sequence may have an amino acid sequence set forth in SEQ ID NO: 35 (GAQP), and the number of units may be an integer between 1 and 10.

According to certain specific embodiment of the polypeptide, the first linker comprises an amino acid sequence selected from the group consisting of SEQ ID NO: 35 (GAQP), SEQ ID NO: 49 ((GAQP) 2), SEQ ID NO: 50 ((GAQP)$_5$), SEQ ID NO: 51 ((GAQP)$_{10}$), and SEQ ID NO: 48 (GGGGSGGGS).

In any of the embodiments of the polypeptide described above, the polypeptide may further comprise, over an N-terminus of the first fragment, a third fragment that comprises another functional domain. Herein, the first fragment and the third fragment are connected via a second linker.

Herein, the another functional domain of the third fragment may optionally comprise a biologically active protein, or a fragment thereof, of one selected from the group consisting of glucagon-like peptide-1 (GLP-1), insulin, leptin, glucagon, gastrin, gastric inhibitory polypeptide (GIP), amylin, calcitonin, cholecystokinin, peptide YY, neuropeptide Y, bone morphogenetic protein-6 (BMP-6), bone morphogenetic protein-9 (BMP-9), oxyntomodulin, oxytocin, glucagon-like peptide-2 (GLP-2), irisin, fibronectin type III domain containing protein 5 (FNDC5), apelin, adiponectin, C1q and tumor necrosis factor related protein (CTRP family), resistin, visfatin, omentin, retinol binding protein-4 (RBP-4), glicentin, angiopoietin, interleukin-22 (IL-22), exendin-4, and growth hormone.

According to some embodiments of the polypeptide, the another functional domain of the third fragment comprises a biologically active peptide, or a fragment thereof, of GLP-1, and may comprise an amino acid sequence having at least 70% sequence identity to, while retaining substantial biological activity of, SEQ ID NO: 28.

Herein optionally, the another functional domain may comprise one or more mutations at positions 8, 22, 26, 34, and 36, or any combination thereof, relative to SEQ ID NO: 28.

According to some embodiments of the polypeptide, the one or more mutations in the another functional domain of the third fragment of the polypeptide may comprise A8G, G22E, K26R, K34R, and R36G, or any combination thereof. According to some embodiments of the polypeptide, the one or more mutations in the another functional domain of the third fragment of the polypeptide may comprise A8G, G22E, and R36G, or any combination thereof.

According to some specific embodiment of the polypeptide, the another functional domain of the third fragment comprises an amino acid sequence selected from the group consisting of SEQ ID NO: 29, and SEQ ID NOs: 31-34.

In any of the above mentioned embodiments of the polypeptide comprising a first fragment which connects with an N-terminus of the first fragment via a second linker.

In certain embodiments, the second linker may have a length of at least four amino acid residues. In certain embodiments, the second linker may have a length of at least 8, 12, 16, or 20 amino acid residues.

Herein the second linker may comprise one or more units of a second repeating sequence, and the second repeating sequence may consist of no more than 4 or 6 types of amino acid residues selected from the group consisting of: G, Q, A, E, P, T and S.

According to some specific embodiments of the polypeptide, the second repeating sequence may comprise or consist of an amino acid sequence that is selected from a group consisting of $G_hS_i$ (herein, each of h and i is independently an integer selected from 1 to 5), SEQ ID NO: 35 (GAQP), SEQ ID NO:55 (GQEP), SEQ ID NO: 56 (GEQP), SEQ ID NO: 57 (GPQE), SEQ ID NO: 58 (GPEQ), SEQ ID NO: 59 (GSEP), SEQ ID NO: 60 (GESP), SEQ ID NO: 61 (GPSE), SEQ ID NO: 62 (GPES), SEQ ID NO: 36 (GQAP), SEQ ID NO: 37 (GPAQ), SEQ ID NO: 38 (GPQA), SEQ ID NO: 39 (GSQP), SEQ ID NO: 40 (GASP), SEQ ID NO: 41 (GPAS), SEQ ID NO: 42 (GPSA), SEQ ID NO: 43 (GGGS), SEQ ID NO: 44 (GSGS), SEQ ID NO: 45 (GGGGS), SEQ ID NO: 46 (GSAPGSPAGSPTGSAPGSPA) and SEQ ID NO: 110 (GS).

Further according to some embodiments, the second repeating sequence may have an amino acid sequence set forth in SEQ ID NO: 35 (GAQP), and a number of the one or more units may be an integer between 1 and 15.

According to certain specific embodiments of the polypeptide, the second linker comprises an amino acid sequence selected from the group consisting of SEQ ID NO: 49 ((GAQP) 2), SEQ ID NO: 50 ((GAQP) 5), SEQ ID NO: 51 ((GAQP) 10), and SEQ ID NO: 52 ((GAQP) 14), and SEQ ID NO: 47 ((GGGGS) 4).

According to certain specific embodiments of the polypeptide which consisting of the first and second fragments, the polypeptide comprises an amino acid sequence selected from the group consisting of SEQ ID NOS: 63-68, 93, 99, 100, 101 and 107. According to certain specific embodiments of the polypeptide, the polypeptide comprises an amino acid sequence selected from the group consisting of SEQ ID NOS: 63, 68, and 100, and is conjugated at the introduced cysteine residue at position 171 relative to SEQ ID NO: 1 with the synthetic chemical moiety provided herein. According to certain specific embodiments of the polypeptide, the polypeptide comprises an amino acid sequence of SEQ ID NO: 93, and is conjugated at the introduced cysteine residue at position 174 relative to SEQ ID NO: 1 with the synthetic chemical moiety provided herein. According to certain of these specific embodiments of the polypeptide, the synthetic chemical moiety has the below structure:

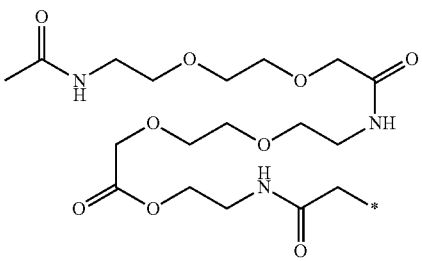 [SMILES: *CC(=O)NCCOC(=O)COCCOCCNC(=O)COCCOCCNC(C)=O]

(also referred herein as Ac-2XADO-EDA-CO—CH2*). According to certain specific embodiments of the polypeptide, the polypeptide comprises an amino acid sequence selected from the group consisting of SEQ ID NOs: 64-67, 93 and 107, and is not conjugated.

According to certain specific embodiments of the polypeptide which consisting of the first, second and third fragments, the polypeptide comprises an amino acid sequence selected from the group consisting of SEQ ID NOS: 70, 74, 75, 79-83, 85, 94-98, and 108-109. According to certain specific embodiments of the polypeptide, the polypeptide comprises an amino acid sequence selected from the group consisting of SEQ ID NOS: 74, 81-83, 85, and 96-97, and is conjugated at the introduced cysteine residue at position 171 relative to SEQ ID NO: 1 with the synthetic chemical moiety provided herein. According to certain specific embodiments of the polypeptide, the polypeptide comprises an amino acid sequence of SEQ ID NO: 94, and is conjugated at the introduced cysteine residue at position 174 relative to SEQ ID NO: 1 with the synthetic chemical moiety. According to certain of these specific embodiments of the polypeptide, the synthetic chemical moiety has the below structure:

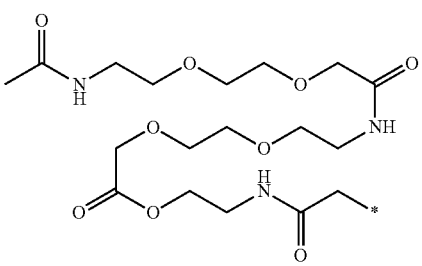 [SMILES: *CC(=O)NCCOC(=O)COCCOCCNC(=O)COCCOCCNC(C)=O]

(also referred herein as Ac-2XADO-EDA-CO—CH2*). According to certain specific embodiments of the polypeptide, the polypeptide comprises an amino acid sequence selected from the group consisting of SEQ ID NOs: 70, 75, 79-80, 85, 94, 95, 98 and 108-109, and is not conjugated.

On a second aspect of the present disclosure, a pharmaceutical composition is further provided. The pharmaceutical composition comprises the polypeptide according to any embodiments as described above, and a pharmaceutically acceptable carrier.

On a third aspect of the present disclosure, a method of preventing or treating a metabolic disorder in a subject in need thereof is also provided, comprising the step of administering a therapeutically effective amount of the polypeptide according to any embodiments as described above, or the pharmaceutical composition described above.

Herein, the metabolic disorder can be diabetes, obesity, non-alcoholic steatohepatitis (NASH), cardiovascular like dyslipidaemia, arteriosclerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, primary biliary cirrhosis (PBC) or severe hypertriglyceridemia (SHTG).

On a fourth aspect of the present disclosure, a polynucleotide is further provided, which encodes the polypeptide as defined according to any embodiments as described above.

On a fifth aspect of the present disclosure, a vector is further provided, which comprises the polynucleotide as described above.

On a sixth aspect of the present disclosure, a host cell is further provided, which comprises the vector as described above.

On a seventh aspect of the present disclosure, a process for producing the polypeptide as described above is further provided. The process comprises the steps of:
S100: culturing the host cell as described above under a condition that allows expression of the polynucleotide as defined above or a precursor thereof further comprising a removable tag; and
S200: collecting and purifying the polypeptide or the precursor thereof from the host cell.

According to some embodiments of the process, the polypeptide is conjugated with a functional moiety at a conjugatable residue in the second fragment, and the process further comprises the following step after step S200 of collecting and purifying the polypeptide from the host cell:
S300: conjugating the functional moiety to the polynucleotide.

According to some embodiments of the process, the host cell is *E. coli*, the vector comprises an *E. coli*-compatible vector, and the polypeptide encoded by the polynucleotide in the vector is codon optimized for *E. coli* expression.

According to some embodiments of the process, step S200 of collecting and purifying the polypeptide from the host cell may comprise the following sub-steps:
S210: collecting the precursor of the polypeptide;
S220: allowing the precursor of the polypeptide to refold;
S230: treating the refolded precursor of the polypeptide to remove the tag thereby obtain the polypeptide; and
S240: purifying the polypeptide.

According to some embodiments of the polypeptide producing process, the process further comprises conjugating the purified polypeptide with the functional moiety. In certain embodiments, the functional moiety to be conjugated to the polypeptide is

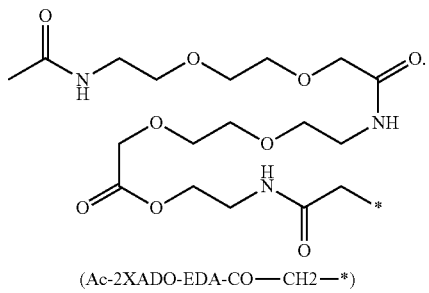

(Ac-2XADO-EDA-CO—CH2—*)

Throughout the present disclosure, the articles "a," "an," and "the" are used herein to refer to one or to more than one (i.e., to at least one) of the grammatical object of the article. By way of example, "a polypeptide" means one polypeptide or more than one polypeptides.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 7, 8, 9, and 10, and fractional values as appropriate. Similarly, ranges delimited by "at least" are understood to include the lower value provided and all higher numbers.

As used herein, the term "approximately", "about", "around" or alike, is understood to include within three standard deviations of the mean or within standard ranges of tolerance in the specific art. In certain embodiments, about is understood a variation of no more than 0.5.

The term "or" is used inclusively herein to mean, and is used interchangeably with, the term "and/or," unless context clearly indicates otherwise.

The terms such as "comprise", "comprising", "contain", "containing" or alike, are to be construed as open-ended terms (i.e., meaning "including, but not limited to,") unless otherwise noted.

The term "including" is used herein to mean, and is used interchangeably with, the phrase "including but not limited to". Similarly, "such as" is used herein to mean, and is used interchangeably, with the phrase "such as but not limited to".

The term "consist essentially of" implies the exclusion of all, most or all but a negligible amount of other elements, or it allows for elements not explicitly recited, but excludes elements that are found in the prior art or that affect a basic or novel property. When a polypeptide is said to "consist essentially of" an amino acid sequence, this means that the polypeptide is composed mostly of the amino acid sequence, with no more than 10 (for example, no more than 6, 5, 4, 3, 2, or 1) additional amino acid residues at one end or both ends of the polypeptide.

BRIEF DESCRIPTION OF THE FIGURES

FIG. 7 show all the amino acid sequences disclosed in the present disclosure.

DETAILED DESCRIPTION

Figure 1A:
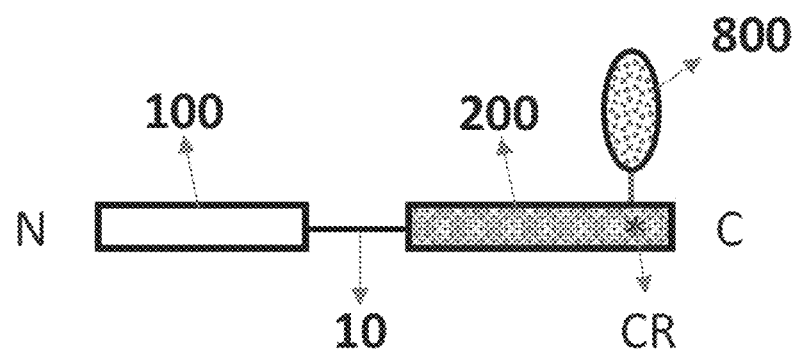
FIGS. 1A and 1B illustrate a polypeptide according to two different embodiments of the present disclosure.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein, including publications, patents and patent applications are incorporated herein by reference in their entirety.

Definitions

The term "protein", "peptide" and "polypeptide" are used interchangeably herein and refer a polymer of amino acid residues linked by covalent bonds such as peptide bonds. A protein or polypeptide as provided herein can comprise naturally occurring or non-natural amino acid residues, or both. Polypeptides, peptides and proteins provided herein can comprise any suitable length of amino acid residues, for example, from at least 3, 4, 5, 10, 20, 30, 40, 50, 60, 70, 80, 90, 100, 200, 300, 400, 500, 600, 700, 800, 900, 1000, or more amino acid residues in length.

The term "naturally occurring" amino acid residue, as used herein, refers to an amino acid residue found in native proteins or peptides, all in their D and L stereoisomers if their structure allows such stereoisomeric forms. Examples of naturally occurring amino acid residues include, but not limited to, 20 standard amino acids, including, glycine (Gly or G), alanine (Ala or A), valine (Val or V), leucine (Leu or L), isoleucine (Ile or I), serine (Ser or S), cysteine (Cys or C), threonine (Thr or T), methionine (Met or M), proline (Pro or P), phenylalanine (Phe or F), tyrosine (Tyr or Y), tryptophan (Trp or W), histidine (His or H), lysine (Lys or K), arginine (Arg or R), aspartate (Asp or D), glutamate (Glu or E), asparagine (Asn or N), and glutamine (Gln or Q), and their natural analogs, such as canavanine, pyrrolysine (PYL), selenocysteine, pyrroline-carboxy-lysine (PCL), Sarcosine, beta-Alanine, phosphoserine, γ-carboxyglutamate, and ornithine. Examples of naturally occurring amino acid residues in their D stereoisomer include, for example, D-aspartate, D-Serine, D-Cysteine, D-Alanine, D-glutamate and so on.

An "amino acid analog" is a compound that has the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs can have modified R groups {e.g., norleucine) or modified peptide backbones, but will retain the same basic chemical structure as a naturally occurring amino acid.

A "non-natural" amino acid residue, as used herein, refers to any amino acid residues that are not found in nature, including without limitation, a modified amino acid residue, and/or an amino acid mimetic, which is not one of the known naturally occurring amino acids, yet functions in a manner similar to the naturally occurring amino acids. Modified amino acid or a mimetic can be generated by addition of a chemical entity such as a carbohydrate group, a phosphate group, a farnesyl group, an isofarnesyl group, a fatty acid group, a linker for conjugation, functionalization, or other modification, etc. A non-natural amino acid can also refer to an amino acid manufactured by chemical synthesis. Exemplary non-natural amino acids include, but not limited to, 2-Aminoisobutyric acid (Aib), imidazole-4-acetate (IA), imidazolepropionic acid (IPA), a-aminobutyric acid (Abu), tert-butylglycine (Tle), 3-aminomethyl benzoic acid, anthranilic acid, des-amino-histidine (abbreviated DesaminoHis, alternative name imidazopropionic acid, abbreviated Impr), the beta analogues of amino acids such as β-alanine, 2-amino-histidine, β-hydroxy-histidine, homohistidine, Nα-acetyl-histidine, α-fluoro-methyl-histidine, α-methyl-histidine, α,α-dimethyl-glutamic acid, m-CF3-phenylalanine, α,β-diaminopropionic acid (abbreviated Dap), 3-pyridylalanine, 2-pyridylalanine or 4-pyridylalanine, (1-aminocyclopropyl) carboxylic acid, (1-aminocyclobutyl)-carboxylic acid, (1-aminocyclopentyl) carboxylic acid, (1-aminocyclohexyl) carboxylic acid, (1-aminocycloheptyl) carboxylic acid, and (1-aminocyclooctyl) carboxylic acid. Introduction of non-natural amino acids into a fusion polypeptide, polypeptide fragment, and/or polypeptide complex may be realized by the technology described in Wang et al., Science 292:498-500, 2001; Deiters et al., J Am Chem Soc 125:1 1782-1 1783, 2003; Wang and Schultz, Science 301:964-967, 2003; Zhang et al., Science 303:371-373, 2004 or in U.S. Pat. No. 7,083,970. Briefly, some of these expression systems involve site-directed mutagenesis to introduce a stop codon, such as an amber (UAG), ochre (UAA), and opal (UGA) codons) into the open reading frame encoding a fusion polypeptide of the present disclosure. Other codons, such as a four-base codon (e.g. AGGA, AGGU, CGGU, CGCU, CGAU, CCCU, CUCU, CUAU, and GGGU), a five-base codon, a six-base codon, etc. can also be introduced into the expression systems for non-natural amino acids. Such expression vectors are then introduced into a host that can utilize a tRNA specific for the introduced stop codon or other codons and carried with the non-natural amino acid of choice.

The term "fusion" or "fused" when used with respect to amino acid sequences (e.g. peptide, polypeptide or protein) refers to combination of two or more amino acid sequences, for example by chemical bonding or recombinant means, into a single amino acid sequence which does not exist naturally. A fusion amino acid sequence may be produced by genetic recombination of two encoding polynucleotide sequences, and can be expressed by a method of introducing a construct containing the recombinant polynucleotides into a host cell.

"Percent (%) sequence identity" is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). In other words, percent (%) sequence identity of an amino acid sequence (or nucleic acid sequence) can be calculated by dividing the number of amino acid residues (or bases) that are identical relative to the reference sequence to which it is being compared by the total number of the amino acid residues (or bases) in the candidate sequence or in the reference sequence, whichever is shorter. Conservative substitution of the amino acid residues is not considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23 (21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

In one aspect, the present disclosure provides a polypeptide which is substantially a fusion polypeptide/protein comprising two or three functional domains, and every two neighboring functional domains is operably connected via a linker. Optionally, the fusion polypeptide/protein can be conjugated.

Figure 1B:
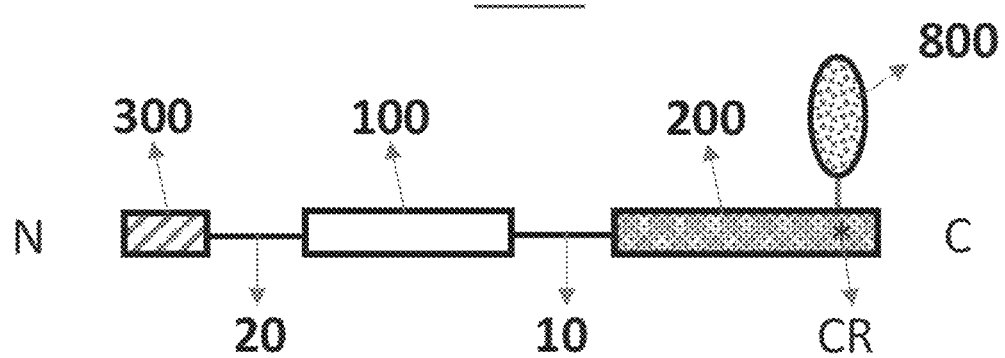

FIG. 1A and FIG. 1B illustrate two major embodiments of the polypeptide provided in this present disclosure. As shown in FIG. 1A, the first embodiment of the polypeptide 001A comprises, in an N-terminus to C-terminus direction, a first fragment 100 and a second fragment 200, which are connected via a first linker 10. The first fragment 100 substantially comprises a nanobody domain that is capable of binding to serum albumin, such as human serum albumin (HSA). The second fragment 200 comprises a biologically active FGF21 domain, which substantially comprises a functional form of FGF21, and according to certain specific embodiments of the disclosure, comprises an amino acid sequence having at least 90% sequence identity to, while substantially retaining biological activity of, SEQ ID NO: 1.

Optionally, the polypeptide may further comprise yet one additional functional domain besides the nanobody domain in the first fragment 100 and the FGF21 domain in the second fragment 200. As shown in FIG. 1B, in addition to the first fragment 100 and the second fragment 200 as in the first embodiment illustrated in FIG. 1A, this second embodiment of the polypeptide 001B further includes a third fragment 300 over an N-terminus of the first fragment 100. The third fragment 300 comprises an additional functional domain that can exert a biological activity that is additive to, or in synergy with, the FGF21 domain in the second fragment 200. The first fragment 100 and the third fragment 300 are connected via a second linker 20. According to some embodiments of the present disclosure, this additional functional domain in the third fragment 300 is a biologically active glucagon-like peptide-1 (GLP-1) domain, which substantially comprises a functional form of GLP-1. According to some embodiments, comprises an amino acid sequence having at least 70% sequence identity to, while substantially retaining the biological activity of, SEQ ID NO: 28.

The term "functional form" as used herein, refers to different forms (such as variants, fragments/portions, fusions, derivatives and mimetics) of the parent molecule, which, despite of having difference in amino acid sequences or in chemical structures, still retains substantial biological activity of the parent molecule. The expression "retain substantial biological activity", as used herein, means exhibiting at least part of (for example, no less than about 20%, 30%, 40%, 50%, 60%, 70%, 80%, or 90%) or all of the biological activity of the parent molecule. A functional form of a parent polypeptide may include both naturally-occurring variant forms and non-naturally occurring forms such as those obtained by recombinant methods or chemical synthesis. The functional forms may contain non-natural amino acid residues.

The term "variant" as used herein refers to a polypeptide having at least 70% sequence identity to the parent polypeptide and retain at least partial function of the parent polypeptide. A variant may differ from the parent polypeptide by one or more amino acid residues. For example, a variant may have substitutions, additions, deletions, insertions, or truncations of one more amino acid residue of the parent polypeptide.

The term "fragment" or "portion" as used herein refers to partial sequence of the parent polypeptide of any length. A fragment may still retain at least partial function of the parent polypeptide.

The term "derivative" as used herein refers to a chemically modified polypeptide or fusion polypeptide, in which one or more well-defined substituent groups have been covalently attached to one or more specific amino acid residues of the polypeptide or fusion polypeptide. Exemplary chemical modification can be, e.g. alkylation, acylation, esterification, amidation, phosphorylation, glycosylation, labeling, methylation of one or more amino acids, or conjugation with one or more moieties.

The term "mimetics" as used herein refers to molecular structures that serve as substitutes for amino acids, peptides, polypeptides, or fusion polypeptide. For example, amino acid mimetics, as used herein, can be synthetic structures (either known or yet unknown), which may or may not be an amino acid, but retain the functional features of the parent amino acids while the structure of the amino acid mimetic is different from the structure of the parent amino acid. Examples include a methacryloyl or acryloyl derivative of an amide, β-, γ-, δ-imino acids (such as piperidine-4-carboxylic acid) and the like.

FGF21 Domain

The polypeptides disclosed herein comprises the FGF21 domain. For example, each of the first and second embodiments of the polypeptide disclosed herein and illustrated in FIGS. 1A and 1B comprises the FGF21 domain.

The term "FGF21" as used herein refers to, and is short for, "Fibroblast Growth Factor 21", and is intended to broadly encompasses all functional forms including the native human FGF21, as well as functional variants, fragments, fusions, derivatives or mimetics thereof. The native human FGF21 consists of 209 amino acid residues (Uniprot datebase with access no. Q9NSA1), with amino acid residues 1-28 being a signal polypeptide and amino acid residues 29-209 being a mature polypeptide of 181 residues. The expression "biologically active FGF21 domain" as provided in the present disclosure refers to a functional form of FGF21, which can be the mature polypeptide, or functional variants, fragments, fusions, derivatives or mimetics thereof. The mature polypeptide of human FGF21 is included herein as SEQ ID NO: 1. As used herein, the numbering of the residues in FGF21 is referred to the sequence of SEQ ID NO: 1, which begins with His at position 1 and Ser at position 181.

A functional form of the mature polypeptide of FGF21 is capable of activating the FGF21 receptor at a level comparable to, or no less than about 20% (or no less than 30%, 40%, 50%, 60%, 70%, 80%, 90%) of, that of the mature polypeptide of the native human FGF21. Activation of the FGF21 receptor can lead to biological activities such as, for example, the ability to activate glucose uptake in adipocytes, the ability to lower blood glucose and triglyceride levels, or the ability to lower bodyweight (Tezze C et al, Front Physiol. 2019, 10:419). Many functional forms of the mature polypeptide of FGF21 are known in the art, for example, without limitation, those disclosed in, WO2019043457A2, WO2018088838A1, WO2018039081A1, WO2017220706A1, WO2017180988A2, WO2017116207A1, WO2017093465, WO2017059371A1, WO2016102562A1, WO2016065326A, WO2013173158A1, WO2013052311A1, WO2013033452A2, WO2012066075A1, WO2012059873A2, WO2012010553A1, WO2011140086A2, WO2010084169A2, WO2010065439A1, WO2008121563A2, WO2006028595A2, WO2006028714A1, WO2005113606A2, WO2016102562A, disclosure of which are incorporated herein by their entirety.

In certain embodiments, the FGF21 domain provided herein comprises an amino acid sequence having at least 90% sequence identity to, while retaining substantial biological activity of, SEQ ID NO: 1.

In certain embodiments, the FGF21 domain comprises no more than 12, 11, 10, 9, 8, 7 amino acid mutations (e.g. substitutions, insertions, or deletions) relative to SEQ ID NO: 1 while retaining substantial biological activity of SEQ ID NO: 1. In certain embodiments, the FGF21 domain comprises the amino acid sequence of SEQ ID NOs: 2-14, 16-19, 89-92, and 102-105.

In certain embodiments, the FGF21 comprises one or more mutations. In certain embodiments, the one or more mutations comprise a conservative substitution. In certain embodiments, the one or more mutations is at a position selected from positions consisting of 121, 168, 171 and 180 relative to SEQ ID NO: 1.

In certain embodiments, the one or more mutations in the FGF21 domain are selected from N121Q, M168L, P171G and A180E, or any combination thereof. For example, the FGF21 domain in the polypeptide disclosed herein may optionally contain one of the four mutations, two of the four mutations, three of the four mutations or four of the mutations.

In certain embodiments, the FGF21 domain comprises of a combination of mutations relative to SEQ ID NO: 1 selected from the group consisting of:
1) N121Q,
2) M168L;
3) A180E;
4) N121Q and M168L;
5) N121Q and A180E;
6) M168L and A180E;
7) N121Q, P171G and A180E;
8) N121Q, M168L, and P171G;
9) M168L, P171G and A180E; and
10) N121Q, M168L, P171G and A180E.

In certain embodiments, the FGF21 domain may comprise an amino acid sequence set forth in SEQ ID NO: 2 (N121Q), SEQ ID NO: 3 (M168L), SEQ ID NO: 4 (A180E), SEQ ID NO: 5 (N121Q, M168L, and A180E), SEQ ID NO: 89 (N121Q and M168L), SEQ ID NO: 90 (N121Q and A180E), SEQ ID NO: 91 (M168L and A180E), or SEQ ID NO: 14 (N121Q, M168L, P171G and A180E).

In certain embodiments, the FGF21 domain in the polypeptide further comprises a conjugatable residue or up to one conjugatable residue, to which the functional moiety is conjugated.

The term "conjugatable residue" as used herein, refers to an amino acid residue at a particular position within the polypeptide, which not only has a functional group capable of being chemically or enzymatically conjugated to a chemical moiety, but its position in the polypeptide allows it to be prone to such conjugation in a conjugating reaction for that particular functional group. "Conjugation" as used herein refers to a reaction that joins two molecules together to form one physical entity. For example, a covalent bond linking the two molecules can be formed in conjugation. A conjugatable residue can be a natural amino acid residue, a non-natural amino acid residue, modified amino acid residue or an amino acid mimetic. Examples of conjugatable residues include, without limitation, lysine, cysteine, or a non-natural amino acid residue.

A skilled person would understand that, whether a residue is conjugatable residue would depend on the given conjugating reaction, and/or the functional group to be conjugated. For example, if the function group to be conjugated is a thiol group and/or the conjugation reaction is specific or selective for a thiol group, then lysine (i.e. having no functional thiol group in its side chain) would not be the conjugatable residue regardless of its position, whereas an unpaired cysteine residue that does not form a disulfide bond (whether intrachain bond or interchain bond), could be a conjugatable residue.

In certain embodiments, the polypeptide comprises a conjugatable residue for a conjugation reaction specific or selective for thiol group (for example, a maleimide reaction, or a reaction for disulfide bond formation). The expression "conjugatable" when referred to an amino acid residue is intended to mean that, the residue at a particular position in the polypeptide is sufficiently accessible for conjugation. For example, a cysteine residue as part of a disulfide bridge is not a conjugatable residue in the present disclosure.

In certain embodiments, the conjugatable residue is cysteine residue, preferably a free cysteine residue which is not part of a disulfide bridge.

In certain embodiments, the conjugatable residue CR in the FGF21 domain of the polypeptide provided herein can be at a position within a C-terminal fragment spanning of the FGF21 domain, e.g. from position 169 to position 181 relative to SEQ ID NO: 1. Further optionally, the conjugatable residue can be at a position selected from the group consisting of positions 169, 170, 171, 172, 173, 174, 180 and 181 relative to SEQ ID NO: 1. Without wishing to be bound by any theory, it is found by the present inventors that conjugation at C-terminal fragment of the FGF21 domain reduces the C-terminal degradation of the FGF21 domain.

In certain embodiments, the FGF21 domain in the polypeptide has a combination of mutations of: 1) N121Q and M168L, 2) N121Q, M168L and P171G, 3) N121Q, M168L and A180E, or 4) N121Q, M168L, P171G and A180E and further comprises a conjugatable residue (e.g. a cysteine residue) at position 169, 170, 171, 172, 173, 174, or 180, 181 relative to SEQ ID NO: 1.

In certain embodiments, the FGF21 domain in the polypeptide has a combination of mutations of N121Q and M168L, or a combination mutations of N121Q, M168L and P171G, and further comprises a conjugatable residue (e.g. a cysteine residue) at position 180 relative to SEQ ID NO: 1.

In certain embodiments, the FGF21 domain in the polypeptide has a combination of mutations of N121Q, P171G and M168L, or a combination mutations of N121Q, M168L, P171G and A180E, and further comprises a conjugatable residue at a position relative to SEQ ID NO: 1, listed as follows: introduced cysteine residue (e.g. via substitution) at position 169, position 170, position 172, position 173, or position 174.

In certain embodiments, the FGF21 domain in the polypeptide has an amino acid sequence comprising has an introduced cysteine residue at position 169 (e.g. SEQ ID NO: 6), position 170 (e.g. SEQ ID NO: 7), position 171 (e.g. SEQ ID NO: 8), position 172 (e.g. SEQ ID NO: 9), position 173 (e.g. SEQ ID NO: 10), position 174 (e.g. SEQ ID NO: 11, or SEQ ID NO: 92), position 180 (e.g. SEQ ID NO: 12), or position 181 (e.g. SEQ ID NO: 13). In certain embodiments, the FGF21 comprises the amino acid sequence of SEQ ID NOs: 2-5, 89-91, 14, and 102-105, except for one or more amino acid residue mutations, each at a position selected from positions 121, 168, 171, and 180 relative to SEQ ID NO: 1.

In certain embodiments, the FGF21 domain in the polypeptide has an introduced G at position 171 (e.g. SEQ ID NO: 14). Without wishing to be bound by any theory, it is found by the present inventors that introduction of 171G in the FGF21 domain could also be useful to reduce the C-terminal degradation of the FGF21 domain.

In certain embodiments, the FGF21 domain in the polypeptide have a combination of mutations of N121Q, P171G and M168L, or a combination mutations of N121Q, M168L, P171G and A180E, and further comprises a conjugatable residue at a position relative to SEQ ID NO: 1, listed as follows: an introduced T at position 172, position 173, position 174, wherein the position is relative to SEQ ID NO: 1; or introduced N at position 170 or position 174, wherein the position is relative to SEQ ID NO:1.

In certain embodiments, the FGF21 domain in the polypeptide has an introduced T at position 172 (e.g. SEQ ID NO: 16) or at position 173 (e.g. SEQ ID NO: 17); or an introduced N at position 170 (e.g. SEQ ID NO: 18) or at position 174 (e.g. SEQ ID NO: 19), relative to SEQ ID NO: 1. In certain embodiments, the FGF21 domain in the polypeptide has the amino acid sequence selected from the group consisting of SEQ ID NOs: 16-19.

Functional Moiety on the FGF21 Domain

In the first and the second embodiments of the polypeptide shown in FIG. 1A and FIG. 1B, either or both of the polypeptide 001A and 001B can optionally be conjugated with a functional moiety 800 at a conjugatable residue CR (as illustrated by the "*" in both figures) in the second fragment 200 (i.e. the FGF21 domain) to thereby form a polypeptide conjugate. In certain other embodiments, the polypeptide is not conjugated with the functional moiety, for example, when the polypeptide has an introduced G at position 171.

The term "conjugate" as used herein refers to a compound as a result of two or more molecules joined together to form one physical entity. For example, the polypeptide of the present disclosure can, according to certain embodiments, form a polypeptide conjugate, which is substantially a compound resulting from the polypeptide and a functional moiety being joined together. The molecules (e.g. the functional moiety and the polypeptide) may attach together by covalent bonds, non-covalent bonds, linkers, chemical modification, or protein fusion or by any means known to one skilled in the art. Preferably, the molecules may attach together by covalent bonds. The attachment may be permanent or reversible. In some embodiments, certain cleavable or non-cleavable linkers may be included.

The term "functional moiety" as used herein refers to a moiety that can functionally alter the biological, pharmacokinetic (PK), pharmacodynamic (PD) properties (e.g. to enhance the biological activity, to increase the stability in vitro, to increase the half-life in vivo, or to enhance the binding to target receptor, etc.). The functional moiety that is conjugated to the FGF2 domain may optionally comprise a glycosyl moiety or a synthetic chemical moiety.

Optionally, the functional moiety 800 can comprise a synthetic chemical moiety, and the conjugatable residue CR can be an introduced residue that can be conjugated with the synthetic chemical moiety.

According to some embodiments, the conjugatable residue CR can be an introduced cysteine residue, in any of the above mentioned positions 169, 170, 171, 172, 173, 174, 180 and 181 relative to SEQ ID NO: 1. Herein, the synthetic chemical moiety can optionally comprise a structure of *—X—Y—Z, wherein X, Y, and Z are interconnected via bonds, and the * end of X is connected to the conjugatable residue on the polypeptide. Herein, X can be

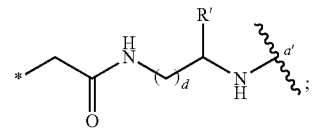

Y can be

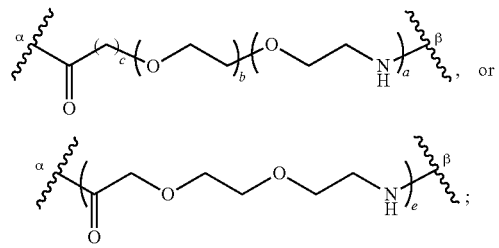

and Z can be

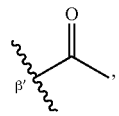

wherein position α is linked to position α', position β is linked to position β'. Herein, R1 can be hydrogen or —COOH; d can be 1, 2, or 3; a can be 1, 2 or 3; b can be 1, 2 or 3; c can be 1 or 2; and d can be 1, 2, or 3, and e can be 1, 2, or 3.

According to some embodiments, the synthetic chemical moiety can be Ac-2XADO-EDA-CO—CH$_2$*, where the * end is connected to the conjugatable cysteine residue on the polypeptide, having a structure of:

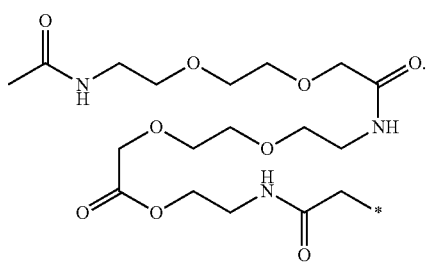 [SMILES: *CC(=O)NCCOC(=O)COCCOCCNC(=O)COCCOCCNC(C)=O]

In each of the above embodiments of the FGF21 domain comprising an introduced cysteine residue at their respective positions as indicated above whose sequences are set forth in SEQ ID NOs: 6-13 and 92, a synthetic chemical moiety, such as Ac-2XADO-EDA-CO—$CH_2$—* can be conjugated at the introduced cysteine residue (e.g. via substitution) to thereby obtain a polypeptide conjugate carrying the synthetic chemical moiety.

In the polypeptide carrying a conjugated functional moiety, the functional moiety 800 can optionally comprise a glycosyl moiety, and correspondingly, the conjugatable residue CR can be an introduced residue that is glycosylatable (i.e. can be glycosylated), which can be an introduced T at position 172 or position 173, or an introduced N residue at position 170 or position 174, relative to SEQ ID NO: 1.

In each of the above embodiments of the FGF21 domain comprising an introduced T or N at their respective positions as indicated above whose sequences are set forth in SEQ ID NOs: 16-19, a glycosyl moiety can be conjugated at the introduced cysteine residue to thereby obtain a polypeptide conjugate carrying the glycosyl moiety.

In certain embodiments of the FGF21 domain comprise an introduced G at position 171 relative to SEQ ID NO: 1, and is not conjugated with the functional moiety. In certain embodiments, such FGF21 domain can comprise an amino acid sequence of SEQ ID NO: 14.

Nanobody Domain

Each of the first and second embodiments of the polypeptide disclosed herein and illustrated in FIGS. 1A and 1B comprises the nanobody domain.

The term "nanobody" as used herein is considered to be exchangeable with "single-domain antibody", which refers to an antibody fragment containing a single variable domain of a heavy chain or a single variable domain of a light chain. A nanobody contains three complementarity determining regions (CDRs). In certain embodiments, the nanobody is capable of binding to a specific antigen (e.g., serum albumin).

The term "serum albumin" as used herein refers to an albumin (a type of globular protein) found in vertebrate blood. Serum albumin is produced by the liver, occurs dissolved in blood plasma and is the most abundant blood protein in mammals. Serum albumin typically has a half-life of around three weeks, which is mainly regulated by neonatal Fc receptor (FcRn). FcRn protects serum albumin from intracellular degradation by binding it with high affinity and diverting it from a lysosomal pathway, returning it to the extracellular compartment. In some embodiments, the serum albumin is selected from human serum albumin (HSA), cynomolgus monkeys serum albumin and mouse serum albumin. In some embodiments, the serum albumin provided herein is HSA.

The term "antibody" as used herein includes any immunoglobulin that binds to a specific antigen. Conventional antibody (e.g., antibodies from human or mice) comprises two heavy (H) chains and two light (L) chains. The heavy chains are classified as α, δ, ε, γ, and μ, each heavy chain consists of a variable domain (VH domain) and a first, second, third, and optionally fourth constant region (CH1, CH2, CH3, CH4 respectively); The light chains are classified as λ or κ, while each light chain consists of a variable domain (VL domain) and a constant domain. The antibody has a "Y" shape, with the stem of the Y consisting of the second and third constant domain of two heavy chains bound together via disulfide bonding. Each arm of the Y includes the variable domain and first constant domain of a single heavy chain bound to the variable and constant domains of a single light chain. The variable domains of the light and heavy chains are responsible for antigen binding. The variable domains in both chains generally contain three hypervariable regions called the complementarity determining regions (CDRs, namely CDR1, CDR2, and CDR3 of light chain or heavy chain). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., *J. Mol. Biol.*, 273 (4), 927 (1997); Chothia, C. et al., *J Mol Biol*. December 5; 186 (3): 651-63 (1985); Chothia, C. and Lesk, A. M., *J. Mol. Biol.*, 196,901 (1987); Chothia, C. et al., *Nature*. December 21-28; 342 (6252): 877-83 (1989); Kabat E. A. et al., Sequences of Proteins of immunological Interest, 5th Ed. Public Health Service, National Institutes of Health, Bethesda, Md. (1991); Marie-Paule Lefranc et al., *Developmental and Comparative Immunology*, 27:55-77 (2003); Marie-Paule Lefranc et al., *Immunome Research*, 1 (3), (2005); Marie-Paule Lefranc, Molecular Biology of B cells (second edition), chapter 26, 481-514, (2015)). The three CDRs are interposed between flanking stretches known as framework regions (FRs, namely FR1, FR2, FR3 and FR4 of light chain or heavy chain), which are more highly conserved than the CDRs and form a scaffold to support the highly variable loops. The constant domains of the heavy and light chains are not involved in antigen-binding, but exhibit various effector functions. Conventional antibodies are assigned to classes based on the amino acid sequences of the constant domains of their heavy chains.

The single variable domain can be derived from the variable domain of a camelid antibody (VHH domain), or the variable domain of cartilaginous fish antibody (VNAR domain). Both camelid antibodies and cartilaginous fish antibodies naturally lack light chains and consist of a pair of heavy chains. Alternatively, the single variable domain can be derived from the variable domain of a conventional antibody (e.g., from humans or mice) heavy chain (VH domain) or the variable domain of a common antibody light chain (VL domain). It is contemplated that a single domain antibody is fairly small in size, for example, has a molecular weight of no more than 25 kD, no more than 20 kD, no more than 15 kD, or no more than 10 kD.

It is to be noted that the term "nanobody" or "single-domain antibody" is used herein in its broadest sense and is not limited to a specific biological source or to a specific method of preparation. For example, a single domain antibody can be obtained, for example (1) by isolating the VHH domain or VNAR domain of a naturally occurring heavy chain antibody; (2) by expression of a nucleotide sequence encoding a naturally occurring VHH domain or VNAR domain; (3) by "humanization" (as described below) of a naturally occurring VHH domain or VNAR domain or by expression of a nucleic acid encoding a such humanized VHH domain or VNAR domain; (4) by "camelization" of a naturally occurring VH domain from any animal species, in particular a species of mammal, such as from a human being, or by expression of a nucleic acid encoding such a camelized VH domain; 5) using synthetic or semi-synthetic techniques for preparing proteins, polypeptides or other amino acid sequences; and/or (6) by any combination of the foregoing. Suitable methods and techniques for performing the foregoing will be clear to the skilled person.

In some embodiments, the single domain antibody described herein comprises a VHH domain derived from antibodies raised in Camelidae species, for example in camel, dromedary, alpaca and guanaco. A single domain antibody comprising a VHH domain are highly soluble and highly stable to heat, pH, proteases and other denaturing agents or conditions.

In some embodiments, the first polypeptide fragment comprises one or more single domain antibody that is capable of specifically binding to serum albumin.

The term "binding specificity", "specific binding" or "specifically binds" in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. Antibodies or fragments thereof that immunospecifically bind to an antigen may be cross-reactive with related antigens, carrying the same epitope. The "binding specificity" is generally measured against nonspecific background binding. Typically, an antibody is considered specific when it binds to the target antigen at least 10 times above background binding.

The serum binding single domain antibody contemplated herein can bind to or otherwise associate with serum albumin in such a way that the binding of said serum albumin molecule to FcRn is not (significantly) reduced or inhibited (i.e. compared to the binding of said serum albumin molecule to FcRn when the single domain antibody is not bound thereto). In this aspect of the invention, by "not significantly reduced or inhibited" is meant that the binding affinity for serum albumin to FcRn (as measured using a suitable assay, such as SPR) is not reduced by more than 50%, preferably not reduced by more than 30%, even more preferably not reduced by more than 10%, such as not reduced by more than 5%, or essentially not reduced at all. In this aspect "not significantly reduced or inhibited" may also mean that the half-life of the serum albumin molecule is not significantly reduced (e.g., is not reduced by more than 50%, preferably not reduced by more than 30%, even more preferably not reduced by more than 10%, such as not reduced by more than 5%, or essentially not reduced at all, as measured using a suitable technique known per se). In some embodiments, the single domain antibody are capable of binding to amino acid residues on serum albumin that are not involved in binding of serum albumin to FcRn.

In some embodiments, the single domain antibody described herein binds to serum albumin selected from HSA, cynomolgus monkeys serum albumin and mouse serum albumin. In some embodiments, the binding affinity towards mouse serum albumin is about weaker than that towards human or cynomolgus serum albumin. In some embodiments, the single domain antibody specifically binds to HSA.

In some embodiments, the single domain antibody described herein binds to serum albumin with sufficient binding affinity. The term "affinity" as used herein refers to the strength of non-covalent interaction between an immunoglobulin molecule (i.e. antibody) or fragment thereof and an antigen. Affinity can be expressed numerically using "Kd" values. In general, a lower Kd value corresponds to a stronger binding. Kd may be determined by using any conventional method known in the art, including but are not limited to radioimmunoassays (RIA), enzyme-linked immunosorbent assays (ELISA), surface plasmon resonance (SPR) method, microscale thermophoresis method, HPLC-MS method and flow cytometry (such as FACS) method. In some embodiment, the antibody disclosed here has a $K_d$ value of $\leq 10^{-6}$ M (e.g. $\leq 5\times 10^{-7}$ M, $\leq 2\times 10^{-7}$M, $\leq 10^{-7}$M, $\leq 5\times 10^{-8}$ M, $\leq 2\times 10^{-8}$ M, $\leq 10^{-8}$ M, $\leq 5\times 10^{-9}$ M, $\leq 4\times 10^{-9}$M, $\leq 3\times 10^{-9}$M, $\leq 2\times 10^{-9}$ M, or $\leq 10^{-9}$ M) with the specific antigen.

In certain embodiments, the single domain antibody provided herein are capable of binding to HSA at a Kd value of $10^{-5}$M to $1\times 10^{-12}$M or less, of $10^{-7}$M to $1\times 10^{-12}$M or less, or of $10^{-8}$M to $1\times 10^{-12}$M or less. In some embodiments, the Kd is no more than $1\times 10^{-7}$M (e.g. no more than $5\times 10^{-7}$ M, no more than $2\times 10^{-7}$ M, no more than $10^{-7}$ M, no more than $5\times 10^{-8}$ M, no more than $2\times 10^{-8}$ M, no more than $10^{-8}$ M, no more than $5\times 10^{-9}$ M, no more than $4\times 10^{-9}$M, no more than $3\times 10^{-9}$M, no more than $2\times 10^{-9}$ M, or no more than $10^{-9}$ M).

In some embodiments, the single domain antibody provided herein is a humanized antibody. The term "humanized" as used herein means that the single domain antibody comprises CDRs derived from a non-human animal, and FR regions derived from human. A humanized antibody polypeptide is desirable in its reduced immunogenicity in human. A humanized antibody polypeptide is chimeric in its variable regions, as non-human CDR sequences are grafted to human or substantially human FR sequences. Humanization of an antibody polypeptide can be essentially performed by substituting the non-human (such as camelid) CDR genes for the corresponding human CDR genes in a human immunoglobulin gene (see, for example, Jones et al. (1986) Nature 321:522-525; Riechmann et al. (1988) Nature 332:323-327; Verhoeyen et al. (1988) Science 239:1534-1536).

Various single domain antibodies that are capable of specifically binding to HSA with a high affinity are known in the art, such as fully human domain antibodies isolated using phase display, VHH antibodies developed form camelidae family, and VNAR antibodies developed from cartilaginous fish, see Zorzi, A et al, Med Chem Commun, 2019, 10, 1068. Exemplary HSA-binding single domain antibodies are disclosed in U.S. Pat. No. 8,188,223B2, U.S. Pat. No. 9,067,991B2, U.S. Pat. No. 9,321,832B2, PCT application WO2008028977A2, WO2008043822A2, WO2020099871A1, G. Winter, et al, Annu. Rev. Immunol., 1994, 12, 433-455, L. J. Holt, et al., Protein Eng., Des. Sel., 2008, 21 (5), 283-288, A. Walker, et al., Protein Eng., Des. Sel., 2010, 23 (4), 271-278, L. J. Goodall, et al., PLOS One, 2015, 10 (9), e0137065, R. L. O'Connor-Semmes, et al., Clin. Pharmacol. Ther., 2014, 96 (6), 704-712, C. Read, et al., Basic Clin. Pharmacol. Toxicol., 2019, 1-8, R. Adams, et al., mAbs, 2016, 8 (7), 1336-1346, E. Dave, et al., mAbs, 2016, 8 (7), 1319-1335, S. Steeland, et al., Drug Discovery Today, 2016, 21 (7), 1076-1113, K. Coppieters, et al., Arthritis Rheum., 2006, 54 (6), 1856-1866, M. Van Roy, et al., Arthritis Res. Ther., 2015, 17, 135, C. McMahon, et al., Nat. Struct. Mol. Biol., 2018, 25 (3), 289-296, M. R. Muller, et al., mAbs, 2012, 4 (6), 673-685, all of which are contemplated within the scope of the disclosure and incorporated by reference.

In some embodiments, the single domain antibody comprises a VHH domain. In some embodiments, the VHH domain is humanized.

In some embodiments, the VHH domain comprises a complementarity determining region 1 (CDR1), CDR2 and CDR3, wherein the CDR1 comprises the sequence of SEQ ID NO: 20 (SFGMS) or a variant thereof having up to 3, 2, or 1 amino acid mutation, a CDR2 comprising the sequence of SEQ ID NO: 21 (SISGSGSDTLYADSVKG) or a variant thereof having up to 3, 2, or 1 amino acid mutation, and/or a CDR3 comprising the sequence of SEQ ID NO: 22 (GGSLSR) or a variant thereof having up to 3, 2, or 1 amino acid mutation, wherein the VHH domain retains the binding specificity to serum albumin, optionally to human serum albumin.

In some embodiments, the VHH domain comprises a complementarity determining region 1 (CDR1) comprising the sequence of SEQ ID NO: 20, a CDR2 comprising the sequence of SEQ ID NO: 21, and a CDR3 comprising the sequence of SEQ ID NO: 22.

In some embodiments, the VHH domain comprises a complementarity determining region 1 (CDR1) consisting of the sequence of SEQ ID NO: 20, a CDR2 consisting of the sequence of SEQ ID NO: 21, and a CDR3 consisting of the sequence of SEQ ID NO: 22.

In some embodiments, the VHH domain comprises the sequence of SEQ ID NO: 23, or a variant thereof having at least 70% (e.g. at least 75%, 80%, 85%, 90%, 95%, 99% identity to SEQ ID NO: 23, wherein the variant retains the binding specificity and/or affinity to serum albumin.

In some embodiments, the variant of SEQ ID NO: 23 has up to 10, 9, 8, 7, 6, 5, 4, 3, 2, or 1 amino acid mutation relative to SEQ ID NO: 23.

In certain embodiments of the polypeptide illustrated in FIG. 1A, the serum albumin binding nanobody domain further comprises an N-terminal extension attached to the VHH domain. In certain embodiments, the N-terminal extension comprises amino acid residues of SG, AG, S or A, and thus may comprise an amino acid sequence selected from SEQ ID NOs: 24-27.

In certain embodiments, the N-terminal extension comprises a tag, optionally a cleavable tag. Without wishing to be bound by any theory, it is believed that certain N-terminal extension can be useful for expression and post-translational processing.

In certain embodiments, the serum albumin-binding nanobody domain does not comprise an N-terminal extension attached to the VHH domain. For example, the VHH domain can be attached to a cleavable tag which, after cleavage, is no longer present in the final product.

In some embodiments, the first fragment may comprise one or more serum albumin binding nanobody domains.

GLP-1 Domain

The second embodiments of the polypeptide disclosed herein and illustrated in FIG. 1B further comprises, in addition to the above described FGF21 domain in the second fragment 200 and the serum albumin binding nanobody domain in the first fragment 100, a third fragment 300 comprising an additional functional domain.

According to some embodiments, the additional functional domain comprises a biologically active GLP-1 domain.

The term "Glucagon-like peptide-1" or "GLP-1" as used herein is intended to broadly encompasses native GLP-1 peptide and all its functional forms such as its functional variants, fragments, fusions, derivatives and mimetics.

The term "native GLP-1 peptide" as used herein refers to the native human Glucagon-Like Peptide-1 (GLP-1 (7-37)), the sequence of which is set forth in SEQ ID NO: 28. The numbering of the residues in GLP-1 is referred to the sequence of SEQ ID NO: 28, which begins with the H residue at position 7 and ends with the G residue at position 37.

A functional form of the native GLP-1 peptide is capable of activating the GLP-1 receptor at a level comparable to, or no less than about 20% (or no less than 30%, 40%, 50%, 60%, 70%, 80%, 90%) of, that of the native GLP-1 peptide. Activation of the GLP-1 receptor typically initiates signal transduction pathway resulting in insulinotropic action or other physiological effects as is known in the art. Many functional forms of GLP-1 peptide are known in the art, for example, without limitation, liraglutide, semaglutide, dulaglutide, albiglutide, and those disclosed in WO2000055203A1, WO 98/08871, WO 2006/097537, WO2007139589A1, WO1998019698A1, WO2001098331A2, WO2003040309A2, WO2005000892A2, WO2015000942A1, WO2016083499A1 the disclosure of which is incorporated herein to its entirety.

In certain embodiments, the GLP-1 domain provided herein comprises an amino acid sequence having at least 70% (e.g. at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%) sequence identity to SEQ ID NO: 28 while retaining substantial biological activity of SEQ ID NO: 28.

In certain embodiments, the GLP-1 domain comprises no more than 9, 8, 7, 6, 5, 4, 3, or 2 substitutions relative to SEQ ID NO: 28 while retaining substantial biological activity of SEQ ID NO: 28. In certain embodiments, the GLP-1 domain comprises at least 2, 3, 4, 5, 6, 7, 8, or 9 substitutions relative to SEQ ID NO: 28 while retaining substantial biological activity of SEQ ID NO: 28.

In certain embodiments, the GLP-1 domain further comprises one or more mutations. One of ordinary skill in the art will appreciate that various amino acid substitutions, e.g., conservative amino acid substitutions, may be made in the sequence of any of the polypeptide described herein, without necessarily decreasing its activity. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-national amino acids having an amino containing side chain, or substituting an alanine for norvaline or the like.

Various substitutions have been introduced to native GLP-1 peptide, and have been shown to be capable of retaining or even improving its biological activities. In certain embodiments, the GLP-1 comprises one or more mutations at a position selected from the group consisting of: A8, G22, K34, R36, and H7, and or any combination thereof, relative to SEQ ID NO: 28. For example, it is believed that substitution at A8 is useful to prevent DPP4 enzymatic cleavage at the residue, substitution at G22 is desirable to improve activity and solubility, and substitution at R36 is useful to reduce immunogenicity. In certain embodiments, the GLP-1 comprises one or more mutations at a position selected from the group consisting of: A8, G22, K26, K34, and R36, and or any combination thereof, relative to SEQ ID NO: 28. Examples of substitutions at these positions include, without limitation, A8G, A8S, A8V, A8Aib, A8T, A8I, A8L, G22E, K26R, K34R, R36G, or any combination thereof, as well as the substitutions described in U.S. Pat. No. 8,273,854, which are incorporated herein by its entirety. In certain embodiments, the one or more additional substitutions comprises a conservative substitution.

In certain embodiments, the GLP-1 domain comprises a substitution of A8 which is selected from the group consisting of: A8G, A8S, A8V, A8Aib, A8T, and A8L. In certain embodiments, the GLP-1 domain comprises a substitution of G22E. In certain embodiments, the GLP-1 domain comprises n substitution of R36G. In certain embodiments, the GLP-1 domain comprises a substitution of K26 which is K26R. In certain embodiments, the GLP-1 domain comprises a substitution of K34 which is K34R.

In certain embodiments, the GLP-1 comprises or consists of one or more substitutions selected from the group consisting of A8G, K26R, K34R, G22E, and R36G. In certain embodiments, the GLP-1 comprises or consists of one or more substitutions selected from the group consisting of A8G, G22E, and R36G.

In the present disclosure, at least the following embodiments of the biologically active GLP-1 domain in the third fragment 300 in FIG. 1B are provided:

(1) SEQ ID NO: 28, representing a wildtype functional form of GLP-1;
(2) SEQ ID NO: 29, representing a three-substitution functional form of GLP-1 comprising substitutions A8G, G22E, and R36G;
(3) SEQ ID NO: 31, representing a four-substitution functional form of GLP-1 comprising substitutions A8G, G22E, K34R, and R36G;
(4) SEQ ID NO: 32, representing a five-substitution functional form of GLP-1 comprising substitutions A8G, G22E, K26R, K34R, and R36G;
(4) SEQ ID NO: 33, representing a five-substitution functional form of GLP-1 comprising substitutions A8G, G22E, K26R, K34R, and R36K; and
(5) SEQ ID NO: 34, representing a four-substitution functional form of GLP-1 comprising substitutions A8G, G22E, K26R, and R36G.

It is to be noted that in addition to GLP-1, the additional functional domain of the third fragment 300 as illustrated in FIG. 1B may alternatively comprise a biologically active form (i.e. functional form) of insulin, C-peptide, leptin, glucagon, gastrin, gastric inhibitory polypeptide (GIP), amylin, calcitonin, cholecystokinin, peptide YY, neuropeptide Y, bone morphogenetic protein-6 (BMP-6), bone morphogenetic protein-9 (BMP-9), oxyntomodulin, oxytocin, glucagon-like peptide-2 (GLP-2), irisin, fibronectin type III domain containing protein 5 (FNDC5), apelin, adiponectin, C1q and tumor necrosis factor related protein (CTRP family), resistin, visfatin, omentin, retinol binding protein-4 (RBP-4), glicentin, angiopoietin, interleukin-22 (IL-22), exendin-4, or growth hormone.

The First and/or Second Linker

Each of the first and second embodiments of the polypeptide disclosed herein and illustrated in FIGS. 1A and 1B utilizes the first linker 10 to connect the first fragment 100 (comprising the nanobody domain capable of binding to serum albumin) and the second fragment 200 (comprising the biologically active FGF21 domain), and the second embodiments of the polypeptide illustrated in FIG. 1B utilizes the second linker 20 to connect the first fragment 100 and the third fragment 300 (comprising a biologically active additional functional domain that has additive or synergistic effect on FGF21 domain; e.g. GLP-1 domain).

The term "linker" as used herein, such as the first linker 10 and/or the second linker 20, refers generally to a "polypeptide linker", which can be any suitable polypeptide capable of bonding two entities to thereby form one molecule, or maintaining association of the two entities in sufficiently close proximity, yet without substantially interference to the respective biological activities of the two entities.

The linker can be integrated in the resulting linked molecule or structure. Herein, the first linker 10 operably separates the nanobody domain 100 and the FGF21 domain 200 without substantial interference to the respective biological activities of the two functional domains, and the second linker 20 operably separates the GLP-1 domain and the nanobody domain 100 without substantial interference to the respective biological activities of the two functional domains. The linker can be made up of amino acid residues linked together by peptide bonds, yet may optionally further comprise one or more non-natural amino acids.

Generally, each of the first linker 10 and the second linker 20 has a length of at least four amino acid residues. As such, in certain embodiments, each linker has a length of at least 4, 8, 10, 20, 24, 28, 30, 40, 48, 50, 60, 70, 80, 90, 100, 110, 120 or more amino acid resides. Without wishing to be bound by any theory, it is believed that a suitable length of a linker can further improve the biological activity, stability, or pharmacokinetic parameters of the each of the two functional domains such linked thereby in the whole polypeptide molecule.

Any suitable polypeptide can be used as a linker. For example, the polypeptide linker may comprise or consist of amino acid residues selected from the amino acids glycine (G), serine(S), alanine (A), methionine (M), asparagine (N), glutamine (Q), cysteine (C), Proline (P), Glutamate (E), Threonine (T) and lysine (K). In some embodiments, the polypeptide linker can be made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly (Gly-Ser)).

In certain embodiments, each of the first linker and the second linker comprises or consists of one or more repeats of a repeating sequence. In certain embodiments, the polypeptide linker comprises or consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 repeats of a repeating sequence, or within any numerical range defined by any two numbers listed above.

Herein, based on the experimental data shown in the Examples below, the following configurations are provided which are nonetheless optional and non-limiting in scope.

Regarding the first linker, it may comprise no acidic amino acid residue (e.g. D or E) according to some embodiments. The first linker may optionally comprise one or more units of a first repeating sequence, and the first repeating sequence may consist of no more than 4 or 6 types of amino acid residues, which can be selected from the group consisting of: G, Q, A, P, T and S. According to some embodiments of the polypeptide, the first repeating sequence comprises or consists of an amino acid sequences selected from a group consisting of $G_fS_g$ (each of f and g is independently an integer selected from 1 to 5), SEQ ID NO: 35 (GAQP), SEQ ID NO: 36 (GQAP), SEQ ID NO: 37 (GPAQ), SEQ ID NO: 38 (GPQA), SEQ ID NO: 39 (GSQP), SEQ ID NO: 40 (GASP), SEQ ID NO: 41 (GPAS), SEQ ID NO: 42 (GPSA), SEQ ID NO: 43 (GGGS), SEQ ID NO: 44 (GSGS), SEQ ID NO: 45 (GGGGS), SEQ ID NO: 46 (GSAPGSPAGSPTGSAPGSPA) and SEQ ID NO: 110 (GS). In certain embodiments of the polypeptide, the first repeating sequence has an amino acid sequence set forth in SEQ ID NO: 35 (GAQP), and a number of the one or more units is an integer between 1 and 10. In certain embodiments, the first linker comprises an amino acid sequence selected from the group consisting of SEQ ID NO: 35 (GAQP), SEQ ID NO: 49 ((GAQP) 2), SEQ ID NO: 50 ((GAQP) 5), SEQ ID NO: 51 ((GAQP) 10), and SEQ ID NO: 48 (GGGGSGGGS).

Regarding the second linker, it may similarly comprise one or more units of a second repeating sequence, and the second repeating sequence may consist of no more than 4 or 6 types of amino acid residues selected from the group consisting of: G, Q, A, E, P, T and S. In certain embodiments of the polypeptide, the second repeating sequence comprises or consists of an amino acid sequences selected from a group consisting of $G_hS_i$ (each of h and i is independently an integer selected from 1 to 5), SEQ ID NO: 35 (GAQP), SEQ ID NO:55 (GQEP), SEQ ID NO: 56 (GEQP), SEQ ID NO: 57 (GPQE), SEQ ID NO: 58 (GPEQ), SEQ ID NO: 59 (GSEP), SEQ ID NO: 60 (GESP), SEQ ID NO: 61 (GPSE), SEQ ID NO: 62 (GPES), SEQ ID NO: 36 (GQAP), SEQ ID NO: 37 (GPAQ), SEQ ID NO: 38 (GPQA), SEQ ID NO: 39 (GSQP), SEQ ID NO: 40 (GASP), SEQ ID NO: 41 (GPAS), SEQ ID NO: 42 (GPSA), SEQ ID NO: 43 (GGGS), SEQ ID NO: 44 (GSGS), SEQ ID NO: 45 (GGGGS), SEQ ID NO: 46 (GSAPGSPAGSPTGSAPGSPA) and SEQ ID NO: 110 (GS). In certain embodiments, the second repeating sequence has an amino acid sequence set forth in SEQ ID NO: 35 (GAQP), and a number of the one or more units is an integer between 1 and 15, optionally 1, 2, 5, 10, or 14. In certain embodiments, the second linker comprises an amino acid sequence selected from the group consisting of SEQ ID NO: 49 ((GAQP)$_2$), SEQ ID NO: 50 ((GAQP)$_5$), SEQ ID NO: 51 ((GAQP)$_{10}$), and SEQ ID NO: 52 ((GAQP)$_{14}$), and SEQ ID NO: 47 ((GGGGS)$_4$).

In certain embodiments, each of the first linker and the second linker may comprise or consist of more than one repeating sequence. For example, one such linker may comprise or consist of 2, 3, or 4 different repeating sequences. In certain embodiments, one such linker may comprise or consist of sequential or tandem repeats of the different repeating sequences. The number of repeats of each repeating sequence more be independently selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more.

Other Notes

The following is noted for each of the FGF21 domain, the nanobody domain, the GLP-1 domain, and the first/second linker as described above. One of ordinary skill in the art will appreciate that various amino acid substitutions, e.g., conservative amino acid substitutions, may be made in the sequence of any of the polypeptide fragment described herein, without necessarily decreasing its activity. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-national amino acids having an amino containing side chain, or substituting an alanine for norvaline or the like.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The following full-length sequences are provided for certain embodiments of the first embodiments (illustrated in FIG. 1A) and of the second embodiments (illustrated in FIG. 1B).

Certain embodiments of the polypeptide is substantially a fusion polypeptide between a serum albumin-binding nanobody domain and an FGF21 domain in an N-terminus-to-C-terminus direction, and may have an amino acid sequence that is selected from SEQ ID NOS: 63-68, 93, 99-101 and 107. In certain of these embodiments, the polypeptide is conjugated to a synthetic chemical moiety provided herein (see, e.g. based on FIG. 1A). The synthetic chemical moiety, for example, can be Ac-2XADO-EDA-CO—CH2-*, which is conjugated with an introduced cysteine residue at position 171 or position 174 relative to SEQ ID NO: 1 for a polypeptide with a sequence selected from the group consisting of SEQ ID NOS: 63, 68, 93 and 100. In certain of the alternative embodiments, the polypeptide comprises an amino acid sequence selected from the group consisting of SEQ ID NOS: 64-67, 69, 99 and 108, and is not conjugated.

Table 1A below shows the SEQ ID NOs of the exemplary fusion polypeptide sequences, and the SEQ ID NOs for the nanobody, the FGF21, and the first polypeptide linker and the second polypeptide linker contained in the fusion polypeptides.

TABLE 1A

Exemplary fusion polypeptide sequences

| Molecule Code. (MLC) | Fusion Polypeptide | Nanobody | First Linker | FGF21 (Mutations#) | Conjugation site; functional moiety |
|---|---|---|---|---|---|
| MLC#1 | SEQ ID NO: 63 | SEQ ID NO: 27 | (GAQP)10 (SEQ ID NO: 51) | 121Q, 168L, 171C, 180E (SEQ ID NO: 8) | 171C; Moiety A## |
| MLC#2 | SEQ ID NO: 64 | SEQ ID NO: 27 | (GAQP)10 (SEQ ID NO: 51) | 121Q, 168L, 171G, 180E (SEQ ID NO: 14) | No |

TABLE 1A-continued

Exemplary fusion polypeptide sequences

| Molecule Code. (MLC) | Fusion Polypeptide | Nanobody | First Linker | FGF21 (Mutations#) | Conjugation site; functional moiety |
|---|---|---|---|---|---|
| MLC#3 | SEQ ID NO: 65 | SEQ ID NO: 27 | (GAQP)5 (SEQ ID NO: 50) | 121Q, 168L, 171G, 180E (SEQ ID NO: 14) | No |
| MLC#4 | SEQ ID NO: 66 | SEQ ID NO: 27 | (GAQP)2 (SEQ ID NO: 49) | 121Q, 168L, 171G, 180E (SEQ ID NO: 14) | No |
| MLC#5 | SEQ ID NO: 67 | SEQ ID NO: 27 | (GAQP) (SEQ ID NO: 35) | 121Q, 168L, 171G, 180E (SEQ ID NO: 14) | No |
| MLC#6 | SEQ ID NO: 68 | SEQ ID NO: 27 | (GAQP) (SEQ ID NO: 35) | 121Q, 168L, 171C, 180E (SEQ ID NO: 8) | 171C; Moiety A## |
| MLC#7 | SEQ ID NO: 93 | SEQ ID NO: 27 | (GAQP) (SEQ ID NO: 35) | 121Q, 168L, 171G, 174C, 180E (SEQ ID NO: 92) | 174C; Moiety A## |
| MLC#22 | SEQ ID NO: 99 | SEQ ID NO: 27 | (GAQP) (SEQ ID NO: 35) | 121Q, 168L, 180E (SEQ ID NO: 5) | No |
| MLC#23 | SEQ ID NO: 100 | SEQ ID NO: 27 | G4S (SEQ ID NO: 45) | 121Q, 168L, 171C, 180E (SEQ ID NO: 8) | 171C; Moiety A## |
| MLC#25 | SEQ ID NO: 101 | SEQ ID NO: 27 | G4S (SEQ ID NO: 45) | 121Q, 168L, 180E (SEQ ID NO: 5) | No |
| MLC#26 | SEQ ID NO: 107 | SEQ ID NO: 27 | G4S (SEQ ID NO: 45) | 121Q, 168L, 171G, 180E (SEQ ID NO: 14) | No |

: the mutation positions are relative to SEQ ID NO: 1.

Moiety A refers to Ac-2XADO-EDA-CO—CH$_2$*, where the * end is connected to the conjugatable cysteine residue on the polypeptide, having a structure of:

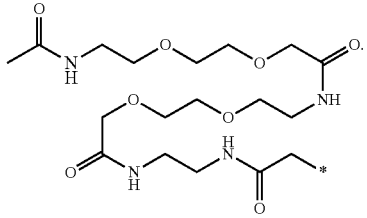 [SMILES: *CC(=O)NCCNC(=O)COCCOCCNC(=O)COCCOCCNC(C)=O]

Certain embodiments of the polypeptide is substantially a fusion polypeptide among a GLP-1 domain, a serum albumin-binding nanobody domain, and an FGF21 domain in an N-terminus-to-C-terminus direction, which may have an amino acid sequence that is selected from SEQ ID NOS: 70, 74, 75, 79-83, 85, 94-98 and 108-109. In certain of these embodiments, the polypeptide is conjugated to a synthetic chemical moiety as provided herein (see, e.g., based on FIG. 1B). The synthetic chemical moiety, for example, can be Ac-2XADO-EDA-CO—CH2-*, which is conjugated with an introduced cysteine residue at position 171 or position 174 relative to SEQ ID NO: 1 for the amino acid sequences selected from the group consisting of SEQ ID NOs: 74, 81-83, 85, 94, 96 and 97. In certain of the alternative embodiments, the polypeptide comprises an amino acid sequence selected from SEQ ID NOs: 70, 75, 79, 80, 95, 98, and 108-109, and is not conjugated.

Table 1B below shows the SEQ ID NOs of the exemplary fusion polypeptide sequences, and the SEQ ID NOs for the GLP-1 domain, the first polypeptide linker, nanobody, the FGF21 domain, and the first polypeptide linker and the second polypeptide linker contained in the fusion polypeptides.

TABLE 1B

Exemplary fusion polypeptide sequences

| Molecule Code. (MLC); Fusion Polypeptide (SEQ ID NO) | GLP1 domain (Mutations&) | Second linker | Nanobody | First Linker | FGF21 domain (Mutations#) | Conjugation site; functional moiety |
|---|---|---|---|---|---|---|
| MLC#8 (SEQ ID NO: 70) | 8G, 22E, 36G (SEQ ID NO: 29) | (G4S)4 (SEQ ID NO: 47) | SEQ ID NO: 27 | G4SG3S (SEQ ID NO: 48) | 121Q, 168L, 171G, 180E (SEQ ID NO: 14) | No |
| MLC#9 (SEQ ID NO: 74) | 8G, 22E, 36G (SEQ ID NO: 29) | (GAQP)5 (SEQ ID NO: 50) | SEQ ID NO: 27 | (GAQP)10 (SEQ ID NO: 51) | 121Q, 168L, 171C, 180E (SEQ ID NO: 8) | 171C; Moiety A## |
| MLC#10 (SEQ ID NO: 75) | 8G, 22E, 36G (SEQ ID NO: 29) | (GAQP)5 (SEQ ID NO: 50) | SEQ ID NO: 27 | (GAQP)10 (SEQ ID NO: 51) | 121Q, 168L, 171G, 180E (SEQ ID NO: 14) | No |
| MLC#11 (SEQ ID NO: 79) | 8G, 22E, 36G (SEQ ID NO: 29) | (GAQP)10 (SEQ ID NO: 51) | SEQ ID NO: 27 | (GAQP)10 (SEQ ID NO: 51) | 121Q, 168L, 171G, 180E (SEQ ID NO: 14) | No |
| MLC#12 (SEQ ID NO: 80) | 8G, 22E, 36G (SEQ ID NO: 29) | (GAQP)5 (SEQ ID NO: 50) | SEQ ID NO: 27 | (GAQP) (SEQ ID NO: 35) | 121Q, 168L, 171G, 180E (SEQ ID NO: 14) | No |
| MLC#13 (SEQ ID NO: 81) | 8G, 22E, 36G (SEQ ID NO: 29) | (GAQP)5 (SEQ ID NO: 50) | SEQ ID NO: 27 | (GAQP) (SEQ ID NO: 35) | 121Q, 168L, 171C, 180E(SEQ ID NO : 8) | 171C; Moiety A## |
| MLC#14 (SEQ ID NO: 82) | 8G, 22E, 36G (SEQ ID NO: 29) | (GAQP)10 (SEQ ID NO: 51) | SEQ ID NO: 27 | (GAQP) (SEQ ID NO: 35) | 121Q, 168L, 171C, 180E (SEQ ID NO: 8) | 171C; Moiety A## |
| MLC#15 (SEQ ID NO: 83) | 8G, 22E, 36G (SEQ ID NO: 29) | (GAQP)2 (SEQ ID NO: 49) | SEQ ID NO: 27 | (GAQP) (SEQ ID NO: 35) | 121Q, 168L, 171C, 180E (SEQ ID NO: 8) | 171C; Moiety A## |
| MLC#16 (SEQ ID NO: 85) | 8G, 22E, 36G (SEQ ID NO: 29) | (GAQP)14 (SEQ ID NO: 52) | SEQ ID NO: 27 | (GAQP) (SEQ ID NO: 35) | 121Q, 168L, 171C, 180E (SEQ ID NO: 8) | 171C; Moiety A## |
| MLC#17 (SEQ ID NO: 94) | 8G, 22E, 36G (SEQ ID NO: 29) | (GAQP)14 (SEQ ID NO: 52) | SEQ ID NO: 27 | (GAQP) (SEQ ID NO: 35) | 121Q, 168L, 171G, 174C, 180E (SEQ ID NO : 92) | 174C; Moiety A## |
| MLC#18 (SEQ ID NO: 95) | 8G,22E, 36G (SEQ ID NO: 29) | (GAQP)14 (SEQ ID NO: 52) | SEQ ID NO: 27 | (GAQP) (SEQ ID NO: 35) | 121Q, 168L, 180E (SEQ ID NO: 5) | No |
| MLC#19 (SEQ ID NO: 96) | 8G,22E, 36G (SEQ ID NO: 29) | (GAQP)14 (SEQ ID NO: 52) | SEQ ID NO: 27 | (G4S) (SEQ ID NO: 45) | 121Q, 168L, 171C, 180E (SEQ ID NO: 8) | 171C; Moiety A## |
| MLC#20 (SEQ ID NO: 97) | 8G,22E, 36G (SEQ ID NO: 29) | (GAQP)13 (G4S) (SEQ ID NO: 106) | SEQ ID NO: 27 | (G4S) (SEQ ID NO: 45) | 121Q, 168L, 171C, 180E (SEQ ID NO: 8) | 171C; Moiety A## |
| MLC#21 (SEQ ID NO: 98) | 8G,22E, 36G (SEQ ID NO: 29) | (GAQP)14 (SEQ ID NO: 52) | SEQ ID NO: 27 | (G4S) (SEQ ID NO: 45) | 121Q, 168L, 180E (SEQ ID NO: 5) | No |
| MLC#27 (SEQ ID NO: 108) | 8G,22E, 36G (SEQ ID NO: 29) | (GAQP)14 (SEQ ID NO: 52) | SEQ ID NO: 27 | (GAQP) (SEQ ID NO: 35) | 121Q, 168L, 171G, 180E (SEQ ID NO: 14) | No |
| MLC#28 (SEQ ID NO: 109) | 8G,22E, 36G (SEQ ID NO: 29) | (GAQP)14 (SEQ ID NO: 52) | SEQ ID NO: 27 | (G4S) (SEQ ID NO: 45) | 121Q, 168L, 171G, 180E (SEQ ID NO: 14) | No |

&: the mutation positions are relative to SEQ ID NO: 28.
: the mutation positions are relative to SEQ ID NO: 1.
Moiety A refers to Ac-2XADO-EDA-CO—CH$_2$*, where the * end is connected to the conjugatable cysteine residue on the polypeptide, having a structure of:

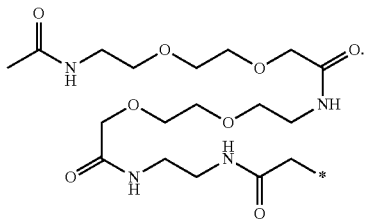 [SMILES: *CC(=O)NCCNC(=O)COCCOCCNC(=O)COCCOCCNC(C)=O]

Pharmaceutical Composition

In another aspect, the present disclosure further provides a pharmaceutical composition, which comprises the polypeptide according to any of the embodiments as described above, and a pharmaceutically acceptable carrier.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

A "pharmaceutically acceptable carrier" refers to an ingredient in a pharmaceutical formulation, other than an active ingredient, which is bioactivity acceptable and non-toxic to a subject. Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a pharmaceutical composition provided herein decreases oxidation of the polypeptide complex or the bispecific polypeptide complex. This reduction in oxidation prevents or reduces loss of binding affinity, thereby improving protein stability and maximizing shelf-life. Therefore, in certain embodiments, compositions are provided that comprise the polypeptide, the polypeptide complex or the conjugate disclosed herein and one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving the polypeptide, the polypeptide complex or the conjugate as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the polypeptide, the polypeptide complex, or the conjugate provided herein or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Administration of the pharmaceutical composition as described herein may be via any route known to be effective by the physician of ordinary skill. One example is peripheral parenteral administration by a sterile syringe or some other mechanical device such as an infusion pump. In certain embodiments, peripheral parenteral route is intravenous, intramuscular, subcutaneous, or intraperitoneal routes of administration.

In certain embodiments, the polypeptide, the polypeptide complex, or the conjugate described herein is formulated in a form suitable for non-parenteral routes administration, such as oral, rectal, nasal, or lower respiratory routes administration.

In certain embodiments, the polypeptide, the polypeptide complex, or the conjugate described herein is formulated in a solid formulation such as lyophilization or spray drying, which is then reconstituted in a suitable diluent solution prior to administration. Standard pharmaceutical formulation techniques, such as those described in Remington: The Science and Practice of Pharmacy (D. B. Troy, Editor, 21st Edition, Lippincott, Williams & Wilkins, 2006), may be employed. Alternatively, the polypeptide, the polypeptide complex, or the conjugate described herein can be formulated for administration through the lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, transdermal, or pulmonary route. As a still further option, the polypeptide, the polypeptide complex, or the conjugate described herein can be formulated for administration through transdermal administration, for example, by needle-free injection or from a patch, optionally an iontophoretic patch, or transmucosal, for example, buccal, administration.

Methods of Treatment

In yet another aspect, the present disclosure further provides a method and a kit of preventing or treating a metabolic disorder in a subject in need thereof.

The method substantially comprises: administering a therapeutically effective amount of the polypeptide or the pharmaceutical composition as described above to the subject.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "subject" or "individual" or "animal" or "patient" as used herein refers to human or non-human animal, including a mammal or a primate, in need of diagnosis, prognosis, amelioration, prevention and/or treatment of a disease or disorder. Mammalian subjects include humans, domestic animals, farm animals, and zoo, sports, or pet animals such as dogs, cats, guinea pigs, rabbits, rats, mice, horses, swine, cows, bears, and so on.

In certain embodiments, the subject has been identified as having a disorder or condition likely to respond to the polypeptide or the pharmaceutical composition provided herein.

In certain embodiments, the metabolic disorder is diabetes, obesity, non-alcoholic steatohepatitis (NASH), cardiovascular like dyslipidemia, artheroscelerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, primary biliary cirrhosis (PBC), or severe hypertriglyceridemia (SHTG).

For example, a metabolic condition or disorder that can be treated or ameliorated using the polypeptide or the pharmaceutical composition provided herein, includes a condition where a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL.

The therapeutically effective amount of the polypeptide or the pharmaceutical composition provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements. The therapeutically effective amount can be an amount of the polypeptide conjugate or the pharmaceutical composition provided herein, that elicits a biological or medicinal response in a tissue system, animal, or human being sought by a researcher, medical doctor, or other clinician, which includes alleviation or amelioration of the symptoms of the disease or disorder being treated, i.e., an amount that supports an observable level of one or more desired biological or medicinal response, for example lowering blood glucose, insulin, triglyceride, or cholesterol levels; reducing body weight; or improving glucose tolerance, energy expenditure, or insulin sensitivity.

In certain embodiments, the polypeptide or the pharmaceutical composition provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the polypeptide or the pharmaceutical composition provided herein is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The polypeptide or the pharmaceutical composition provided herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

The polypeptide or the pharmaceutical composition may be administered alone or in combination with one or more additional therapeutic means or agents.

In certain embodiments, when used for treating a metabolic disease, the polypeptide or the pharmaceutical composition provided herein may be administered in combination with any other therapeutic agent for use in the treatment of a metabolic disease or any medical disorder that related. "Administered in combination" as used herein includes administration simultaneously as part of the same pharmaceutical composition, simultaneously as separate compositions, or at different timings as separate compositions. A composition administered prior to or after another agent is considered to be administered "in combination" with that agent as the phrase is used herein, even if the composition and the second agent are administered via different routes. Where possible, additional therapeutic agents administered in combination with the fusion polypeptide, the polypeptide complex or the conjugate provided herein are administered according to the schedule listed in the product information sheet of the additional therapeutic agent, or according to the Physicians' Desk Reference (Physicians' Desk Reference, 70th Ed (2016)) or protocols well known in the art.

Kits

A kit for practicing the methods for administering the pharmaceutical composition as described above is also provided. Such kits can comprise a pharmaceutical composition such as those described herein, which can be provided in a sterile container. Optionally, instructions on how to employ the provided pharmaceutical composition in the treatment of a metabolic disorder can also be included or be made available to a patient or a medical service provider.

Such a kit may comprise: (a) a pharmaceutical composition comprising a therapeutically effective amount of a fusion polypeptide conjugate; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, diabetes, obesity, non-alcoholic steatohepatitis (NASH), cardiovascular like dyslipidaemia, artherosclerosis, alcoholic steatohepatitis (ASH), diabeticnephropathy, metabolic syndrome such as metabolic syndrome X, nonalcoholic fatty liver disease (NAFLD), end-stage liver disease, hepatic steatosis (fatty liver), liver cirrhosis, primary biliary cirrhosis (PBC) or severe hypertriglyceridemia (SHTG).

Instructions can be printed on a substrate, such as paper or plastic, etc, and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded. Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

Polynucleotides Encoding the Polypeptide

In yet other aspects, the present disclosure further provides methods for preparing the polypeptide (or optionally the polypeptide conjugate) as described above. To this end, the following are provided in the present disclosure.

Firstly, the present disclosure provides isolated nucleic acids or polynucleotides that encode the fusion polypeptide as described herein.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The nucleic acids or polynucleotides encoding the fusion polypeptide described herein can be constructed using recombinant techniques. To this end, DNA encoding the serum albumin-binding nanobody, DNA encoding the FGF21 domain, and optionally DNA encoding the GLP-1 domain, can be obtained and operably linked to allow transcription and expression in a host cell to produce the polypeptide. Polynucleotide sequences encoding for the polypeptide linkers are also operably linked to allow expression of the desired product.

The encoding polynucleotide sequences can be further operably linked to one or more regulatory sequences, optionally in an expression vector, such that the expression or production of the fusion polypeptides is feasible and under proper control.

The encoding polynucleotide sequence(s) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. prokaryotic promoters such as T7, T7lac, Sp6, araBAD, trp, lac, tac, pLm, A3, lac, lpp, npr, pac, syn, trc and T3, or eukaryotic promoters such as SV40, CMV, and EF-1α), and a transcription termination sequence.

Vectors and Host Cells

Secondly and thirdly, the present disclosure further provides a vector comprising the polynucleotide of provided above, and a host cell that comprises the vector described herein.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Non-limiting examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the fusion polypeptide, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

Vectors comprising the polynucleotide sequence(s) provided herein can be introduced to a host cell for cloning or gene expression. The phrase "host cell" as used herein refers to a cell into which an exogenous polynucleotide and/or a vector has been introduced. In other embodiments, the vectors are extra-chromosomal. The host cells can be isolated if desired. In certain embodiments, the host cell is a prokaryotic cell, and in some other embodiments, the host cell is an eukaryotic cell.

Suitable host cells for cloning or expressing the DNA in the vectors herein are mainly prokaryotes. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. In some embodiments, host cells are eukaryotes, such as yeast and mammalian cells (e.g., immortalized mammalian cells).

A vector comprising the polynucleotide sequence(s) provided herein can be introduced into a host cell using any suitable method known to a skilled person in the art, e.g., transformation, transfection or transduction. In one example, the polynucleotide sequence encoding the fusion polypeptide can be subcloned into an expression vector, which is expressed as inclusion bodies in the host cells. The vector can be a viral vector, and any suitable viral vector can be used in this capacity.

Herein, the host cell can be a prokaryotic cell or an eukaryotic cell. Host cells transformed with the above-described expression or cloning vectors can be cultured in conventional nutrient media modified as appropriate for inducing promoters, selecting transformants, or amplifying the cloning vectors.

In another aspect, the present disclosure provides a method of producing the fusion polypeptide as described herein, comprising culturing the host cell provided herein under a condition that allows expression of the fusion polypeptide as described herein.

For production of the fusion polypeptide as described herein, the host cells transformed with the expression vector may be cultured in a variety of media. Commercially available bacteria growth media such as Terrific Broth, LB Broth, LB Agar, M9 minimal media, MagiaMedia Medium, and ImMedia Medium (ThermoFisher) are suitable for culturing the bacterial host cells. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the eukaryotic host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Methods for Producing the Polypeptide

In one aspect, the present disclosure provides a method of expressing the fusion polypeptide as described herein, comprising culturing the host cell provided herein under the condition at which the fusion polypeptide as described herein is expressed.

In certain embodiments, the fusion polypeptide is expressed as inclusion bodies. In certain embodiments, the method further comprises renaturing the fusion polypeptide from the inclusion bodies.

When using recombinant techniques, the fusion polypeptide as described herein can be produced intracellularly, in the periplasmic space, or directly secreted into the medium. If the product is produced intracellularly, as a first step, the particulate debris, either host cells or lysed fragments, is removed, for example, by centrifugation or ultrafiltration. Carter et al., Bio/Technology 10:163-167 (1992) describe a procedure for isolating proteins which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the product is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In certain embodiments, the method further comprises isolating the fusion polypeptide.

The fusion polypeptide as described herein prepared from the cells can be purified using, for example, hydroxylapatite chromatography, gel electrophoresis, dialysis, DEAE-cellulose ion exchange chromatography, ammonium sulfate precipitation, salting out, and affinity chromatography.

Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

A method or process for producing the polypeptide as described above is also provided in the present disclosure, which substantially comprises the following two steps:

S100: culturing the host cell as described above under a condition that allows expression of the polynucleotide as defined above or a precursor thereof further comprising a removable tag; and S200: collecting and purifying the polypeptide or the precursor thereof from the host cell.

In certain embodiments, the polypeptide is expressed as inclusion bodies. In certain embodiments, the method further comprises renaturing the polypeptide from the inclusion bodies to allow a refolding thereof. Further according to some embodiments, the host cell is *E. coli*, the vector comprises an *E. coli*-compatible vector, and the polypeptide encoded by the polynucleotide in the vector is codon optimized for *E. coli* expression.

When using recombinant techniques, the polypeptide as described herein can be produced intracellularly, in the periplasmic space, or directly secreted into the medium. If the product is produced intracellularly, as a first step, the particulate debris, either host cells or lysed fragments, is removed, for example, by centrifugation or ultrafiltration.

According to some embodiments, step S200 of collecting and purifying the polypeptide from the host cell may comprise the following sub-steps:

S210: collecting the precursor of the polypeptide;

S220: allowing the precursor of the polypeptide to refold;

S230: treating the refolded precursor of the polypeptide to remove the tag and thereby obtain the polypeptide; and S240: purifying the polypeptide.

In certain embodiments, the host cell is lysed and the polypeptide or the precursor of the polypeptide is obtained from the insoluble fraction containing the polypeptide or the precursor of the polypeptide.

According to some embodiments of the polypeptide producing process, the process further comprises conjugating the purified polypeptide with the functional moiety. In certain embodiments, the functional moiety to be conjugated to the polypeptide is

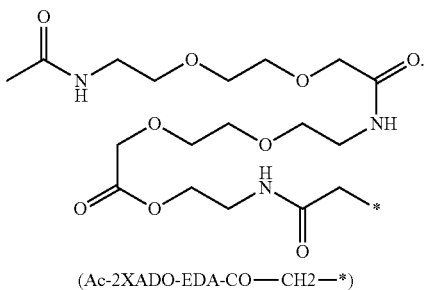

(Ac-2XADO-EDA-CO—CH2—*)

EXAMPLES

Example 1: Recombinant Expression of Nanobody-FGF21 Proteins and GLP-1-Nanobody-FGF21

The GLP-1-nanobody-FGF21 proteins or nanobody-FGF21 fusion proteins listed in Tables 1A and 1B, and Table 1C were produced from bacterial *E. coli* expression system, using BL21 (DE3) derivative strain. The DNA coding for the GLP-1-nanobody-FGF21 fusion precursor or nanobody-FGF21 fusion proteins was codon optimized for *E. coli* expression, de novo synthesized and subcloned into PET derivative expression vectors (Novagen). Amino acid substitutions were accomplished by modification of the corresponding genetic codes. Overexpression of GLP-1-nanobody-FGF21 fusion precursor or nanobody-FGF21 fusion proteins was induced with 0.5 mM isopropyl b-d-thiogalactoside (IPTG) when the cell density reached an OD600 of 2.0 in Terrific Broth (TB) medium. The cells were harvested after protein induction at 37° C. for 20-22 hours.

TABLE 1C

| Control molecules of GLP-1/FGF21 proteins | | |
|---|---|---|
| Molecule Code. (MLC); Fusion Polypeptide (SEQ ID NO) | Note | Conjugation on FGF21 domain |
| Control#1 (SEQ ID NO: 71) | GLP1(del7-8, 22E, 36G)-(G4S)4-ALB8-G4SG3S-FGF21 (121Q, 168L, 171G, 180E) Control to MLC#8, GLP1 dead | no |
| Control#2 (SEQ ID NO: 72) | GLP1(del7-8, 22E, 36G)-(GAQP)5-ALB8-(GAQP)10-FGF21 (121Q, 168L, 171G, 180E) GLP1 dead | no |
| Control#3 (SEQ ID NO: 73) | GLP1(del7-8, 22E, 36G)-(GAQP)5-ALB8-(GQEPGAQP)6-FGF21 (121Q, 168L, 171G, 180E) GLP1 dead | no |
| Control#4 (SEQ ID NO: 76) | GLP1(del7-8, 22E, 36G)-(GAQP)5-ALB8-(GAQP)5-FGF21 (121Q, 168L, 171G, 180E) GLP1 dead | no |
| Control#5 (SEQ ID NO: 77) | GLP1(del7-8, 22E, 36G)-(GAQP)5-ALB8-(GAQP)2-FGF21 (121Q, 168L, 171G, 180E) GLP1 dead | no |
| Control#6 (SEQ ID NO: 78) | GLP1(del7-8, 22E, 36G)-(GAQP)5-ALB8-(GAQP)-FGF21 (121Q, 168L, 171G, 180E) GLP1 dead | no |
| Control#7 (SEQ ID NO: 84) | GLP1(del7-8, 22E, 36G)-(GAQP)5-ALB8-FGF21 (121Q, 168L, 171G, 180E) GLP1 dead | no |
| Control#8 (SEQ ID NO: 86) | GLP1(del 7-8, 22E, 36G)-(GAQP)14-ALB8-(GAQP)-FGF21 (121Q, 168L, 171C, 180E) Ac-2XADO-EDA-CO—CH2 at 171C (0025 GLP1 dead) | Conjugated |
| Control#9 (SEQ ID NO: 87) | GLP1(8G, 22E, 36G)-(GAQP)14-ALB8-(GAQP)-FGF21 (L137P, 121Q, | Conjugated |

TABLE 1C-continued

Control molecules of GLP-1/FGF21 proteins

| Molecule Code. (MLC); Fusion Polypeptide (SEQ ID NO) | Note | Conjugation on FGF21 domain |
|---|---|---|
| Control#10 (SEQ ID NO: 88) | 168L, 171C, 180E) Ac-2XADO-EDA-CO—CH2 at 171C (0025 FGF21 dead) GLP1(del7-8, 22E, 36G)-(GAQP)14-ALB8-(GAQP)-FGF21 (L137P, 121Q, 168L, 171C, 180E) Ac-2XADO-EDA-CO—CH2 at 171C (0025 GLP1 dead, FGF21 dead) | Conjugated |

Example 2: Purification of Nanobody-FGF21 Proteins

Cells were harvested and lysed in 20 mM Tris pH8.0, 0.15M NaCl buffer by cell disruptor (900 bar, for twice). The insoluble fractions, containing nanobody-FGF21 fusion proteins were collected and by centrifugation (8,000×g, for 30 min). After refolding, the fusion proteins were purified by anion exchange chromatography. The samples in each step were characterized by LC/MS to confirm the correct molecular weight.

Example 3: Purification of GLP-1-Nanobody-FGF21

Cells were harvested and lysed in 20 mM Tris pH8.0, 0.15M NaCl buffer by cell disruptor (900 bar, for twice). The insoluble fractions, containing the GLP-1-nanobody-FGF21 fusion precursor were collected and by centrifugation (8,000×g, for 30 min). After refolding, the fusion protein precursors were captured by anion exchange chromatography. After removing tag by protease, the proteins were purified by hydrophobic interaction chromatography. The samples in each step were characterized by LC/MS to confirm the correct molecular weight.

Example 4: Preparation of Nanobody-FGF21 and GLP-1-Nanobody-FGF21 Fusion Protein Conjugate To a solution of a nanobody-FGF21 or GLP-1-nanobody-FGF21 fusion protein in Tris buffer was added with Ac-2XADO-EDA-CO—CH2-Br in organic solvent dropwise. The reaction was stirred at room temperature for 1 h. Then the product was applied to aion exchange chromatography. This provided the compounds as listed in Table 1 as shown above.

The conjugated fusion proteins were detected and characterized by LC-MS method with Waters BioAccord LC-MS system, or by UPLC with Waters Acquity UPLC system, using conditions optimized for different conjugates, following the supplier's manuals.

Example 5: In Vitro Activities

Method: The in vitro GLP-1 activities of the fusion protein were measured using a BHK cell line overexpressing human GLP-1 receptor and CRE luciferase reporter with or without 1% human serum albumin (HSA). Tested fusion proteins were measured at 100 nM as top concentration in the presence of 1% HSA with 3-fold serial dilutions. After cells were treated with molecules for 4 hours, luciferase activities were measured by Steadylite plus kit (Perkin Elmer, 6066751).

The activity of each fusion protein was represented by EC50, derived from non-linear regression analysis.

The in vitro FGF21 activities of the fusion protein were assessed using a HEK293 cell line overexpressing human beta-Klotho. Tested fusion protein conjugates were measured at 400 nM top concentration with 4-fold serial dilutions in the presence of 1% HSA. After cells were treated with fusion protein conjugates for 12 mins, p-ERK levels were measured by p-ERK kit (Cisbio, 64ERKPEH).

The activity of each fusion protein was represented by EC50, derived from non-linear regression analysis.

Figure 2A:
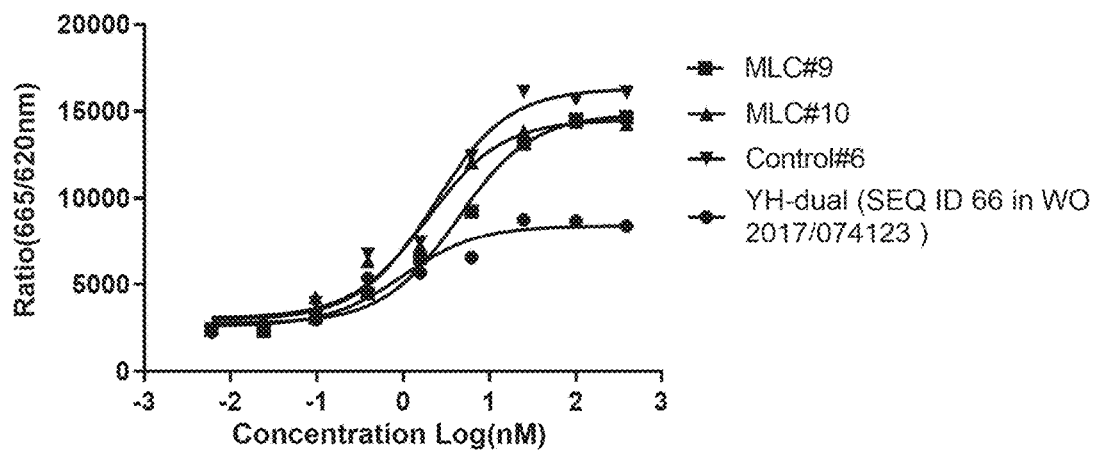
FIGS. 2A and 2B show in vitro FGF21 activity of the Molecules MLC #9, MLC #10, MLC #14, Control #6 and a reference compound YH-dual.
Figure 2B:
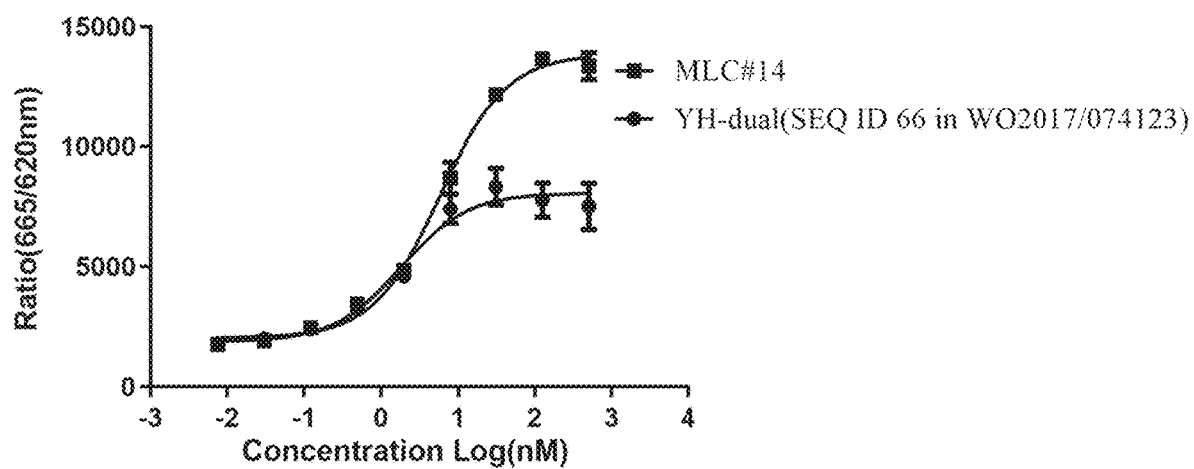

Conclusion: As shown in table 2 and 3, all fusion proteins showed comparable potency with native FGF21. However, the fusion molecules (MLC #9, MLC #10, MLC #12, MLC #13, MLC #14, MLC #15, MLC #16, MLC #17, MLC #19 and MLC #21) exhibited different GLP-1 activities. The molecule MLC #14, MLC #16, MLC #17, MLC #19 and MLC #21 showed significantly higher GLP1 activity than MLC #9, MLC #12, MLC #13 and MLC #15. Compared with other fusion molecules tested, MLC #15 has relatively shorter second linker and the GLP-1 activity is also lower. Taken together, this may indicate that the fusion molecule with longer second linker can have higher GLP1 activity. As shown in FIGS. 2A and 2B, the fusion molecules (MLC #9, MLC #10, control #6 and MLC #14) showed significantly higher FGF21 efficacy than YH-dual molecule (i.e. the molecule disclosed as SEQ ID NO. 66 in WO 2017/074123).

TABLE 2

In vitro GLP1 activities and FGF21 activity of GLP-1-Nanobody-FGF21 fusion proteins conjugates.

| Molecule Code. | Second linker | First linker | Conjugation on FGF21 domain | GLP-1 activity (EC$_{50}$, pM) | FGF21 activity (EC$_{50}$, nM) |
|---|---|---|---|---|---|
| Semaglutide | no | no | no | 282 | NA |
| Native FGF21 | no | no | no | NA | 0.96 |
| Control#1 | (G4S)4 | G4SG3S | no | >50000 | 1.04 |
| Control#2 | (GAQP)5 | (GAQP)10 | no | >50000 | 2.10 |
| Control#13 | (GAQP)5 | (GQEPGAQP)6 | no | >50000 | 3.47 |
| Control#4 | (GAQP)5 | (GAQP)5 | no | >50000 | 1.47 |
| Control#5 | (GAQP)5 | (GAQP)2 | no | >50000 | 1.35 |
| Control#6 | (GAQP)5 | (GAQP) | no | >50000 | 2.26 |
| MLC#10 | (GAQP)5 | (GAQP)10 | no | 654 | 1.83 |
| MLC#9 | (GAQP)5 | (GAQP)10 | 171C | 2184 | 4.26 |
| MLC#12 | (GAQP)5 | (GAQP) | no | 2220 | 1.78 |

TABLE 2-continued

In vitro GLP1 activities and FGF21 activity of GLP-1-Nanobody-FGF21 fusion proteins conjugates.

| Molecule Code. | Second linker | First linker | Conjugation on FGF21 domain | GLP-1 activity ($EC_{50}$, pM) | FGF21 activity ($EC_{50}$, nM) |
|---|---|---|---|---|---|
| MLC#13 | (GAQP)5 | (GAQP) | 171C | 3854 | 5.06 |
| MLC#14 | (GAQP)10 | (GAQP) | 171C | 416 | 4.01 |
| MLC#15 | (GAQP)2 | (GAQP) | 171C | 9711 | 1.01 |
| MLC#16 | (GAQP)14 | (GAQP) | 171C | 118 | 2.31 |
| MLC#17 | (GAQP)14 | (GAQP) | 174C | 207 | 3.75 |
| MLC#21 | (GAQP)14 | G4S | no | 128 | 5.28 |
| MLC#19 | (GAQP)14 | G4S | 171C | 192 | 4.98 |

NA: not available.

TABLE 3

In vitro FGF21 activity of Nanobody-FGF21 fusion proteins conjugates.

| Molecule Code. | First linker | Conjugation on FGF21 domain | FGF21 activity ($EC_{50}$, nM) |
|---|---|---|---|
| MLC#5 | (GAQP) | no | 7.65 |
| MLC#6 | (GAQP) | 171C | 6.65 |
| MLC#25 | G4S | no | 7.45 |
| MLC#23 | G4S | 171C | 5.83 |

Example 6: Efficacy Study in Disease Models

Selected molecules are assessed in disease animal models (such db/db mice, Diet-Induced-Obesity (DIO) mice) to determine body weight, food intake, glucose efficacy with dose responses in chronic studies. Some biomarkers are also measured, including plasma insulin, plasma triglyceride, plasma cholesterol, plasma LDL-c, plasma adiponectin, liver triglyceride, liver cholesterol and liver function indexes (ALT, AST).

A) Food Intake and Body Weight Reduction
Method:

22 week old DIO male C57BL/6 mice (~50 g) were injected once every other day (Q2D) subcutaneously with designated GLP-1 polypeptide conjugates (i.e., Molecule 012) for 25 days. Food intake and body weight were measured twice a week and fasting blood glucose was measured once a week. Five animals were used for each treatment group. Body weight and fasting blood glucose was monitored for each individual animal, but food intake for each group animals was measured together. Day 1 and Day 25 are first day and last day of molecule dosage. Data are indicated as mean values and standard error (SEM) or pooled values. Statistical analysis was performed by One-way ANOVA. Body weight reduction on Day 25 is calculated by −1*(% BW loss−% BW loss of vehicle group); Cumulative food intake reduction is calculated by −100* (cumulative food intake−cumulative food intake of vehicle)/ cumulative food intake of vehicle.

Figure 3A:
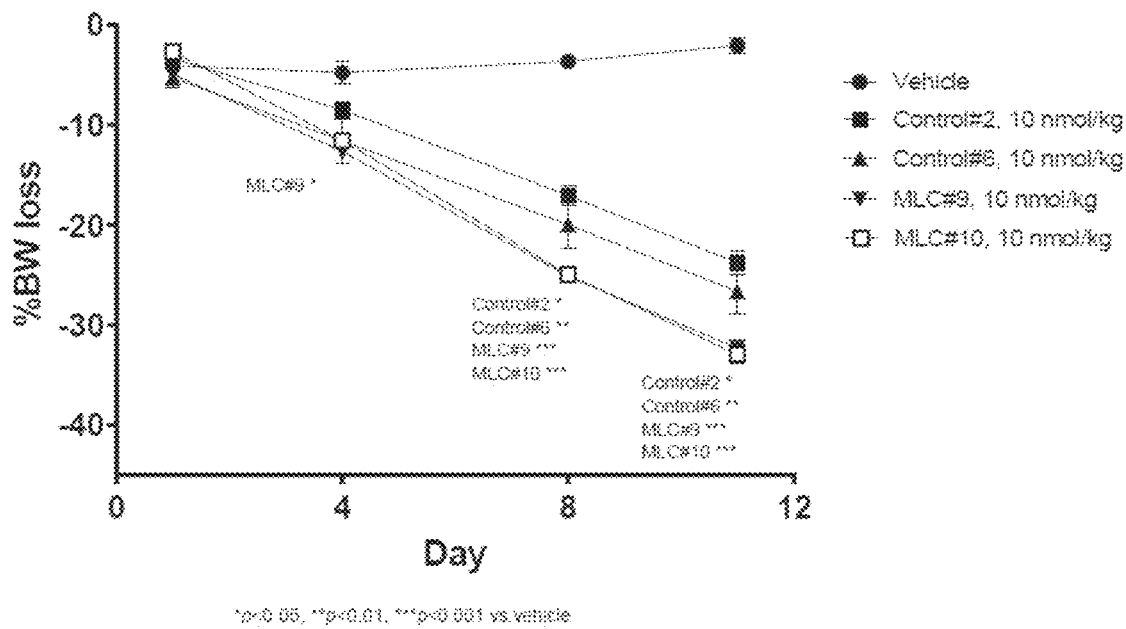
FIGS. 3A and 3B show efficacy of Molecules Control #2, Control #6, MLC #9 and MLC #10 on body weight reduction (FIG. 3A) and food intake suppression (FIG. 3B) in DIO rats.
Figure 3B:
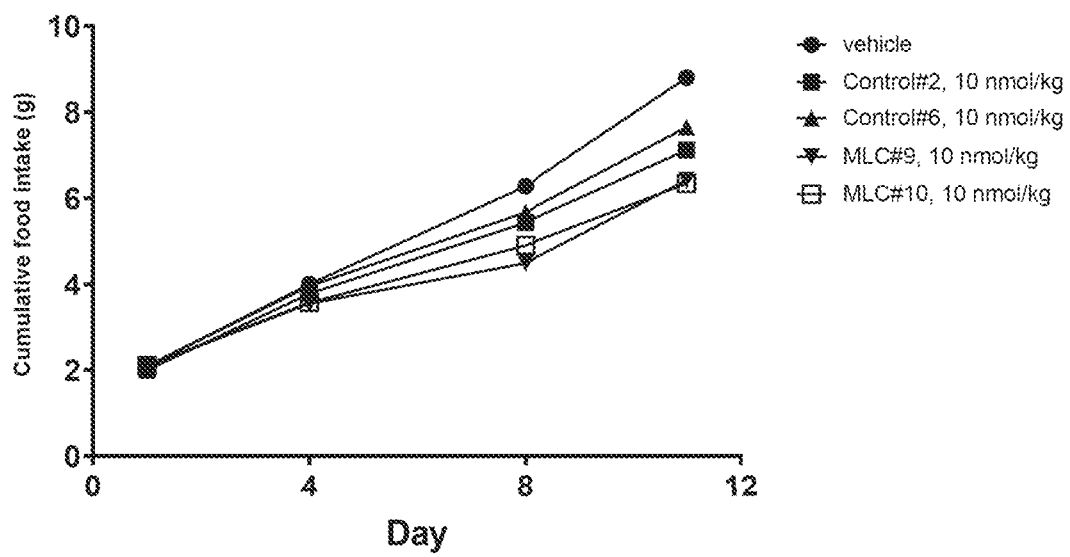

Conclusion: in DIO study, as shown in FIG. 3A, 3B and Table 8, Molecule Control #2, Control #6, MLC #9 and MLC #10 have significant effect on body weight reduction and food intake suppression.

TABLE 8

Food intake and body weight reduction in DIO mice at Day 11

| Group | Cumulative food intake reduction (% reduction compared to vehicle) (Day 11) | Body weight reduction (% reduction compared to vehicle) (Day 11) |
|---|---|---|
| Control#2 10 nmol/kg QD | 19.1 | 21.7 |
| Control#6 10 nmol/kg QD | 13.1 | 24.6 |
| MLC#9 10 nmol/kg QD | 27.1 | 30.3 |
| MLC#10 10 nmol/kg QD | 28.0 | 30.9 |

B) Metabolic Parameters in DIO Animal Model
Method:

16 week old DIO male C57BL/6 mice (35~40 g) were injected once daily (QD) subcutaneously with designated GLP-1/FGF21 conjugates (i.e., MLC #9, MLC #14, MLC #16 and MLC #17) for 21 days. Food intake and body weight were measured once everyday and non-fasting blood glucose was measured once every three days. Five animals were used for each treatment group. Body weight and blood glucose was monitored for each individual animal, but food intake for each group of animals was measured together. Day 1 and Day 21 are first day and last day respectively of the treatment. Terminal blood was collected and EDTA-K3 plasma was prepared and frozen at −80° C. for biomarker measurement (LDL-C, TC, TG, ALT, insulin, adiponectin). Liver and adipose tissue were also collected and frozen in liquid nitrogen and store at −80° C. Data are indicated as mean values and standard error (SEM) or pooled values. Statistical analysis was performed by One-way ANOVA. Body weight reduction on Day 21 is calculated by −1*(% BW loss−% BW loss of vehicle group); Cumulative food intake reduction is calculated by −100*(cumulative food intake−cumulative food intake of vehicle)/cumulative food intake of vehicle.

Figure 4A:
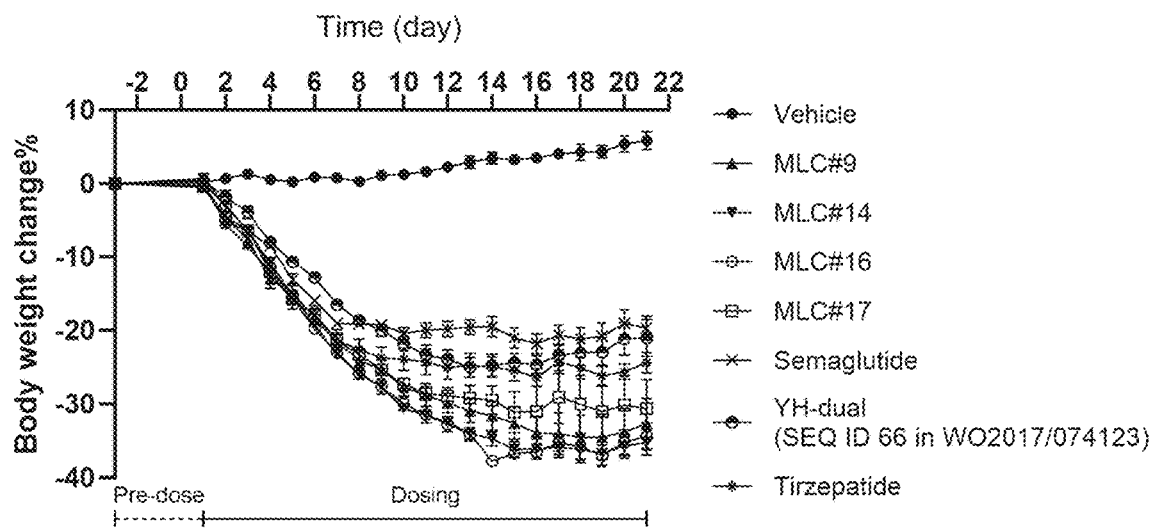
FIGS. 4A to 4L show efficacy of Molecules MLC #9, MLC #14, MLC #16 and MLC #17, and reference compounds semaglutide, YH-dual, and Tirzepatide on body weight reduction (FIG. 4A), glucose control (FIG. 4B), reduction of triglyceride (FIG. 4C), LDL-C (FIG. 4D), total cholesterol (FIG. 4E) and ALT (FIG. 4F) concentration in plasma and reduction of adipose weight (FIG. 4G) and liver weight (FIG. 4H), along with the improvement of liver TG (FIG. 4I), liver TC (FIG. 4J) and insulin sensitivity (FIG. 4K), and increase in adiponectin level (FIG. 4L) in DIO mice.

Conclusion:

In DIO mice study, as shown in FIG. 4A, Molecule MLC #9, MLC #14, MLC #16 and MLC #17 showed much better efficacy on body weight reduction compared to Semaglutide, Tirzepatide and YH-dual (SEQ ID 66 in WO2017/074123). MLC #9, MLC #14, MLC #16 and MLC #17 induced body weight loss by about 30-35% in the study. In contrast, Semaglutide, Tirzepatide and YH-dual induced body weight loss by about 20% to 25%.

Figure 4B:
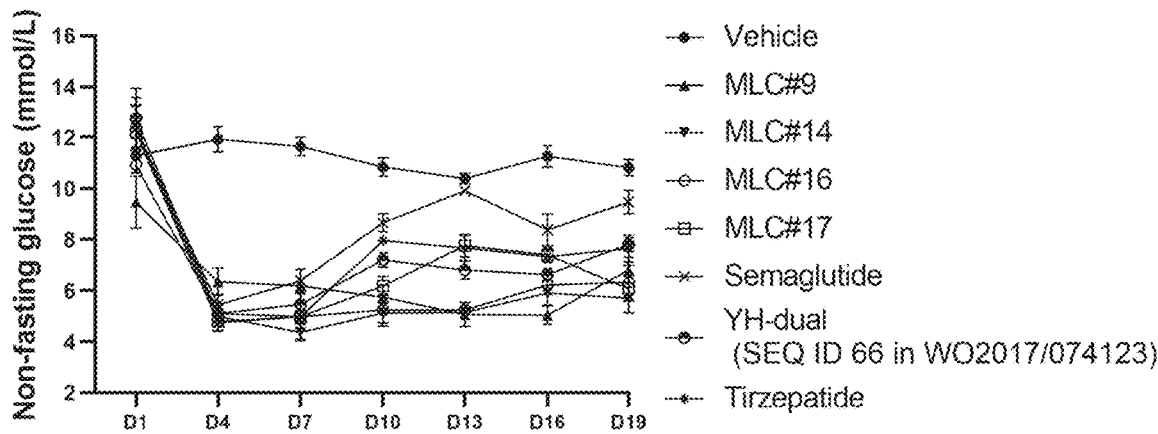

In FIG. 4B, the MLC #9, MLC #14, MLC #16 and MLC #17 groups showed better glucose control than Semaglutide, Tirzepatide and YH-dual. MLC #9, MLC #14, MLC #16 and MLC #17 decreased non-fasting glucose level to lower than 7 mmol/L. In contrast, Semaglutide decreased non-fasting glucose to about 7.5-10 mmol/L.

Figure 4C:
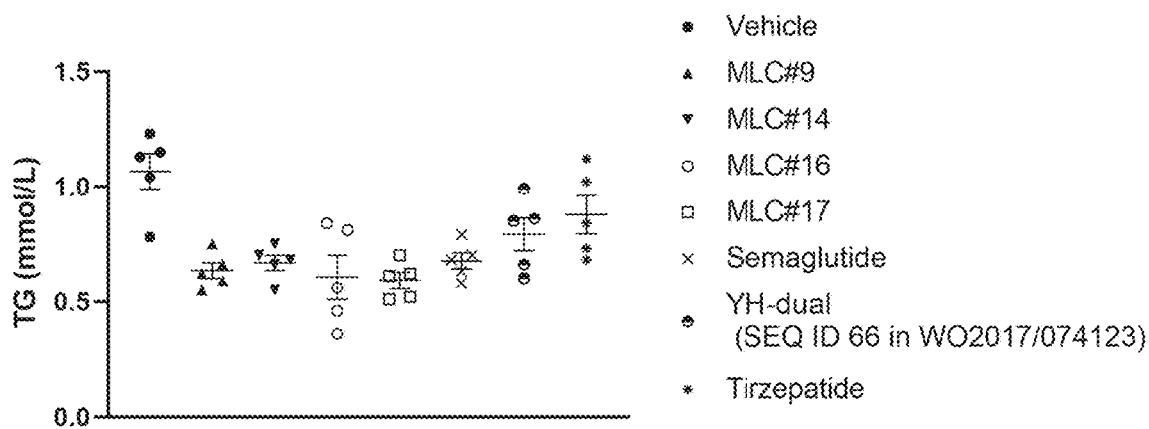
Figure 4D:
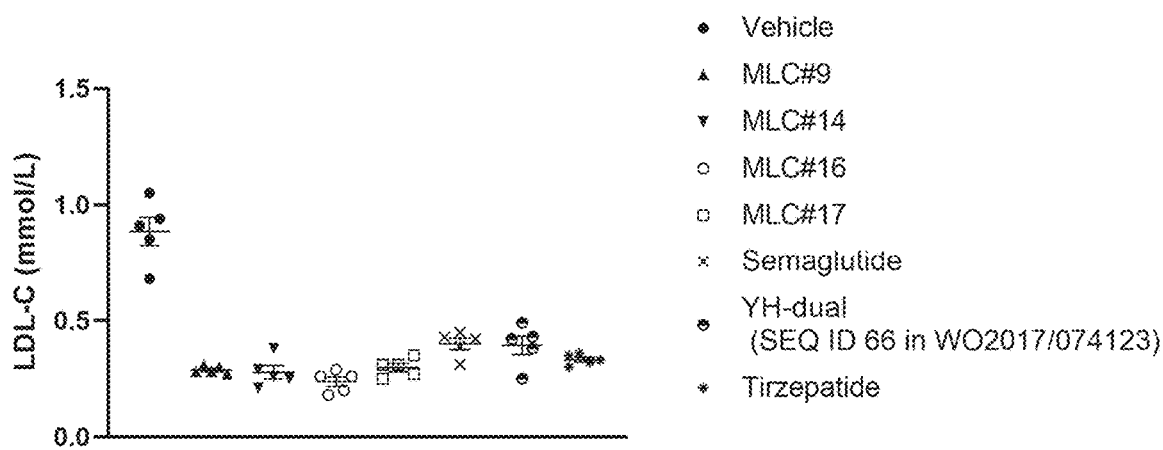
Figure 4E:
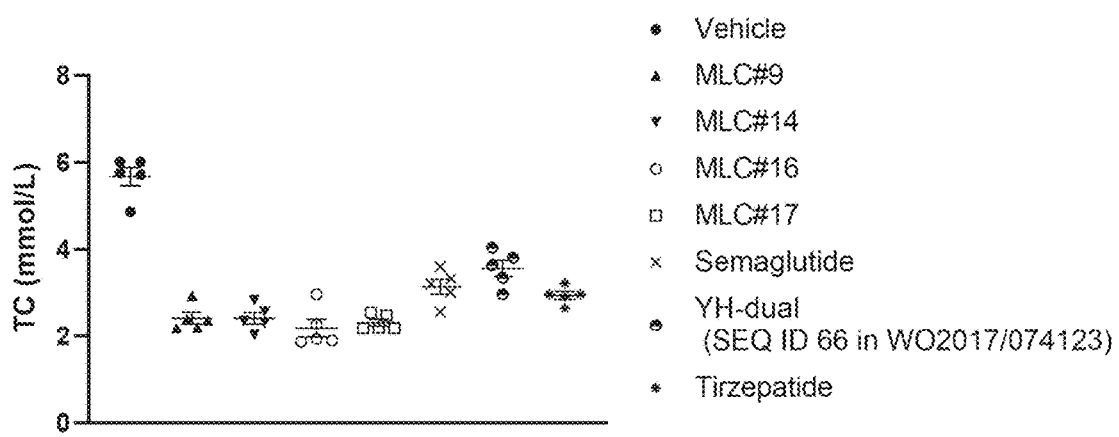
Figure 4F:
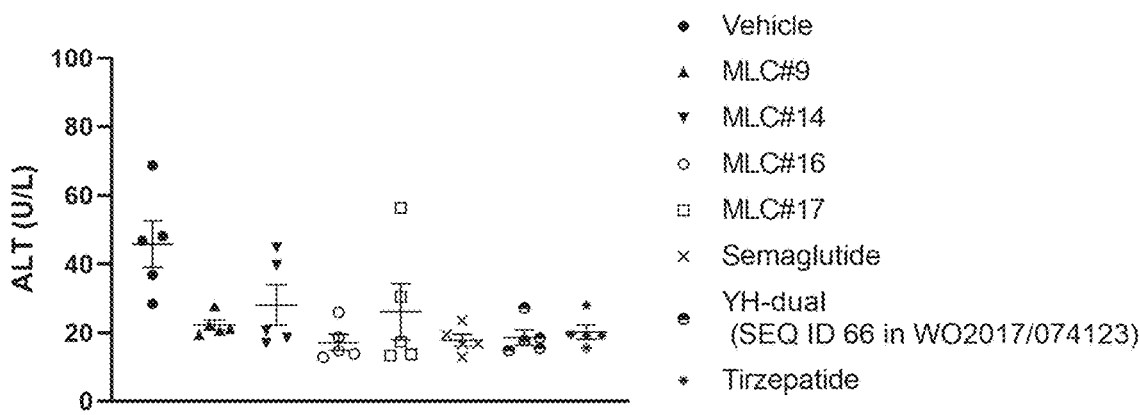
Figure 4G:
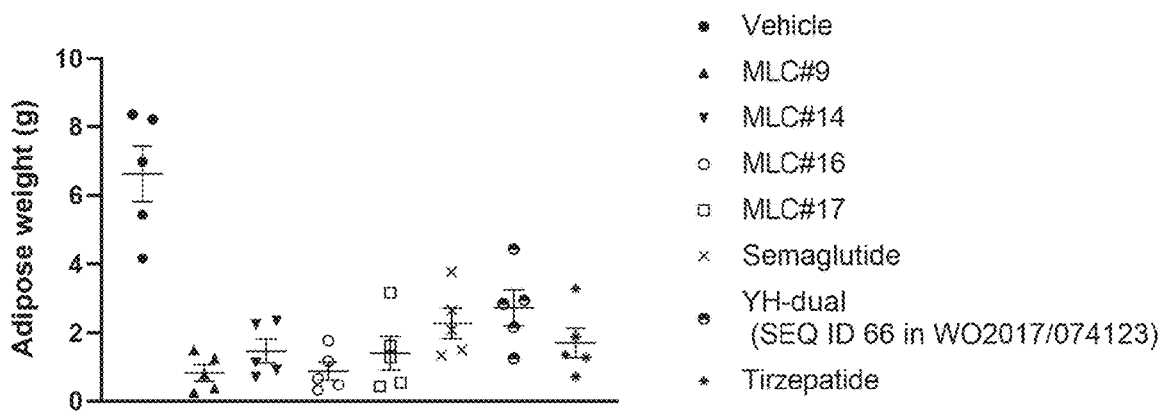
Figure 4H:
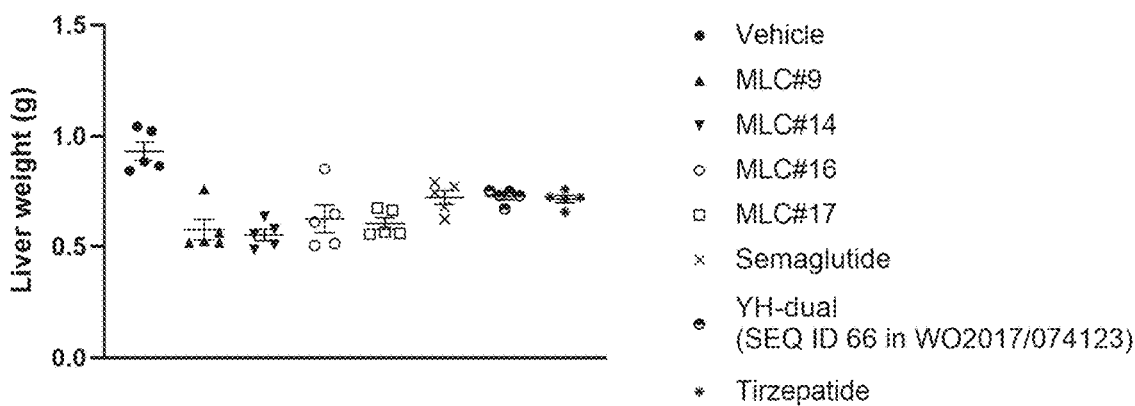
Figure 4I:
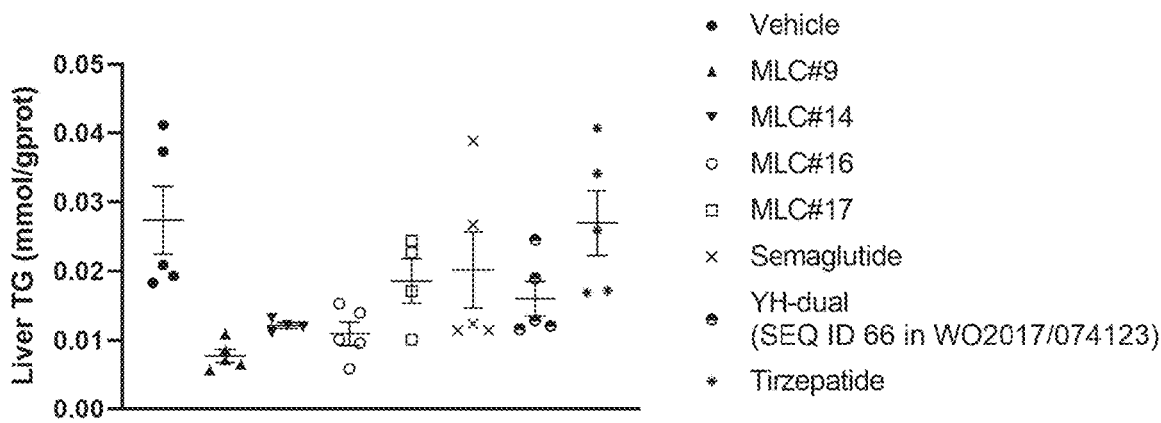
Figure 4J:
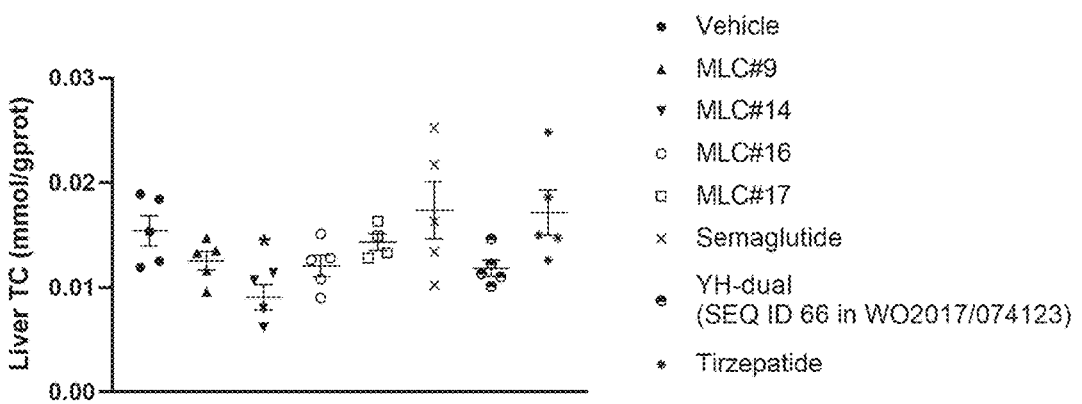
Figure 4K:
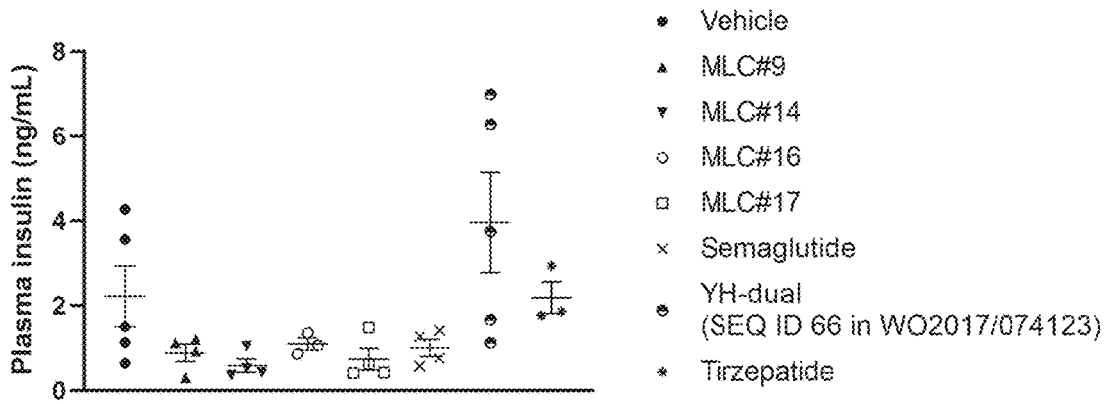

MLC #9, MLC #14, MLC #16 and MLC #17 also induced the reduction of triglyceride (FIG. 4C), LDL-C (FIG. 4D), total cholesterol (FIG. 4E) and ALT (FIG. 4F) concentration in plasma and reduction of adipose weight (FIG. 4G) and liver weight (FIG. 4H), along with the improvement of liver TG (FIG. 4I), liver TC (FIG. 4J) and insulin sensitivity (FIG. 4K).

Figure 4L:
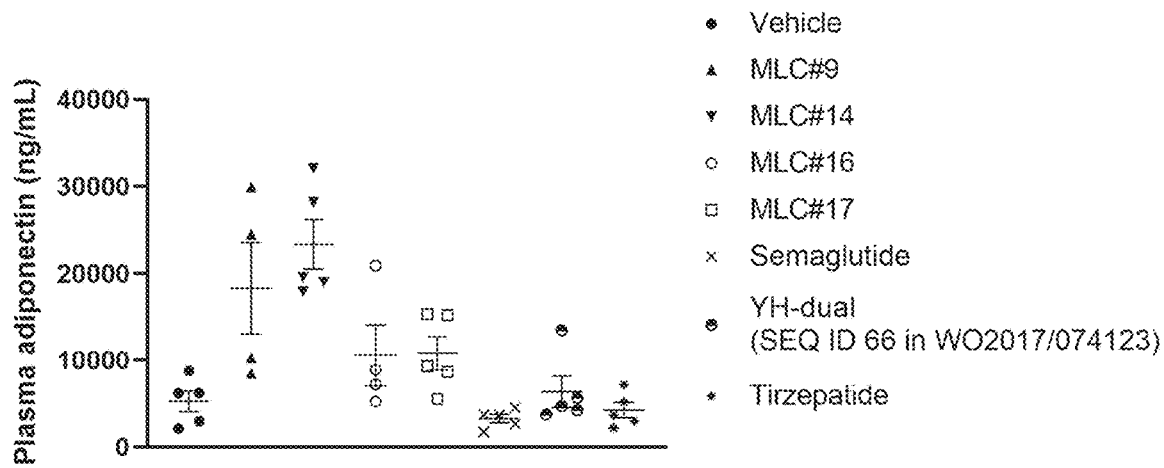

In vivo, FGF21 can induce secretion of adiponectin which is reported to be an insulin sensitizer. The fusion molecules MLC #9, MLC #14, MLC #16 and MLC #17 showed better effect on increase of adiponectin level than YH-dual indicating the better FGF21 activity (FIG. 4L).

C) Metabolic Parameters in ob/ob Animal Model at Different Dosages

Method: 10 week old ob/ob male mice (42~55 g) were injected once daily (QD) subcutaneously with designated GLP-1/FGF21 conjugates (i.e., MLC #14 and MLC #16) for 14 days. Food intake and body weight were measured once everyday. Non-fasting blood glucose was measured once every three days. Plasma triglyceride (TG) levels was measured once every week. Five or six animals were used for each treatment group. Body weight and blood glucose was monitored for each individual animal, but food intake for each group animals was measured together. Day 1 and Day 14 are first day and last day of molecule dosage. On the Day 14 after treatment, mice were sacrificed via cardiac puncture under anesthesia. Terminal blood was collected and frozen at −80° C. for biomarker measurement (LDL-C, TC, TG, ALT/AST, insulin, adiponectin). Liver and adipose tissue were also collected and frozen in liquid nitrogen and store at −80° C. Data are indicated as mean values and standard error (SEM) or pooled values. Statistical analysis was performed by One-way ANOVA. Body weight reduction on Day 14 is calculated by −1*(% BW loss−% BW loss of vehicle group); Cumulative food intake reduction is calculated by −100* (cumulative food intake−cumulative food intake of vehicle)/ cumulative food intake of vehicle.

Figure 5A:
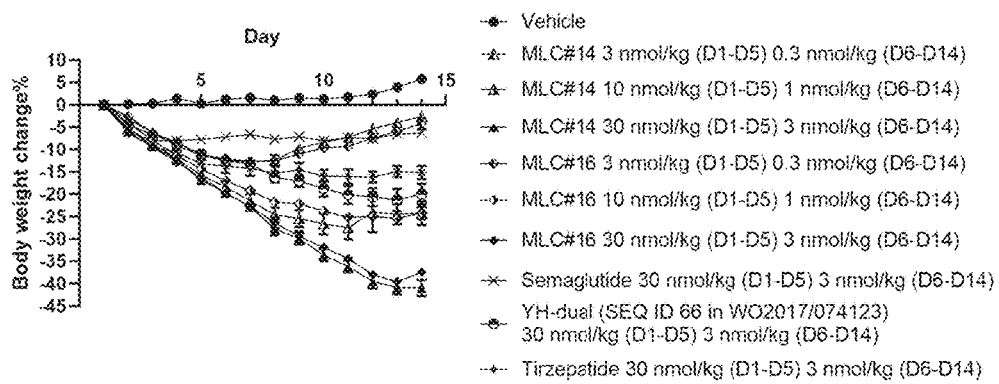
FIGS. 5A to 5M show efficacy of Molecules MLC #14 and MLC #16 at different dosages, in comparison to reference compounds semaglutide, YH-dual, and Tirzepatide on body weight reduction (FIG. 5A), glucose control (FIG. 5B), reduction of triglyceride (FIG. 5C), LDL-C (FIG. 5D), total cholesterol (FIG. 5E), ALT (FIG. 5F) and AST (FIG. 5G) concentration in plasma and reduction of adipose weight (FIG. 5H) and liver weight (FIG. 5I) along with the improvement of liver TG (FIG. 5J), liver TC (FIG. 5K) and insulin sensitivity (FIG. 5L), and increase in adiponectin level (FIG. 5M) in DIO mice.
Figure 5B:
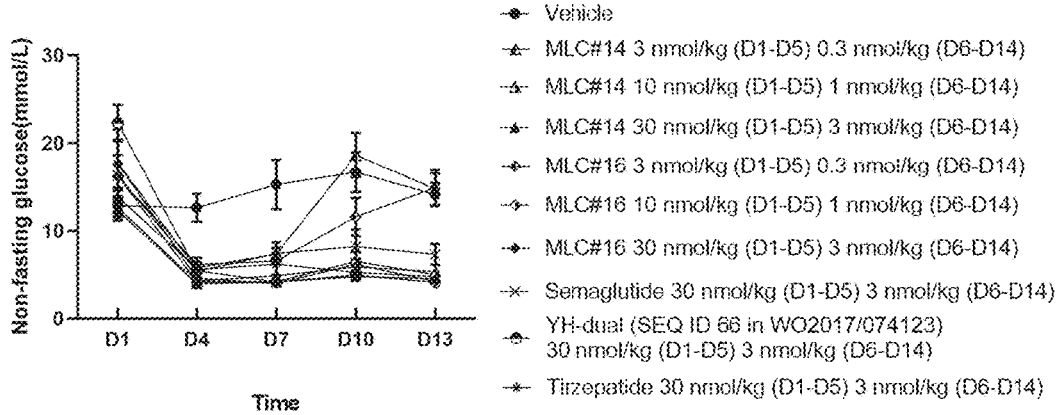
Figure 5C:
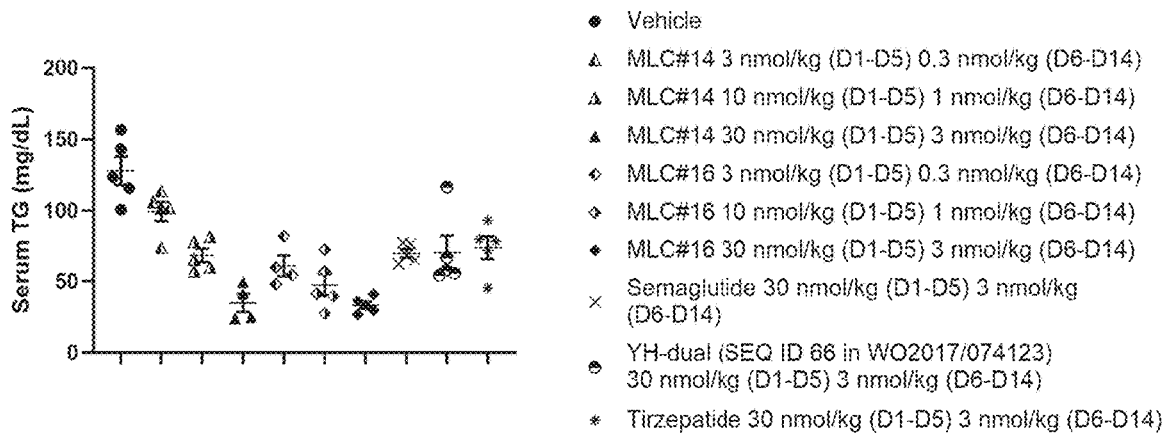
Figure 5D:
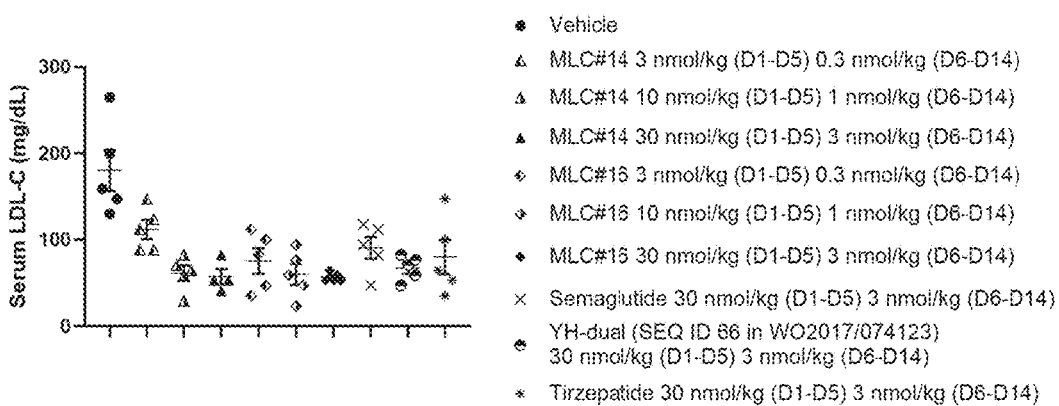
Figure 5E:
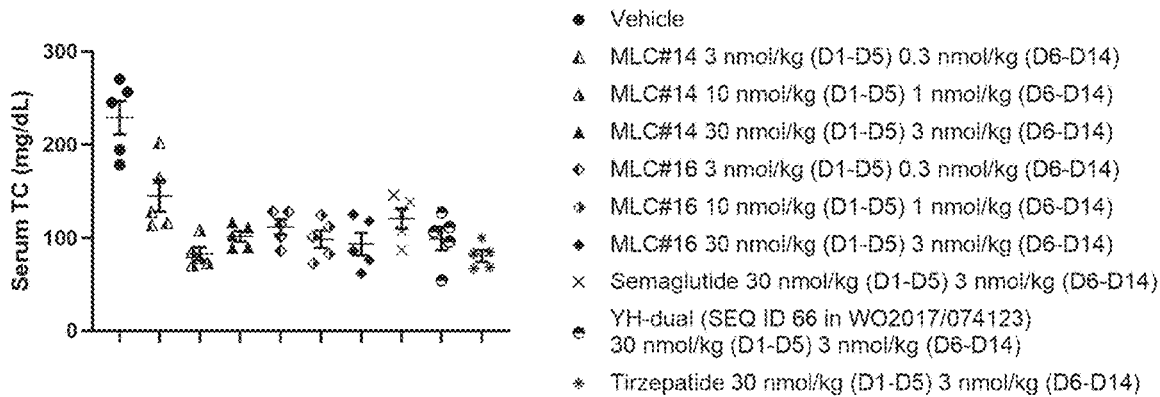
Figure 5F:
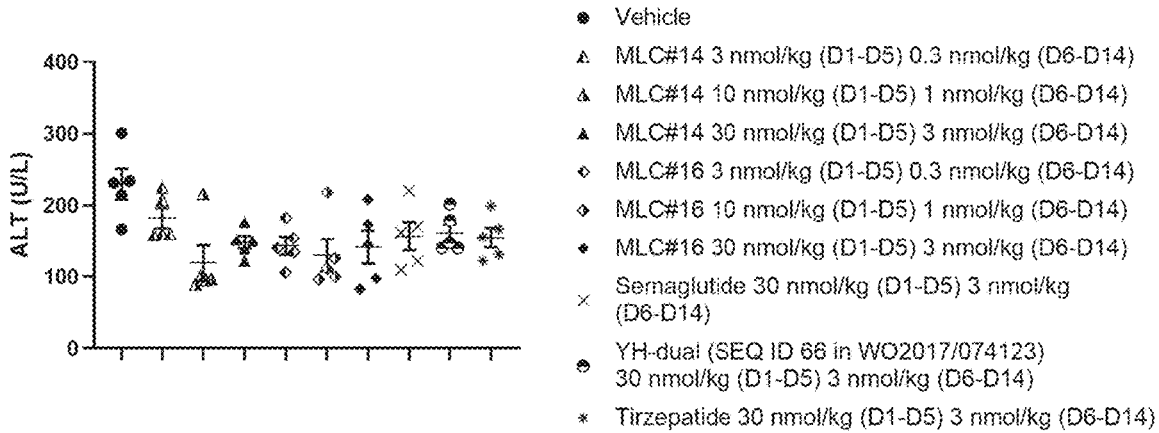
Figure 5G:
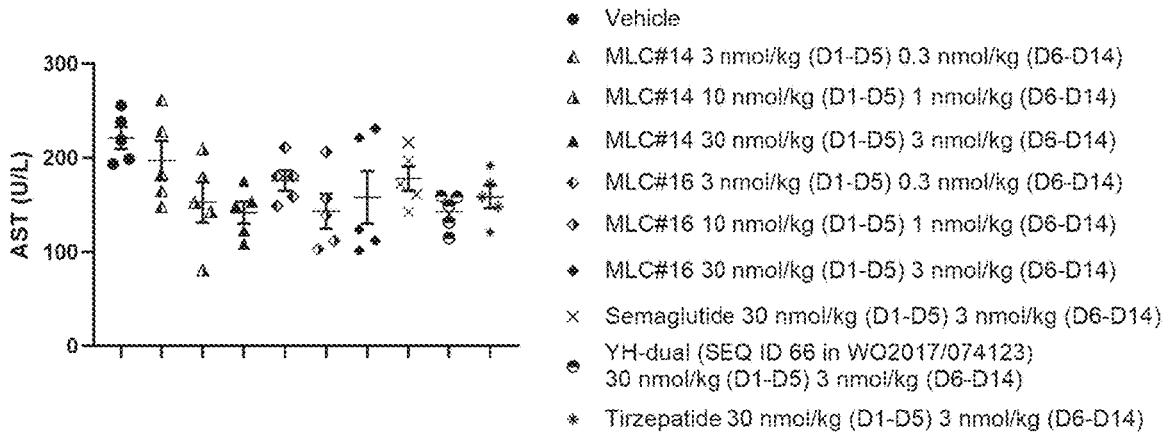
Figure 5H:
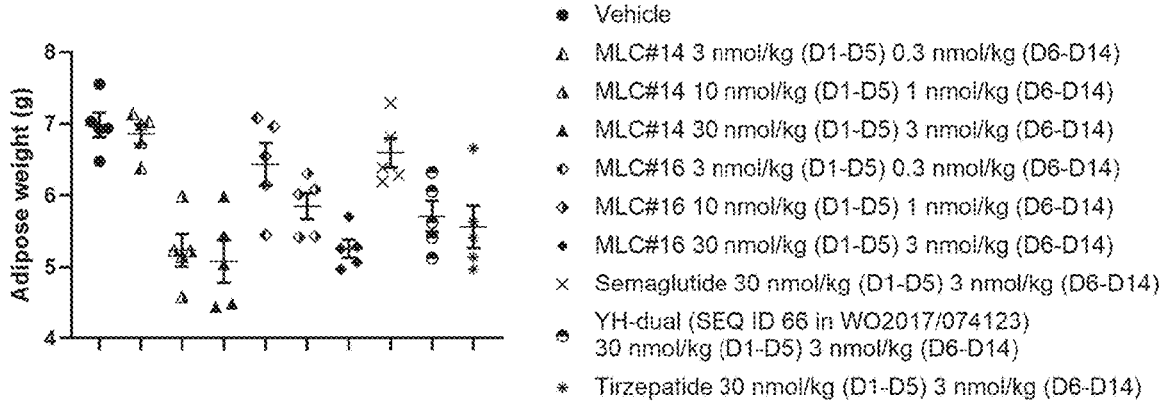
Figure 5I:
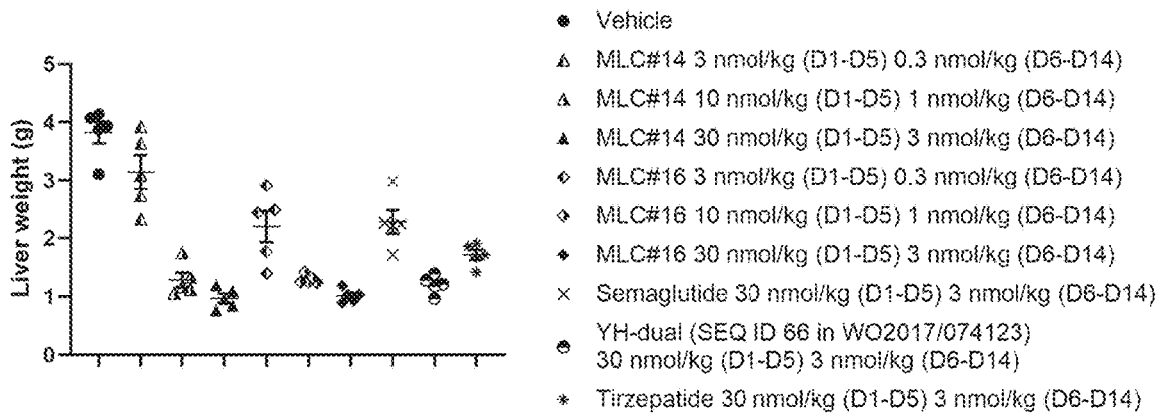
Figure 5J:
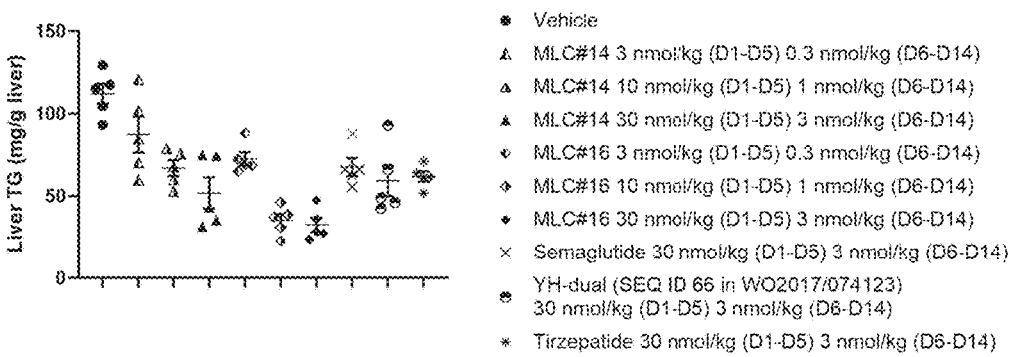
Figure 5K:
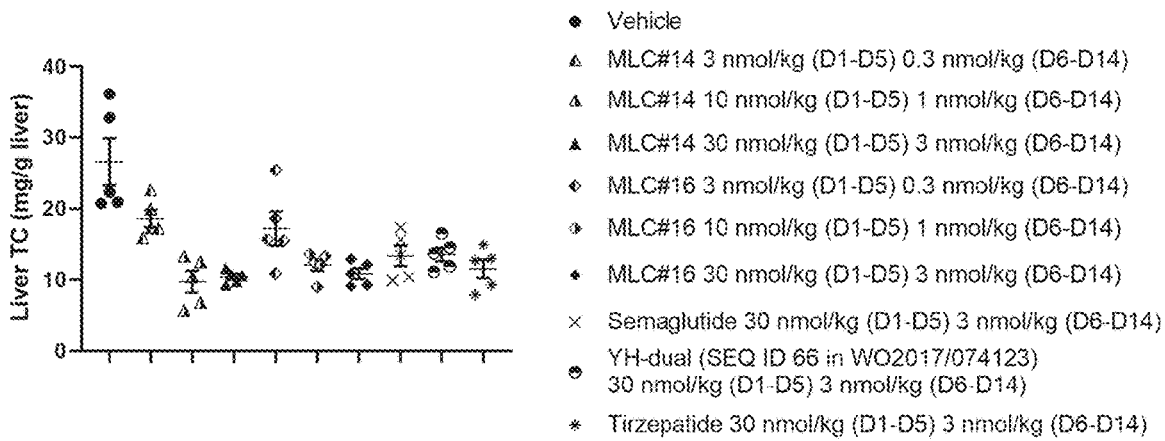
Figure 5L:
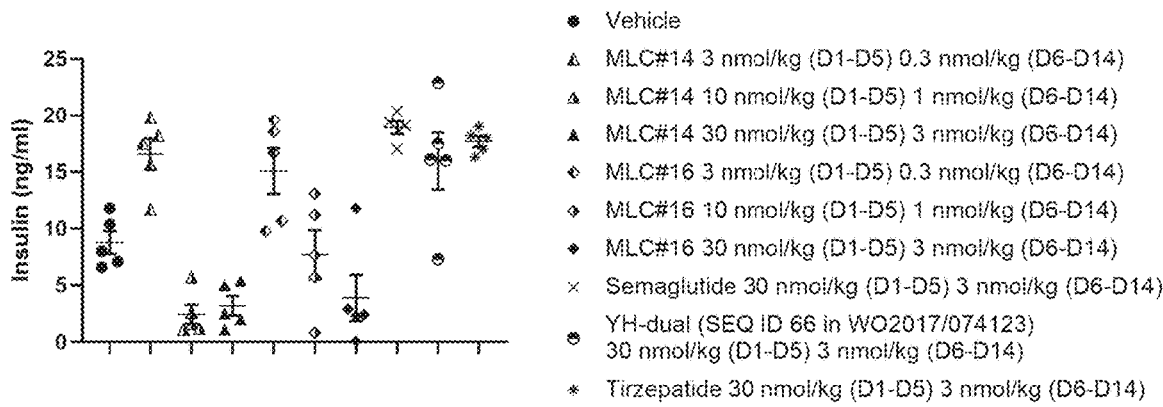
Figure 5M:
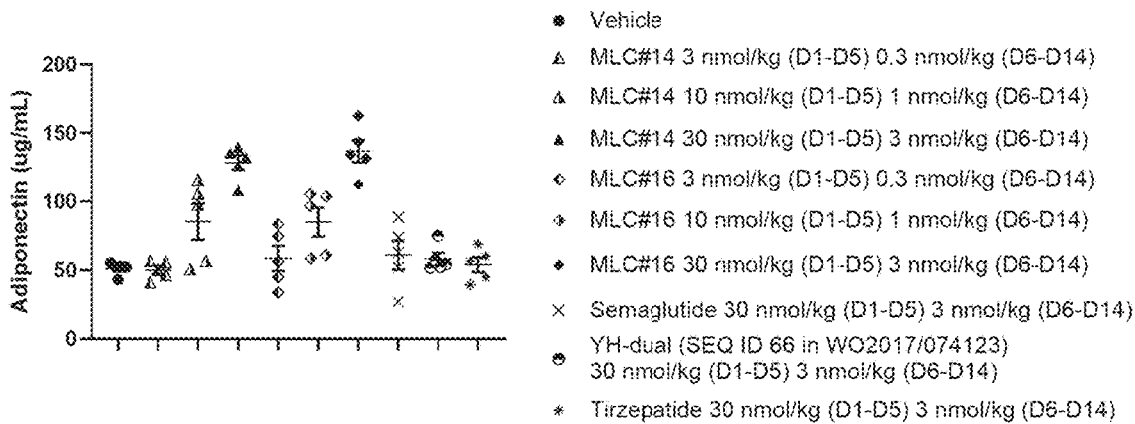

Conclusion: in ob/ob mice study, as shown in FIG. 5A-5M, the fusion molecule MLC #14 and MLC #16 showed dose-dependent efficacy on body weight reduction (FIG. 5A), glucose lowering and biomarkers changes. In FIG. 5A, molecule MLC #14 and MLC #16 showed much better efficacy on body weight reduction compared to Semaglutide, Tirzepatide and YH-dual (SEQ ID 66 in WO2017/074123) at the same dosage. In FIG. 5B, MLC #14 and MLC #16 groups reached similar effect on glucose control as Semaglutide at the same dosage. As shown in FIG. 5C, MLC #14 and MLC #16 induced better reduction of plasma triglyceride compared to Semaglutide, Tirzepatide and YH-dual at the same dosage. MLC #14 and MLC #16 also reduced the level of LDL-C (FIG. 5D), total cholesterol (FIG. 5E), ALT (FIG. 5F) and AST (FIG. 5G) concentration in plasma and reduction of adipose weight (FIG. 5H) and liver weight (FIG. 5I) along with the improvement of liver TG (FIG. 5J), liver TC (FIG. 5K) and insulin sensitivity (FIG. 5L). The fusion molecule MLC #14 and MLC #16 showed significantly better effect on increase of adiponectin level than YH-dual at the same dosage indicating the better FGF21 activity (FIG. 5M).

D) Metabolic Parameters in DIO Animal Model

Method: 16 week old DIO male C57BL/6 mice (35~50 g) were injected once daily (QD) subcutaneously with designated GLP-1/FGF21 conjugates and FGF21 conjugates (i.e., MLC #16, MLC #19, MLC #6 and MLC #23) for 22 days. Food intake and body weight were measured once every three days and fasting blood glucose was measured every weeks. Five animals were used for each treatment group. Body weight and blood glucose was monitored for each individual animal, but food intake for each group of animals was measured together. Day 1 and Day 22 are first day and last day respectively of the treatment. Terminal blood was collected and EDTA-K3 plasma was prepared and frozen at −80° C. for biomarker measurement (LDL-C, TC, TG). Liver and adipose tissue were also collected and frozen in liquid nitrogen and store at −80° C. Data are indicated as mean values and standard error (SEM) or pooled values. Statistical analysis was performed by One-way ANOVA.

Conclusion

Figure 6A:
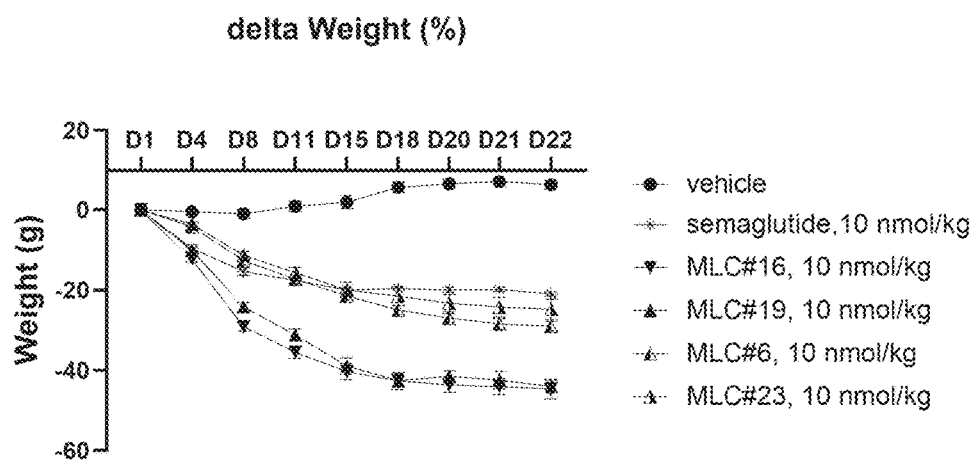
FIGS. 6A to 6H show efficacy of Molecules MLC #16, MLC #19, MLC #6, and MLC #23 at different dosages, in comparison to reference compounds semaglutide, serum triglyceride (FIG. 6C), LDL-C (FIG. 6D) and total cholesterol (FIG. 6E) concentration in plasma and reduction of adipose weight (FIG. 6F) and liver weight (FIG. 6G), along with the improvement of liver TG (FIG. 6H).
Figure 6B:
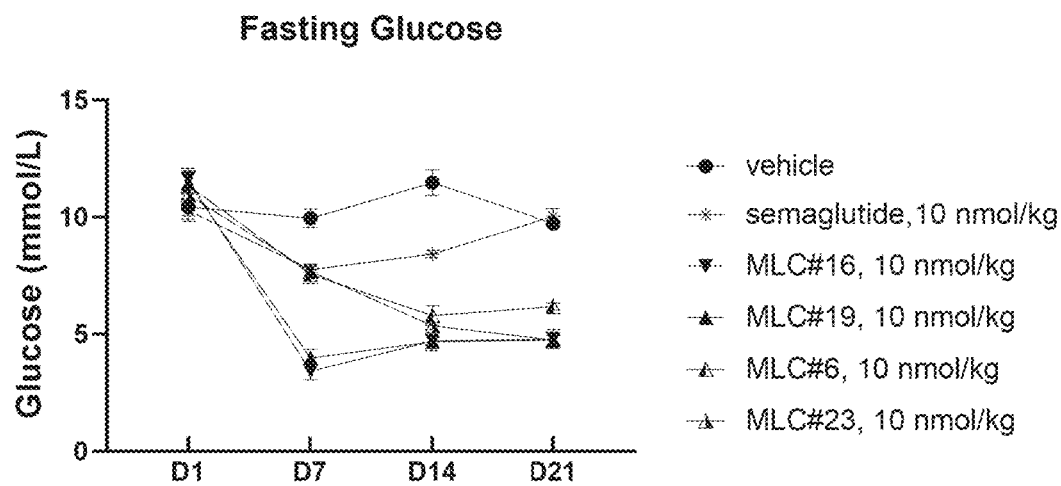
Figure 6C:
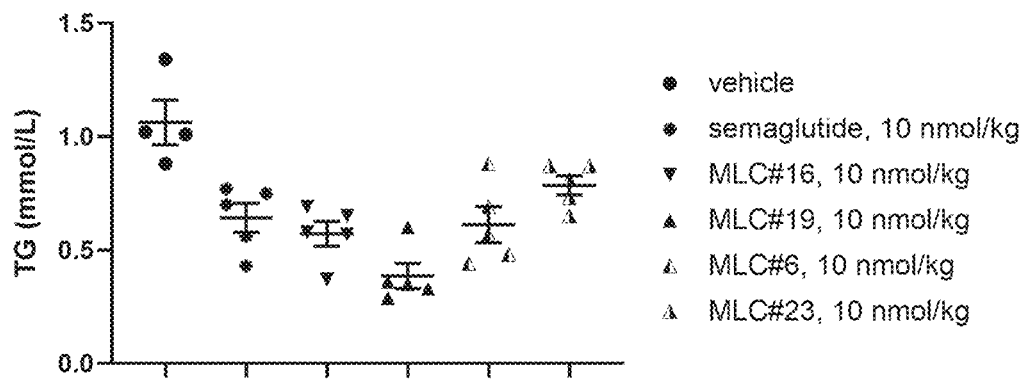
Figure 6D:
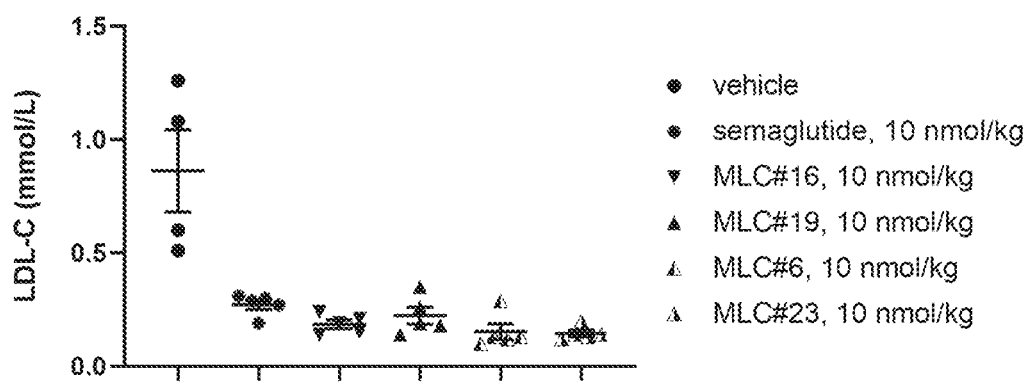
Figure 6E:
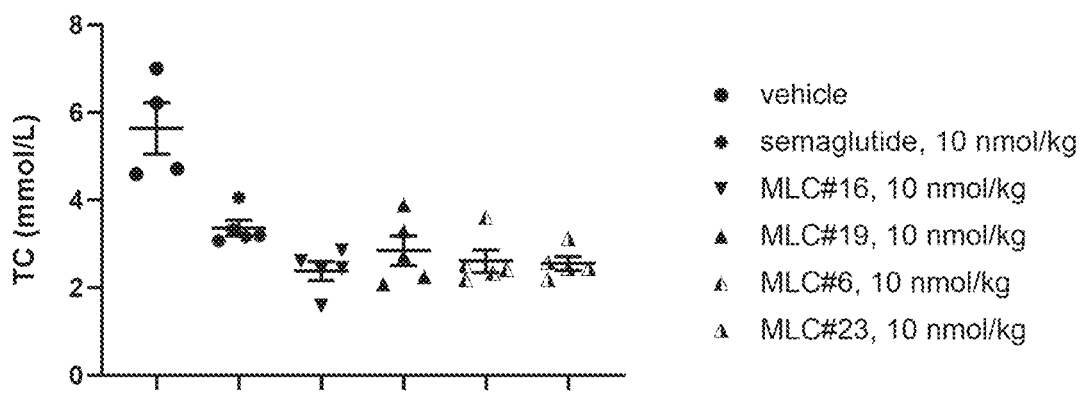
Figure 6F:
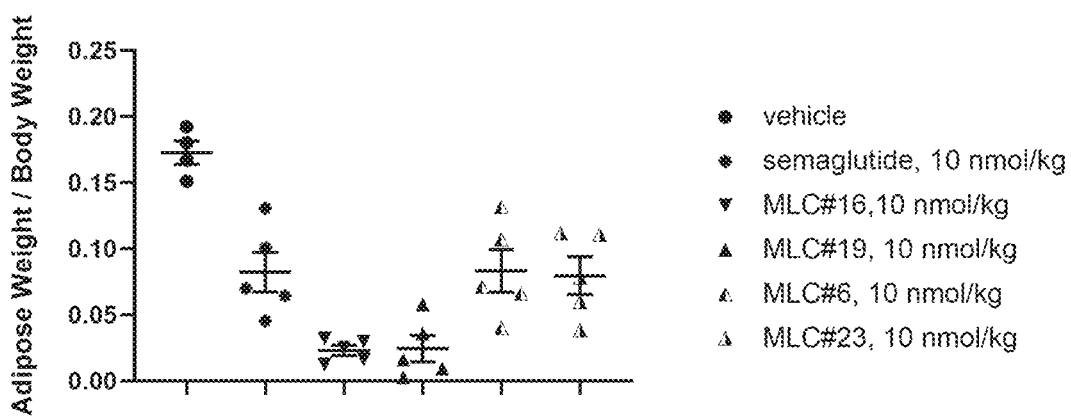
Figure 6G:
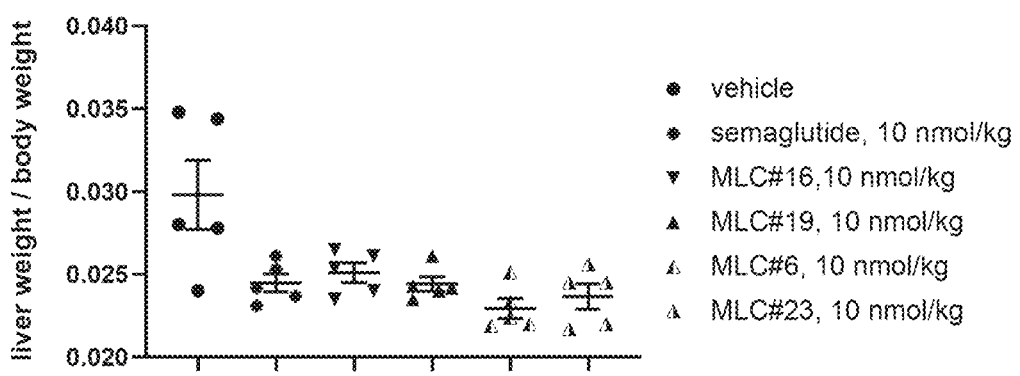
Figure 6H:
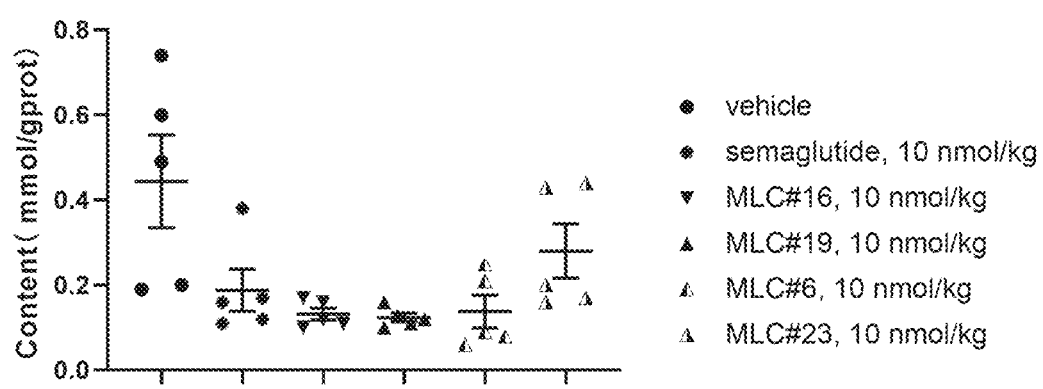

In DIO mice study, as shown in FIG. 6A, the GLP-1-Nanobody-FGF21 fusion proteins conjugates (MLC #16 and MLC #19) and the Nanobody-FGF21 fusion conjugates (MLC #6 and MLC #23) showed good efficacy on body weight reduction. In FIG. 6B, MLC #16, MLC #19, MLC #6 and MLC #23 groups showed better glucose control than Semaglutide, and also induced the reduction of serum triglyceride (FIG. 6C), LDL-C (FIG. 6D) and total cholesterol (FIG. 6E) concentration in plasma and reduction of adipose weight (FIG. 6F) and liver weight (FIG. 6G), along with the improvement of liver TG (FIG. 6H).

Example 7: Pharmacokinetic Study in Rat

Method: 6-8 weeks male SD rats were administrated in a single subcutaneous dose of 15 nmol/kg protein MLC #9 (conjugated) or MLC #10 (non-conjugated) (n=3/group). Plasma samples were collected pre-dose (−5 min), 0.5 hr, 1 hr, 2 hr, 4 hr, 6 hr, 8 hr, 12 hr, 24 hr, 32 hr, 48 hr, 72 hr, 96 hr, after subcutaneous administration. The concentrations of the polypeptide conjugates in the plasma were measured by ELISA method. Based on the graph showing plasma concentration of each polypeptide conjugate versus time after subcutaneous injection, the pharmacokinetic parameters were calculated by WinNonlin.

Conclusion: The MLC #9 has half-life $T_{1/2}$ of 14.3 hrs in rat which shows longer half life than the MLC #10 with half-life $T_{1/2}$ of 9.5 hrs.

Example 8: PK Study in Minipig

Pharmacokinetics of selected molecules are assessed in minipig. Both subcutaneous and intravenous injections are performed.

Example 9: PK Study in Non-Human Primates

Pharmacokinetics of selected molecules are assessed in monkeys. Both subcutaneous and intravenous injections are performed.

Methods: 4~5 years male Cynomolgus monkeys were administrated by a single subcutaneous dose of 5 mg/kg (123 nmol/kg) MLC #16 (n=2/group). Plasma samples were collected pre-dose (−5 min), 0.5 hr, 1 hr, 2 hr, 4 hr, 6 hr, 8 hr, 12 hr, 24 hr, 36 hr, 48 hr, 72 hr, 96 hr, 120 hr, 144 hr and 168 hr after subcutaneous administration. The concentrations of MLC #16 in the plasma were measured by LC-MS/MS method. Based on the graph showing plasma concentration of MLC #16 versus time after subcutaneous injection, the pharmacokinetic parameters were calculated by WinNonlin.

Conclusion: MLC #16 showed a half-life of 54.3 hours in monkey, which potentially supports a once weekly dose frequency in human (Table 9).

TABLE 9

Pharmacokinetic parameters of MLC#16 in monkeys. Pharmacokinetic data were analyzed by WinNonlin software. $T_{max}$, $C_{max}$, $T_{1/2}$, AUC were calculated.

| PK parameters | Unit | MLC#16 |
|---|---|---|
| $T_{max}$ | hr | 12 |
| $C_{max}$ | nmol/L | 671 |
| Terminal $t_{1/2}$ | hr | 54.3 |
| $AUC_{0-t}$ | hr*nmol/L | 47851 (t = 168 h) |

Example 10: Immunogenicity Assessment

Selected GLP-1 polypeptide conjugates are also assessed for immunogenicity by in silico (iTope and TCED methods) and ex vivo (EpiScreen) methods.

Example 11: Stability Assessment

To test the stability, the different GLP-1 polypeptide conjugates are formulated in buffers with different compositions (pH6, 7, 7.4 and 8.0) and stored at different temperatures (such as 4° C. and 25° C.) for 2-4 weeks. The % HMWP and % LMW are analyzed by size exclusion chromatography (SEC)-HPLC. The concentration and modifications were analyzed by reverse phase (RP)-UPLC and LC/MS.

Example 12: Human Serum Albumin Binding

Method: Binding of molecules to serum albumin was characterized by surface plasmon resonance in a Biacore 8K instrument. Human serum albumin was covalently bound to CM5 sensor chips surface until 4000 RU was reached. The chip was blocked by 1M ethanolamine with flowrate of 10 µL/min for 420 s. Each molecule sample was diluted and injected at a flow rate of 30 µL/min to allow for binding to chip-bound albumin for 120 s and for dissociation for 300 s. Binding buffer without molecule was sent over the chip at the flow rate of 20 seconds to allow spontaneous dissociation of bound molecule for 30 seconds.

Conclusion: All fusion molecules (MLC #9, MLC #10, Control #4, Control #5, Control #6, MLC #12 and MLC #16) show similar binding affinity to human serum albumin (see Table 10).

TABLE 10

Human serum albumin binding affinity

| Molecule | KD (µM) | Rmax (RU) |
|---|---|---|
| MLC#9 (conjugated) | 0.28 | 1507.8 |
| MLC#10 (non-conjugated) | 0.28 | 1391.0 |
| Control#4 | 0.27 | 1252.0 |
| Control#5 | 0.22 | 1604.0 |
| Control#6 | 0.22 | 1289.8 |
| MLC#12 (non-conjugated) | 0.25 | 1248.6 |
| MLC#13 (conjugated) | 0.27 | 1393.3 |
| MLC#14 (conjugated) | 0.22 | 1513.5 |
| MLC#15 (conjugated) | 0.31 | 1341.8 |
| MLC#16 (conjugated) | 0.27 | 1625.6 |
| MLC#19 (conjugated) | 0.22 | 450.0 |

Example 13: FAP Enzyme Cleavage on the Fusion Proteins

Method: Fibroblast activation protein (FAP) is a serine protease. This enzyme has been reported to regulate degradation of FGF21, In order to test the C terminal degradation of the fusion protein by FAP enzyme, the fusion protein (MLC #23, MLC #25) and FAP enzyme were incubated with ration 200:1 at 37° C. for 20 hours. LC-MS were performed to analyze the degradation percentage of the fusion protein.

Conclusion: The fusion protein without conjugation (MLC #25, MLC #18 and MLC #21) showed 50.6-65.2% C-terminal degradation when incubation with FAP enzyme at 37° C. for 20 hours. However, the fusion protein conjugate (MLC #23, MLC #16 and MLC #19) and the fusion protein with 171G substitution (MLC #10) showed resistance to FAP enzyme.

TABLE 11

Result of fusion proteins by FAP enzyme cleavage

| Molecule | C-terminal degradation |
|---|---|
| MLC#23 (conjugated) | Not detected |
| MLC#25 (non-conjugated, 171P) | 58.9% |
| MLC#16 (conjugated) | Not detected |
| MLC#18 (non-conjugated, 171P) | 65.2% |
| MLC#19 (conjugated) | Not detected |
| MLC#21 (non-conjugated, 171P) | 50.6% |
| MLC#10 (non-conjugated, 171G) | Not detected |

The invention claimed is:

1. A polypeptide, comprising, in a direction from N terminus to C terminus:
   a first fragment comprising a nanobody domain capable of binding to serum albumin; and
   a second fragment comprising a biologically active FGF21 domain, wherein the FGF21 domain comprises the amino acid sequence of SEQ ID NOs: 6-10, 13 and 92;
   wherein:
   the first fragment and the second fragment are connected via a first linker;
   the polypeptide further comprising, over an N-terminus of the first fragment, a third fragment comprising a biologically active peptide, or a fragment thereof, of GLP-1,
   wherein:
   the first fragment and the third fragment are connected via a second linker.

2. The polypeptide of claim 1, wherein the FGF21 domain comprises a conjugatable residue, wherein the polypeptide is conjugated with a functional moiety at the conjugatable residue.

3. The polypeptide of claim 2, wherein:
   the conjugatable residue is at a position selected from the group consisting of positions 169, 170, 171, 172, 173, 174, 180 and 181 relative to SEQ ID NO: 1.

4. The polypeptide of claim 2, wherein the functional moiety comprises a synthetic chemical moiety, wherein the synthetic chemical moiety comprises a structure of *—X—Y—Z, wherein X, Y, and Z are interconnected via bonds, and the * end of X is connected to the conjugatable residue on the polypeptide, wherein:
   X can be

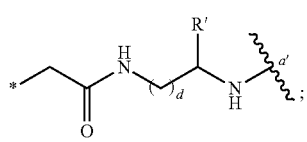

Y can be

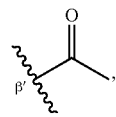 [SMILES: *C(C)=O]

and Z can be

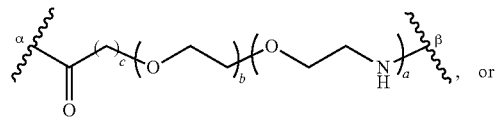, or

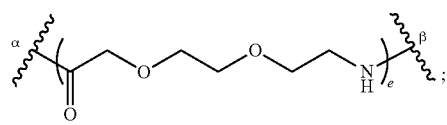;

wherein:
position α is linked to position α', position β is linked to position β', R1 is hydrogen or —COOH; d is 1, 2, or 3; a is 1, 2 or 3; b is 1, 2 or 3; c is 1 or 2; and d is 1, 2, or 3, and e is 1, 2, or 3.

5. The polypeptide of claim 4, wherein the synthetic chemical moiety has the below structure:

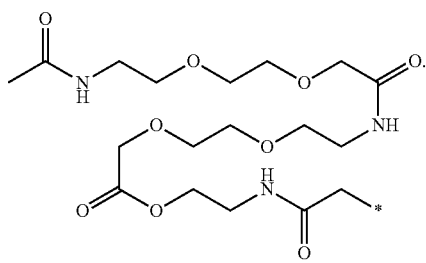 [SMILES: *CC(=O)NCCOC(=O)COCCOCCNC(=O)COCCOCCNC(C)=O]

6. The polypeptide of claim 5, wherein the conjugatable residue comprises an introduced cysteine residue, wherein the introduced cysteine is at a position selected from a group consisting of 169, 170, 171, 172, 173, 174, and 181 relative to SEQ ID NO: 1.

7. The polypeptide of claim 1, wherein the nanobody domain comprises a VHH domain.

8. The polypeptide of claim 7, wherein the VHH domain comprises a complementarity determining region 1 (CDR1) comprising the sequence of SEQ ID NO: 20, a CDR2 comprising the sequence of SEQ ID NO: 21, and a CDR3 comprising the sequence of SEQ ID NO: 22.

9. The polypeptide of claim 8, wherein the VHH domain comprises an amino acid sequence of SEQ ID NO: 23, or a variant thereof having at least 70% identity to SEQ ID NO: 23, wherein the variant retains binding specificity and/or affinity to serum albumin.

10. The polypeptide of claim 1, wherein the first linker has a length of at least four amino acid residues.

11. The polypeptide of claim 1, wherein the biologically active peptide, or a fragment thereof, of GLP-1 comprises one or more mutations comprise A8G, G22E, K26R, K34R, R36G, or any combination thereof, relative to GLP-1 (7-37), the sequence of which is set forth in SEQ ID NO: 28.

12. The polypeptide of claim 11, wherein the biologically active peptide, or a fragment thereof, of GLP-1 comprises an amino acid sequence selected from the group consisting of SEQ ID NO: 29, and SEQ ID NOs: 31-34.

13. The polypeptide of claim 12, wherein the second linker has a length of at least eight amino acid residues.

14. The polypeptide of claim 13, comprising an amino acid sequence selected from SEQ ID NOS: 74, 81-83, 85, 94 and 96-97.

15. A pharmaceutical composition, comprising the polypeptide according to claim 1 and a pharmaceutically acceptable carrier.

16. A polynucleotide that encodes the polypeptide as defined in claim 1.

17. A vector comprising the polynucleotide according to claim 16.

18. A host cell comprising the vector according to claim 17.

19. The polypeptide of claim 1, comprising an amino acid sequence selected from SEQ ID NOS: 74, 81-83, 85 and 96-97, wherein the FGF21 domain comprises a conjugatable cysteine residue, the polypeptide is conjugated with a synthetic chemical moiety at the conjugatable cysteine residue, the conjugatable cysteine residue is at position 171.

20. The polypeptide of claim 1, comprising an amino acid sequence of SEQ ID NO: 94, wherein the FGF21 domain comprises a conjugatable cysteine residue, the polypeptide is conjugated with a synthetic chemical moiety at the conjugatable cysteine residue, the conjugatable cysteine residue is at position 174.

21. The polypeptide of claim 1, comprising an amino acid sequence of SEQ ID NO: 94, wherein the FGF21 domain comprises a conjugatable cysteine residue, the polypeptide is conjugated with a synthetic chemical moiety at the conjugatable cysteine residue, the conjugatable cysteine residue is at position 174, and the synthetic chemical moiety has the below structure:

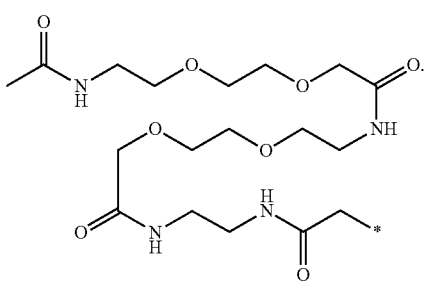 [SMILES: *CC(=O)NCCNC(=O)COCCOCCNC(=O)COCCOCCNC(C)=O]

22. A polypeptide comprising an amino acid sequence selected from SEQ ID NOS: 74, 81-83, 85 and 96-97, wherein the polypeptide comprises a conjugatable cysteine residue, the polypeptide is conjugated with a synthetic chemical moiety at the conjugatable cysteine residue, the conjugatable cysteine residue is at position 171, and the synthetic chemical moiety has the below structure:

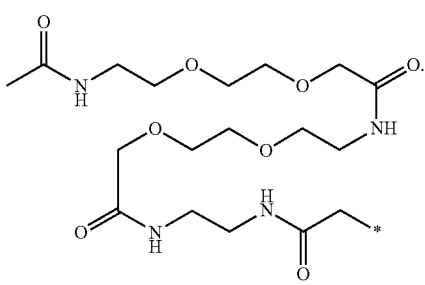 [SMILES: *CC(=O)NCCNC(=O)COCCOCCNC(=O)COCCOCCNC(C)=O]

23. A polypeptide comprising an amino acid sequence selected from SEQ ID NOS: 70, 75, 79-80, 95, 98, and 108-109.

* * * * *